(12) United States Patent
Vandepapeliere

(10) Patent No.: US 10,143,745 B2
(45) Date of Patent: Dec. 4, 2018

(54) VACCINE COMPOSITIONS COMPRISING A SAPONIN ADJUVANT

(71) Applicant: GLAXOSMITHKLINE BIOLOGICALS S.A., Rixensart (BE)

(72) Inventor: Pierre Vandepapeliere, Rixensart (BE)

(73) Assignee: GlacoSmithKline Biologicals, S.A., Rixensart (BE)

( * ) Notice: Subject to any disclaimer, the term of this patent is extended or adjusted under 35 U.S.C. 154(b) by 0 days.

(21) Appl. No.: 15/354,233

(22) Filed: Nov. 17, 2016

(65) Prior Publication Data

US 2017/0065715 A1 Mar. 9, 2017

Related U.S. Application Data

(63) Continuation of application No. 13/020,045, filed on Feb. 3, 2011, which is a continuation of application No. 12/096,838, filed as application No. PCT/GB2006/004634 on Dec. 12, 2006, now abandoned.

(30) Foreign Application Priority Data

| Dec. 13, 2005 | (GB) | 0525321.6 |
| May 18, 2006 | (GB) | 0609902.2 |
| Oct. 12, 2006 | (GB) | 0620336.8 |
| Oct. 12, 2006 | (GB) | 0620337.6 |

(51) Int. Cl.
| *A61K 38/00* | (2006.01) |
| *A61K 39/00* | (2006.01) |
| *A61K 39/02* | (2006.01) |
| *A61K 39/39* | (2006.01) |
| *A61K 39/12* | (2006.01) |
| *A61K 39/145* | (2006.01) |
| *A61K 39/015* | (2006.01) |
| *A61K 39/09* | (2006.01) |
| *A61K 39/102* | (2006.01) |
| *A61K 39/104* | (2006.01) |

(52) U.S. Cl.
CPC .............. *A61K 39/39* (2013.01); *A61K 39/00* (2013.01); *A61K 39/015* (2013.01); *A61K 39/092* (2013.01); *A61K 39/102* (2013.01); *A61K 39/1045* (2013.01); *A61K 39/12* (2013.01); *A61K 39/145* (2013.01); *A61K 2039/5258* (2013.01); *A61K 2039/545* (2013.01); *A61K 2039/55* (2013.01); *A61K 2039/55505* (2013.01); *A61K 2039/55555* (2013.01); *A61K 2039/55572* (2013.01); *A61K 2039/55577* (2013.01); *A61K 2039/57* (2013.01); *A61K 2039/6037* (2013.01); *A61K 2039/6068* (2013.01); *A61K 2039/70* (2013.01); *C12N 2710/16134* (2013.01); *C12N 2710/16171* (2013.01); *C12N 2710/16734* (2013.01); *C12N 2710/16771* (2013.01); *C12N 2710/20071* (2013.01); *C12N 2730/10134* (2013.01); *C12N 2760/16134* (2013.01); *C12N 2760/16171* (2013.01); *C12N 2760/16234* (2013.01); *C12N 2760/16271* (2013.01); *C12N 2760/20034* (2013.01); *Y02A 50/412* (2018.01)

(58) Field of Classification Search
CPC ......... A61K 38/00; A61K 39/00; A61K 39/02
USPC ...... 424/9.1, 9.2, 234.1, 251.1, 256.1, 278.1
See application file for complete search history.

(56) References Cited

U.S. PATENT DOCUMENTS

| 3,238,190 A | 3/1966 | Erbring et al. |
| 4,270,537 A | 6/1981 | Romaine |
| 4,372,945 A | 2/1983 | Likhite |
| 4,436,727 A | 3/1984 | Ribi |
| 4,474,757 A | 10/1984 | Arnon et al. |
| 4,596,556 A | 6/1986 | Morrow et al. |
| 4,790,824 A | 12/1988 | Morrow et al. |
| 4,866,034 A | 9/1989 | Ribi |
| 4,877,611 A | 10/1989 | Cantrell |
| 4,886,499 A | 12/1989 | Cirelli et al. |
| 4,912,094 A | 3/1990 | Myers et al. |
| 4,940,460 A | 7/1990 | Casey et al. |
| 4,941,880 A | 7/1990 | Burns |

(Continued)

FOREIGN PATENT DOCUMENTS

| EP | 0198474 B1 | 10/1986 |
| EP | 0281673 A1 | 9/1988 |

(Continued)

OTHER PUBLICATIONS

Berezin et al., Controlled organization of multimolecular complexes of enveloped virus glycoproteins: study of immunogenicity, Vaccine (1988) 6(5):450-456.

(Continued)

*Primary Examiner* — Rodney P Swartz
(74) *Attorney, Agent, or Firm* — Virginia G. Campen

(57) ABSTRACT

The present invention provides a human dose of an immunogenic composition comprising an antigen or antigenic preparation, in combination with an adjuvant which adjuvant comprises an immunologically active saponin fraction derived from the bark of *Quillaja saponaria Molina* presented in the form of a liposome and a lipopolysaccharide wherein said saponin fraction and said lipopolysaccharide are both present in said human dose at a level of below 30 μg. The present invention further provides an adjuvant composition in a human dose suitable volume comprising between 1 and 30 μg of a lipopolysaccharide and between 1 and 30 μg of an immunologically active saponin fraction presented in the form of a liposome.

13 Claims, 27 Drawing Sheets
Specification includes a Sequence Listing.

(56) References Cited

U.S. PATENT DOCUMENTS

| | | |
|---|---|---|
| 4,946,069 A | 8/1990 | Fuchs |
| 4,963,484 A | 10/1990 | Kufe |
| 5,015,235 A | 5/1991 | Grossman |
| 5,057,540 A | 10/1991 | Kensil et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,368,201 A | 11/1994 | Fuchs |
| 5,383,851 A | 1/1995 | McKinnon, Jr. et al. |
| 5,417,662 A | 5/1995 | Hjertman et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |
| 5,654,140 A | 8/1997 | Persico et al. |
| 5,668,267 A | 9/1997 | Watson et al. |
| 5,704,911 A | 1/1998 | Parsons |
| 5,744,144 A | 4/1998 | Finn et al. |
| 5,750,110 A | 5/1998 | Prieels et al. |
| 5,766,608 A | 6/1998 | Kolattukudy et al. |
| 5,786,148 A | 7/1998 | Bandman et al. |
| 5,801,005 A | 9/1998 | Cheever et al. |
| 5,804,193 A | 9/1998 | Briles et al. |
| 5,827,666 A | 10/1998 | Finn et al. |
| 5,840,871 A | 11/1998 | Hillman et al. |
| 5,843,464 A | 12/1998 | Bakaletz et al. |
| 5,893,397 A | 4/1999 | Peterson et al. |
| 5,955,306 A | 9/1999 | Gimeno et al. |
| 5,981,215 A | 11/1999 | Meissner et al. |
| 5,985,610 A | 11/1999 | Lowy et al. |
| 5,993,412 A | 11/1999 | Deily et al. |
| 6,054,438 A | 4/2000 | Taylor-Papadimitriou et al. |
| 6,245,568 B1 | 6/2001 | Volkin et al. |
| 6,261,765 B1 | 7/2001 | McCarthy et al. |
| 6,361,778 B1 | 3/2002 | Gissmann et al. |
| 6,416,945 B1 | 7/2002 | McCarthy et al. |
| 6,599,508 B1 | 7/2003 | Gissmann et al. |
| 6,610,028 B1 | 8/2003 | Alexandre et al. |
| 6,623,446 B1 | 9/2003 | Navelier et al. |
| 6,649,167 B2 | 11/2003 | Hallek et al. |
| 6,666,843 B1 | 12/2003 | Alexandre et al. |
| 6,758,829 B2 | 7/2004 | Alexandre et al. |
| 6,835,187 B2 | 12/2004 | Alexandre et al. |
| 6,837,866 B1 | 1/2005 | Alexandre et al. |
| 6,911,015 B2 | 6/2005 | Alexandre et al. |
| 6,913,593 B1 | 7/2005 | Alexandre et al. |
| 6,942,645 B2 | 9/2005 | Alexandre et al. |
| 6,964,650 B2 | 11/2005 | Alexandre et al. |
| 7,056,300 B2 | 6/2006 | Alexandre et al. |
| 7,147,862 B1 | 12/2006 | Prieels et al. |
| 7,261,702 B1 | 8/2007 | Alexandre et al. |
| 7,513,885 B2 | 4/2009 | Navelier et al. |
| 7,559,917 B2 | 7/2009 | Alexandre et al. |
| 7,939,084 B1 | 5/2011 | Hanon et al. |
| 2001/0053365 A1 | 12/2001 | Friede et al. |
| 2003/0219453 A1 | 11/2003 | Maisonneuve et al. |
| 2003/0235593 A1 | 12/2003 | Skeiky et al. |
| 2008/0154189 A1 | 6/2008 | Alexandre et al. |

FOREIGN PATENT DOCUMENTS

| | | | |
|---|---|---|---|
| EP | 0304578 A1 | 3/1989 | |
| EP | 0414374 A2 | 2/1991 | |
| EP | 0477231 B1 | 4/1992 | |
| EP | 0497524 A2 | 8/1992 | |
| EP | 0497525 A2 | 8/1992 | |
| EP | 0594610 B1 | 5/1994 | |
| EP | 0595935 B1 | 5/1994 | |
| EP | 0834568 A2 | 4/1998 | |
| EP | 0837130 A2 | 4/1998 | |
| EP | 1092444 A1 | 4/2001 | |
| GB | 2220211 A | 1/1990 | |
| WO | 88/05054 A1 | 7/1988 | |
| WO | 90/01496 A1 | 2/1990 | |
| WO | 90/06951 A1 | 6/1990 | |
| WO | 92/14488 A1 | 9/1992 | |
| WO | 93/00436 A1 | 1/1993 | |
| WO | 93/02184 A1 | 2/1993 | |
| WO | 93/03761 A1 | 3/1993 | |
| WO | 93/10152 A1 | 5/1993 | |
| WO | 94/00150 A1 | 1/1994 | |
| WO | 94/00152 A1 | 1/1994 | |
| WO | 94/00153 A1 | 1/1994 | |
| WO | 94/05792 A1 | 3/1994 | |
| WO | 94/12641 A1 | 6/1994 | |
| WO | 94/20137 A1 | 9/1994 | |
| WO | 94/21292 A1 | 9/1994 | |
| WO | 94/26304 A1 | 11/1994 | |
| WO | 95/08348 A1 | 3/1995 | |
| WO | 95/17209 A1 | 6/1995 | |
| WO | 95/17210 A1 | 6/1995 | |
| WO | 95/20600 A1 | 8/1995 | |
| WO | 95/31555 A1 | 11/1995 | |
| WO | 96/05859 A1 | 2/1996 | |
| WO | 96/11272 A2 | 4/1996 | |
| WO | 96/26277 A1 | 8/1996 | |
| WO | 96/29413 A2 | 9/1996 | |
| WO | 96/33739 A1 | 10/1996 | |
| WO | 96/34960 A1 | 11/1996 | |
| WO | 96/40928 A1 | 12/1996 | |
| WO | 97/01638 A1 | 1/1997 | |
| WO | 97/09994 A1 | 3/1997 | |
| WO | 97/13537 A1 | 4/1997 | |
| WO | 97/13785 A1 | 4/1997 | |
| WO | 97/18837 A1 | 5/1997 | |
| WO | 97/32980 A1 | 9/1997 | |
| WO | 97/37705 A1 | 10/1997 | |
| WO | 97/41151 A2 | 11/1997 | |
| WO | 97/41731 A1 | 11/1997 | |
| WO | 98/06734 A1 | 2/1998 | |
| WO | 98/12302 A1 | 3/1998 | |
| WO | 98/15287 A1 | 4/1998 | |
| WO | 98/18930 A2 | 5/1998 | |
| WO | 98/20117 A1 | 5/1998 | |
| WO | 98/21337 A2 | 5/1998 | |
| WO | 98/33923 A1 | 8/1998 | |
| WO | 98/37418 A2 | 8/1998 | |
| WO | 98/39450 A2 | 9/1998 | |
| WO | 98/45328 A2 | 10/1998 | |
| WO | WO98/43670 | * 10/1998 | ............. A61K 39/39 |
| WO | 98/50567 A1 | 11/1998 | |
| WO | 98/55606 A2 | 12/1998 | |
| WO | 98/57659 A1 | 12/1998 | |
| WO | 99/03884 A2 | 1/1999 | |
| WO | 99/10375 A2 | 3/1999 | |
| WO | 99/11241 A1 | 3/1999 | |
| WO | 99/13056 A1 | 3/1999 | |
| WO | 99/15675 A1 | 4/1999 | |
| WO | 99/19479 A1 | 4/1999 | |
| WO | 99/33869 A2 | 7/1999 | |
| WO | 99/34850 A1 | 7/1999 | |
| WO | 99/40188 A2 | 8/1999 | |
| WO | 99/51188 A2 | 10/1999 | |
| WO | 99/51266 A2 | 10/1999 | |
| WO | 99/51748 A2 | 10/1999 | |
| WO | 99/53061 A2 | 10/1999 | |
| WO | 99/53940 A1 | 10/1999 | |
| WO | 99/57277 A2 | 11/1999 | |
| WO | 99/58684 A2 | 11/1999 | |
| WO | 99/63093 A2 | 12/1999 | |
| WO | 99/64067 A2 | 12/1999 | |
| WO | 99/64448 A2 | 12/1999 | |
| WO | 99/64602 A2 | 12/1999 | |
| WO | 00/04149 A2 | 1/2000 | |
| WO | 00/15802 A1 | 3/2000 | |
| WO | 00/17370 A1 | 3/2000 | |

(56) References Cited

FOREIGN PATENT DOCUMENTS

| | | | |
|---|---|---|---|
| WO | 00/29434 | A2 | 5/2000 |
| WO | 00/30299 | A1 | 5/2000 |
| WO | 00/37105 | A2 | 6/2000 |
| WO | 00/44899 | A1 | 8/2000 |
| WO | 00/52042 | A1 | 9/2000 |
| WO | 00/52165 | A2 | 9/2000 |
| WO | 00/56359 | A2 | 9/2000 |
| WO | 00/62800 | A2 | 10/2000 |
| WO | 00/76540 | A2 | 12/2000 |
| WO | 01/09179 | A1 | 2/2001 |
| WO | 01/09329 | A1 | 2/2001 |
| WO | 01/09334 | A1 | 2/2001 |
| WO | 01/09336 | A1 | 2/2001 |
| WO | 01/17550 | A2 | 3/2001 |
| WO | 01/17551 | A2 | 3/2001 |
| WO | 02/12292 | A2 | 2/2002 |
| WO | 02/22167 | A2 | 3/2002 |
| WO | 02/22168 | A2 | 3/2002 |
| WO | 02/32454 | A1 | 4/2002 |
| WO | 02/067983 | A1 | 9/2002 |
| WO | 2002/078637 | A2 | 10/2002 |
| WO | 02/097072 | A2 | 12/2002 |
| WO | WO03/028760 | A2 * | 4/2003 ............ A61K 39/39 |
| WO | 05/117958 | A1 | 12/2005 |
| WO | 2006/104890 | A2 | 10/2006 |
| WO | 2006/114312 | A2 | 11/2006 |
| WO | 2006/117240 | A2 | 11/2006 |
| WO | 2006/123155 | A2 | 11/2006 |

OTHER PUBLICATIONS

Berry and Paton, Sequence Heterogeneity of PsaA, a 37-Kilodalton Putative Adhesin Essential for Virulence of *Streptococcus pneumoniae*, Infect & Immun (1996) 64(12):5255-5262.
Bommer, Advances in Nasal Drug Delivery Technology, Pharmaceutical Technology Europe (Sep. 1999) 11:26-33.
Cason, et al., Papillomavirus Vaccines, J Clin Immunother (1994) 1(4):293-306.
Chaloupka, et al., Comparative Analysis of Six European Influenza Vaccines, Eur J Clin Microbiol Infect Dis (1996) 15:121-127.
Correale, et al., In Vitro Generation of Human Cytotoxic T Lymphocytes Specific for Peptides Derived From Prostate-Specific Antigen, J Nt'l Cancer Inst (1997) 89:293-300.
Dalsgaard, K., Saponin Adjuvants, Archiv Fur die gesamte Virusforschung, (1974) 44:243-254.
De Donato, et al., Safety and immunogenicity of MF59-adjuvanted influenza vaccine in the elderly, Vaccine (1999)17:3094-3101.
Deliyannis et al., Immunopotentiation of humoral and cellular response to inactivated influenza vaccines by two different adjuvants with potential for human use, Vaccine (1998) 16(20): 2058-2068.
Gelder, et al, Human CD4+ T-Cell Repertoire of Responses to Influenza A Virus Hemagglutinin after Recent Natural Infection, J Viral (1995) 69(12):7497-7506.
Gelder, et al, Human CD4+ T-Cell Recognition of Influenza A Virus Hemagglutinin after Subunit Vaccination, J Viral (1996) 70(7):4787-4790.
Gelder, et al, Six unrelated HLA-DR-matched adults recognize identical CD4+ T cell epitopes from influenza A haemagglutinin that are not simply peptides with high HLA-DR binding affinities, Int'l Immunol (1998) 10(2):211-222.
Gluck, Reinhard, Immunopotentiating reconstituted influenza virosomes (IRIVs) and other adjuvants for improved presentation of small antigens, Vaccine (1992) 10(13):915-919.
Govaert, et al., Abstract. The efficacy of influenza vaccination in elderly individuals. A randomized double-blind placebo-controlled trial, JAMA (1994) 272(21):1661-1655.
Gross, et al., The Efficacy of Influenza Vaccine in Elderly Persons: A Meta-Analysis and Review of the Literature, Annals of Internal Medicine (1995) 123(7):518-527.

Hagensee, Progress in the Development of HPV Vaccines, Infect Med (1997) 14(7):555-556, 559-564.
Helminen, et al., A Major Outer Membrane Protein of Moraxella catarrhalis Is a Target for Antibodies That Enhance Pulomonary Clearance of a Pathogen in an Animal Model, Infect & Immun (1993) 61(5):2003-2010.
Hubert, et al., STEAP: A prostate-specific cell surface antigen highly expressed in human prostate tumors, PNAS (1999) 96(25):14523-14528.
Johnson, et al., Characterization of a nontoxic monophosphoryl lipid A, Rev Infect Dis (1987) 9(Suppl 5):S512- S516, Abstract.
Kolberg and Sletten, Monoclonal Antibodies that Recognize a Common Pneumococcal Protein with Similarities to Streptococcal Group A Surface Glyceraldehyde-3-Phosphate Dehydrogenase, Infect & Immun (1996) 64(9): 3544-3547.
Lu et al., A Novel Gene (PLU-1) Containing Highly Conserved Putative DNA/Chromatin Binding Motifs Is Specifically Up-regulated in Breast Cancer, J Biol Chem (1999) 274(22):15633-15645.
Luderitz, et al., Structural Relationships of *Samonella* O and R Antigens, Annals NY Acad Sci (1966) 133:349-374.
McCarthy, et al., Quantitative Disassembly and Reassembly of Human Papillomavirus Type 11 Viruslike Particles in Vitro, J Viral (1998) 72(1):32-41.
Mischler and Metcalfe, Inflexal®V a trivalent virosome subunit influenza vaccine: production, (2002) Vaccine 20 (Supp5): B17-B23.
Murasko, et al., Role of humoral and cell-mediated immunity in protection from influenza disease after immunization of healthy elderly, Experimental Gerontology (2002) 37:427-439.
Nakajima, et al., Genetic relationship between the HA genes of type A influenza viruses isolated in off-seasons and later epidemic seasons, Epidemiol Infect (1991) 106:383-395.
Nelson, et al., Molecular cloning and characterization of prostase, an androgen-regulated serine protease with prostate-restricted expression, Proc Natl Acad Sci USA (1999) 96:3114-3119.
Petrovsky, et al., Vaccine adjuvant: Current state and future trends, Immunol & Cell Biol (2004) 82:488-496.
Puig-Barbera, et al., Effectiveness of the MF59-adjuvanated influenza vaccine in preventing emergency admissions for pneumonia in the elderly over 64 years of age, Vaccine (2004) 23:283-289.
Reed, et al., Tuberculosis vaccine development—from mouse to man, Microbes & Infection (2005) 7:922-931.
Robbins and Kawakami, Human tumor antigens recognized by T cells, Current Opinion in Immunology (1996) 8:628-636.
Ronda, et al., Biological role of the pneumococcal amidase, Eur J Biochem (1987) 164:621-624.
Salomon, et al., Cripto: a novel epidermal growth factor (EGF)-related peptide in mammary gland development and neoplasia, Bioessays (1999) 21:61-70.
Sanchez-Beato., et al, Molecular characterization of PcpA: a nove choline-binding protein of *Streptococcus pneumoniae*, FEMS Microbiology Letters (1998) 164:207-214.
Schmidt, et al., Recombinant Bovine/Human Parainfluenza Virus Type 3 (B/HIPV3) Expressing the Respiratory Syncytial Virus (RSV) G and F Proteins Can Be Used To Achieve Simultaneous Mucosal Immmunization against RSV and HPIV3, J Virol (2001) 75(10):4594-4603.
Van Den Eynde and Boon, Tumor antigens recognized by T lymphocytes, Int'l J Clin Lab Res (1997) 27:81-86.
Vandepapeliere, et al., Potent enhancement of cellular and humoral immune responses against recombinant hepatitis B antigens using AS02A adjuvant in healthy adults, Vaccine (2005) 23:2591-2601.
Vochten, et al., Physico-Chemical Properties of Sapoalbin and Their Relation to the Foam Stability, J Pharm Belg (1967) 42:213-226.
Weib, et al., Immunogenic properties of ISCOM prepared with influenza virus nucleoprotein, Archives of Virology (1990) 114:109-120.
Wiley, Don C., The Structure and Function of the Hemagglutinin Membrane Glycoprotein of Influenza Virus, Ann Rev Biochem (1987) 56:365-394.
Wood, et al., An improved single-radial-immunodiffusion technique for the assay of influenza haemagglutinin antigen: application for

(56) References Cited

OTHER PUBLICATIONS potency determinations of inactivated whole virus and subunit vaccines, J Biol Stand (1977) 5:237-247.

Wood, et al., International collaborative study of single-radial-diffusion and immunoelectrophoresis techniques for the assay of haemagglutinin antigen of influenza virus, J Biol Stand (1981) 9:317-330.

Yoshikawa, et al., Bioactive Saponins and Glycosides. III. Horese Chestnut. (1): The Structures, Inhibitory Effects on Ethanol Absorption, and Hypoglycemic Activity of Escins Ia, Ib, IIa, IIb, and IIIa from the Seeds of *Aesculus hippocastanum* L., Chem Pharm Bull (Tokyo) (1996) 44(8):1454-1464.

* cited by examiner

Figure 2A: Humoral immunity against H1N1 A/New Caledonia/20/99 strain of influenza following immunisation of ferrets with experimental formulations (Hemagglutination Inhibition Test (GMT +/- IC95))

| Anti-A/New Caledonia/20/99 H1N1 | Trivalent Split Plain | Trivalent Split MPL/QS21 in liposomes |
|---|---|---|
| D-4 Pre Prim | 20 | 10 |
| D17 Post Prim | 22 | 16 |
| D21 Post Imm | 143 | 640 |
| D13 Post Chall | 50 | 320 |

Figure 2B: Humoral immunity against B/Shangdong/7/97 strain of influenza following immunisation of ferrets with experimental formulations (Hemagglutination Inhibition Test (GMT +/- IC95))

| Anti-B/Shangdong/7/97 | Trivalent Split Plain | Trivalent Split MPL/QS21 in liposomes |
|---|---|---|
| D-4 Pre Prim | 10 | 10 |
| D17 Post Prim | 10 | 10 |
| D21 Post Imm | 10 | 180 |
| D13 Post Chall | 10 | 127 |

Figure 2C: Humoral immunity against H3N2 A/Panama/2007/99 strain of influenza following immunisation of ferrets with experimental formulations (Hemagglutination Inhibition Test (GMT +/- IC95))

Anti-A/Panama/2007/99 H3N2

| | Trivalent Split Plain | Trivalent Split MPL/QS21 in liposomes |
|---|---|---|
| D-4 Pre Prim | 16 | 16 |
| D17 Post Prim | 20 | 28 |
| D21 Post Imm | 57 | 3620 |
| D13 Post Chall | 2281 | 3620 |

Figure 2D: Humoral immunity against H3N2 A/Wyoming/3/2003 strain of influenza following immunisation of ferrets with experimental formulations (Hemagglutination Inhibition Test (GMT +/- IC95))

Anti-A/Wyoming/3/2003 H3N2

| | Trivalent Split Plain | Trivalent Split MPL/QS21 in liposomes |
|---|---|---|
| D-4 Pre Prim | 10 | 11 |
| D17 Post Prim | 11 | 10 |
| D21 Post Imm | 20 | 1437 |
| D13 Post Chall | 1437 | 2874 |

Figure 5
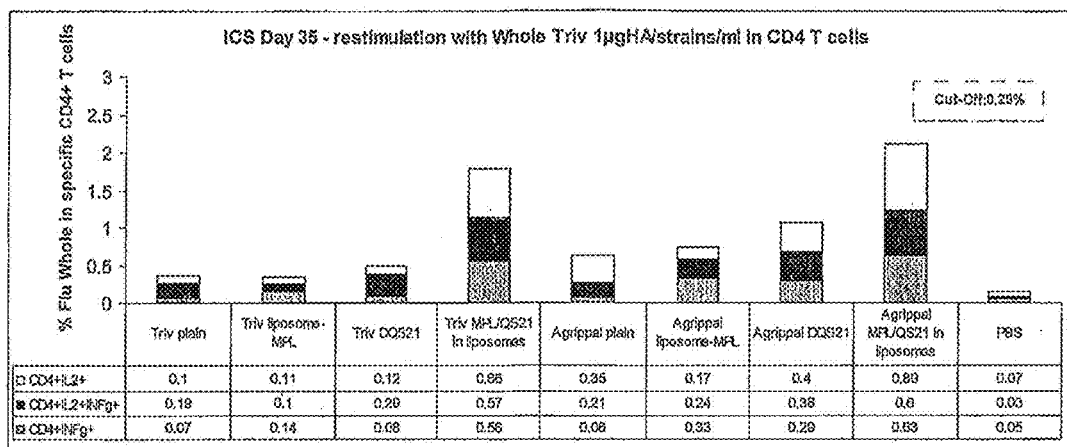
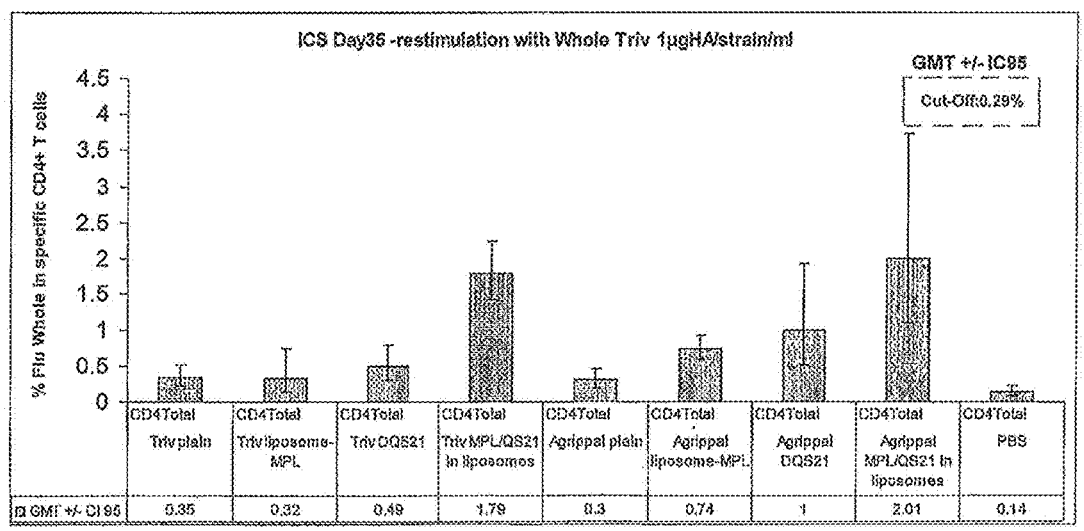

Figure 6
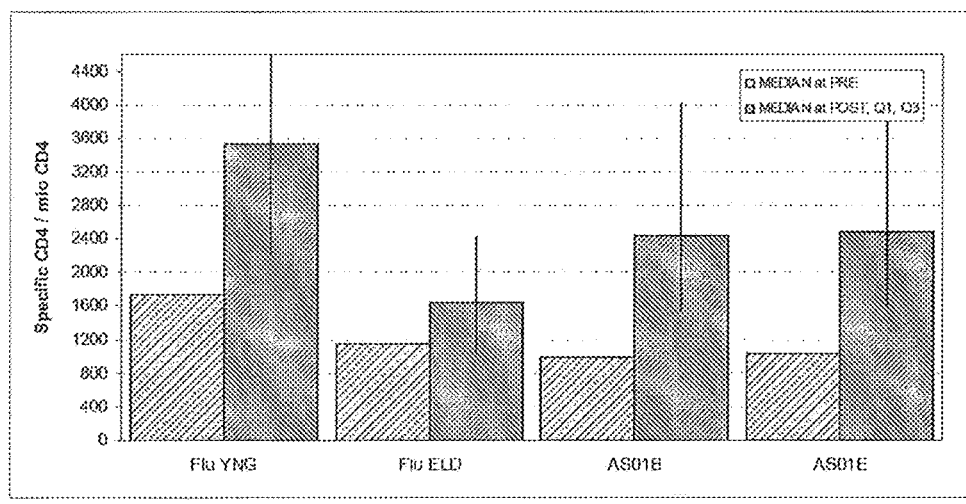
Figure 7 - GMTs at days 0 and 21 for HI antibodies
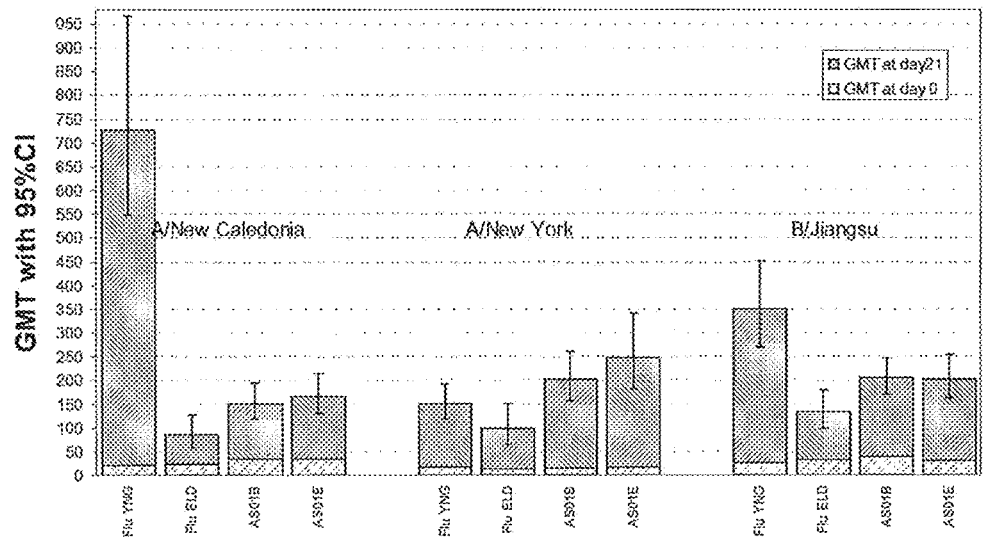

Figure 10:
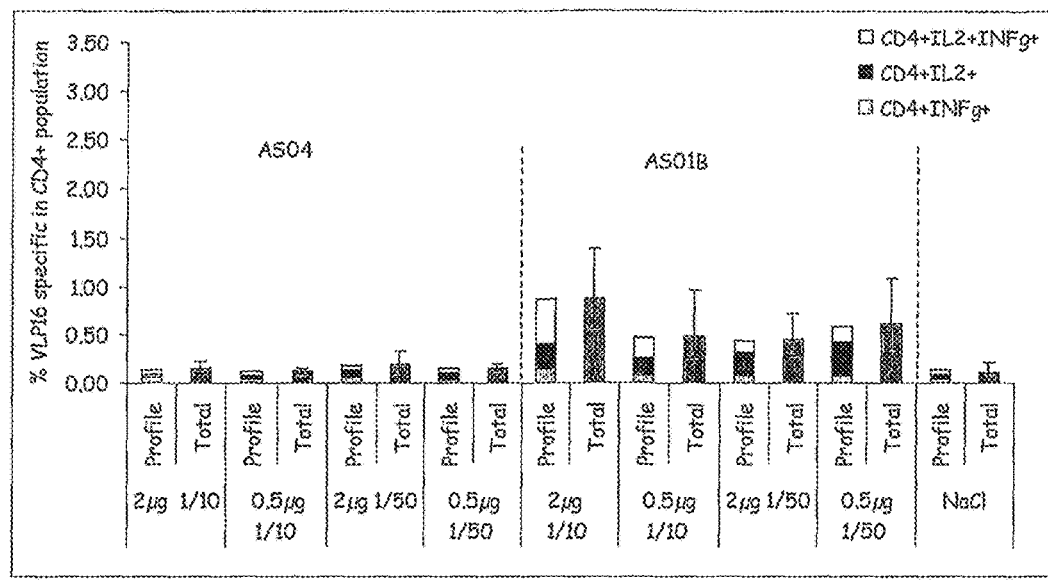
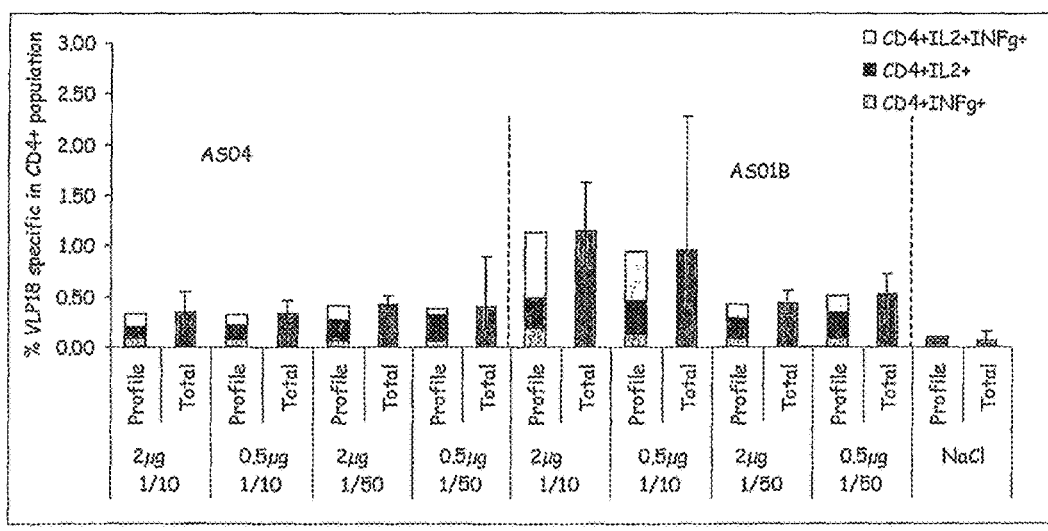

Figure 11:
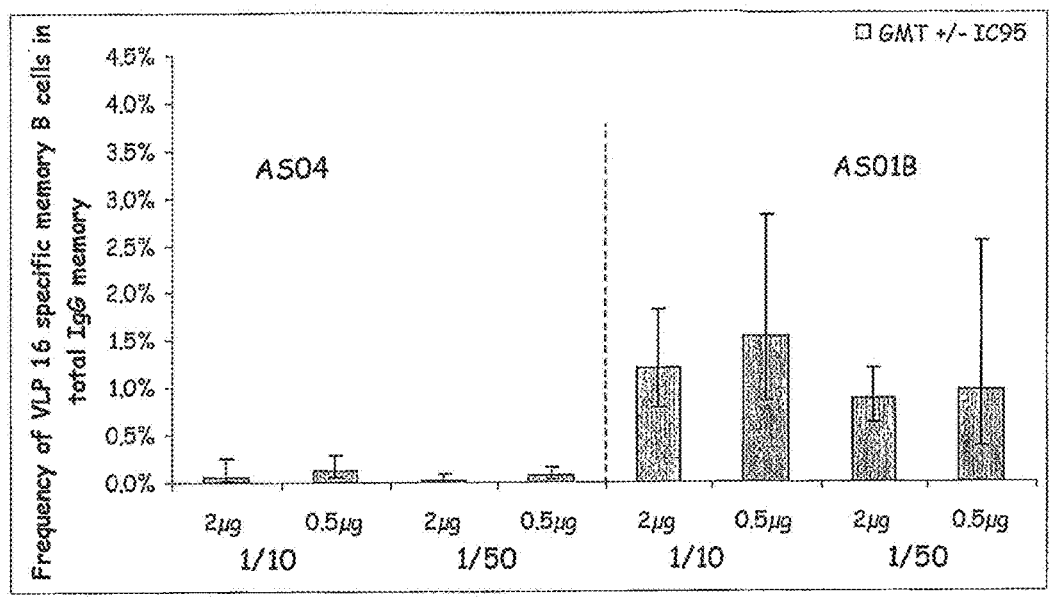
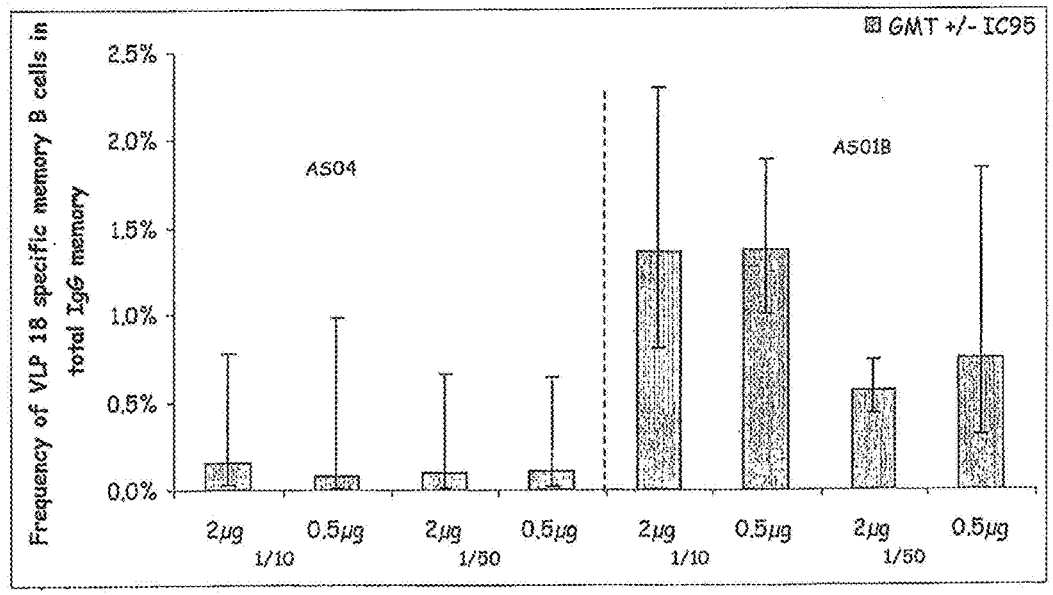

Figure 17:
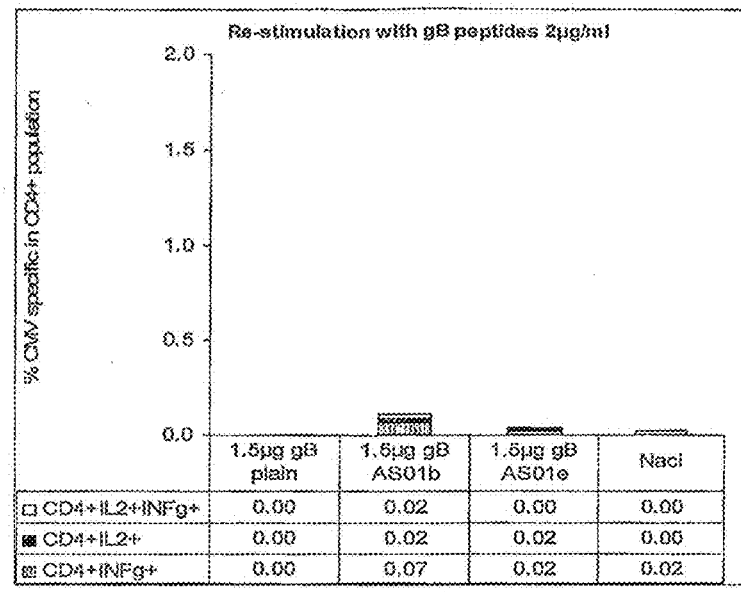
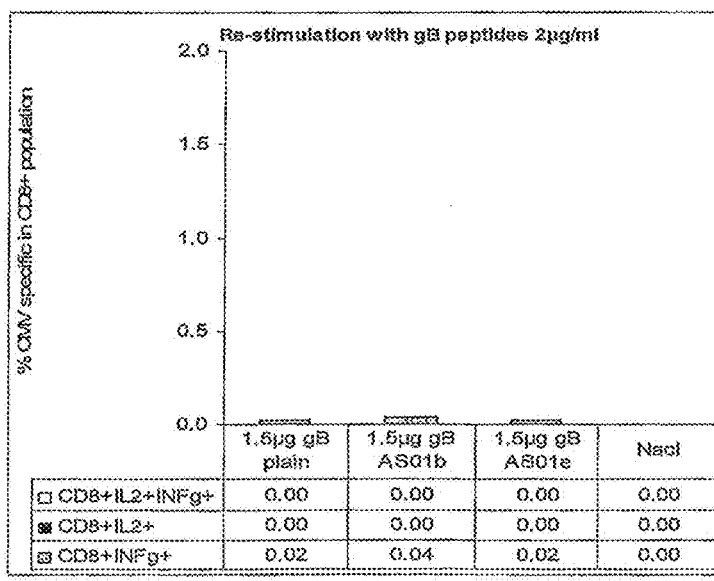

Figure 19:
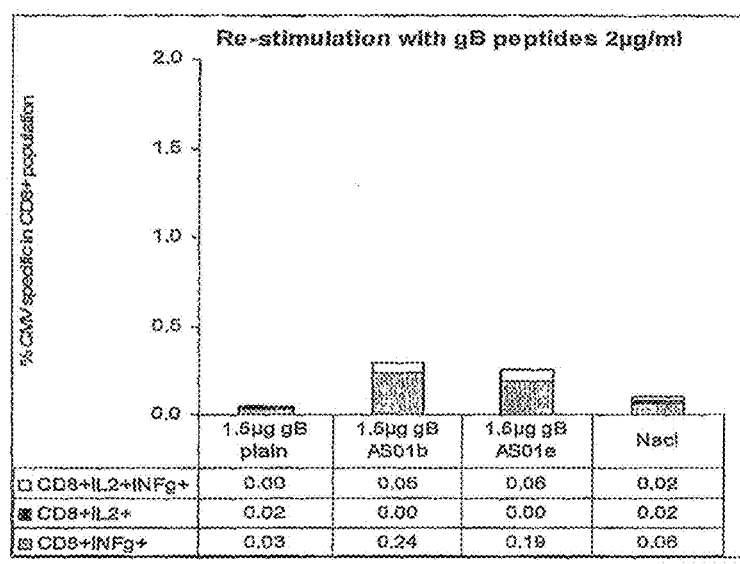
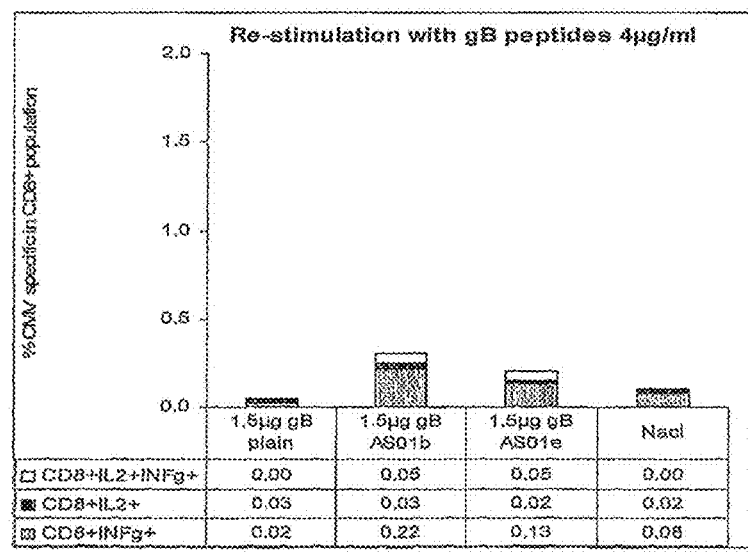

Figure 22:
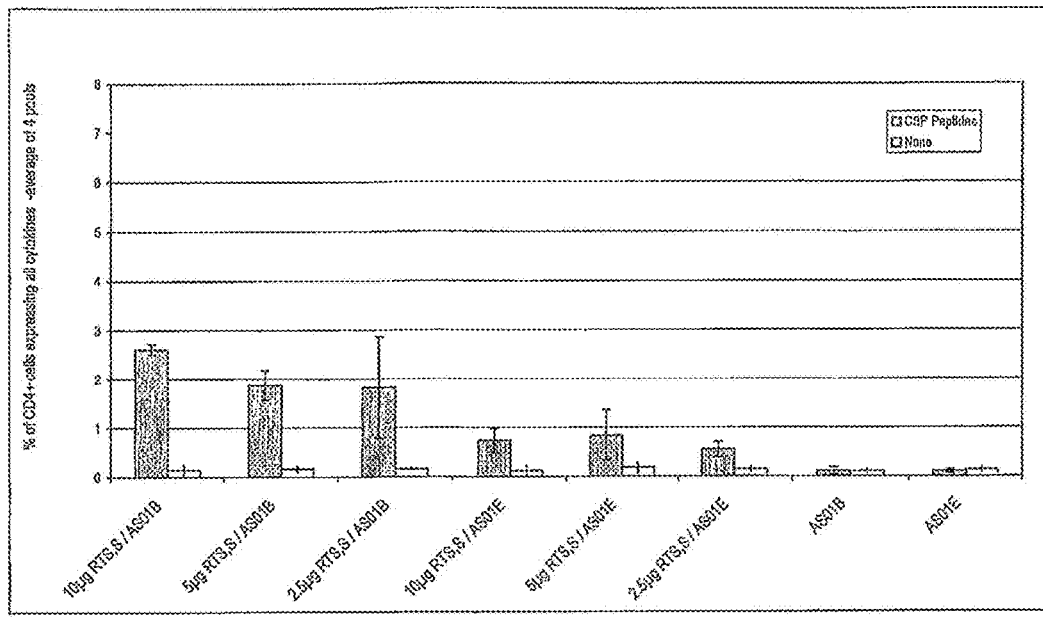
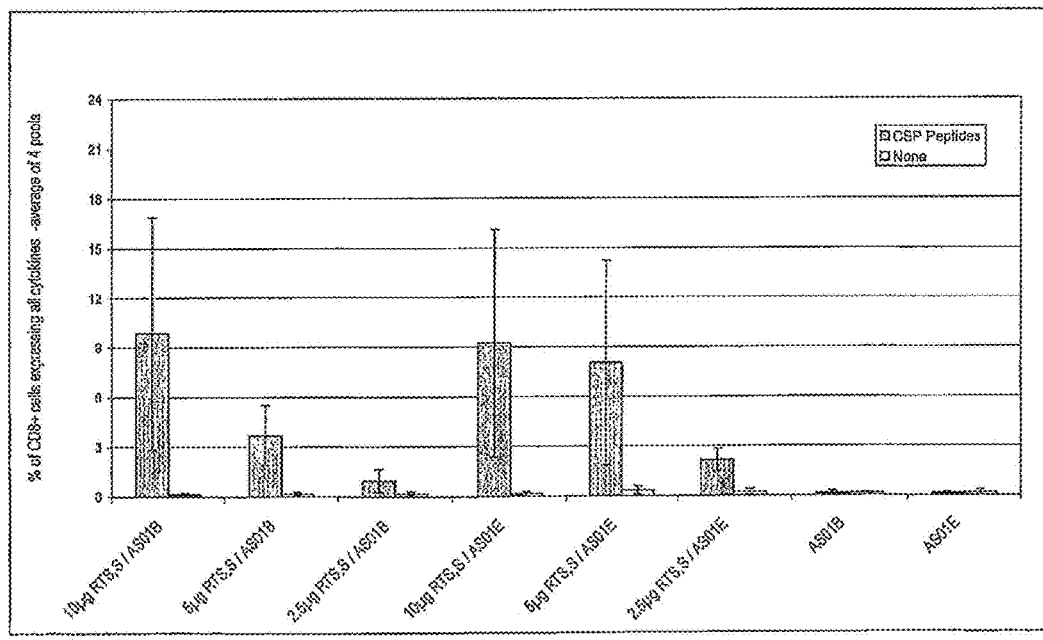

Figure 23:
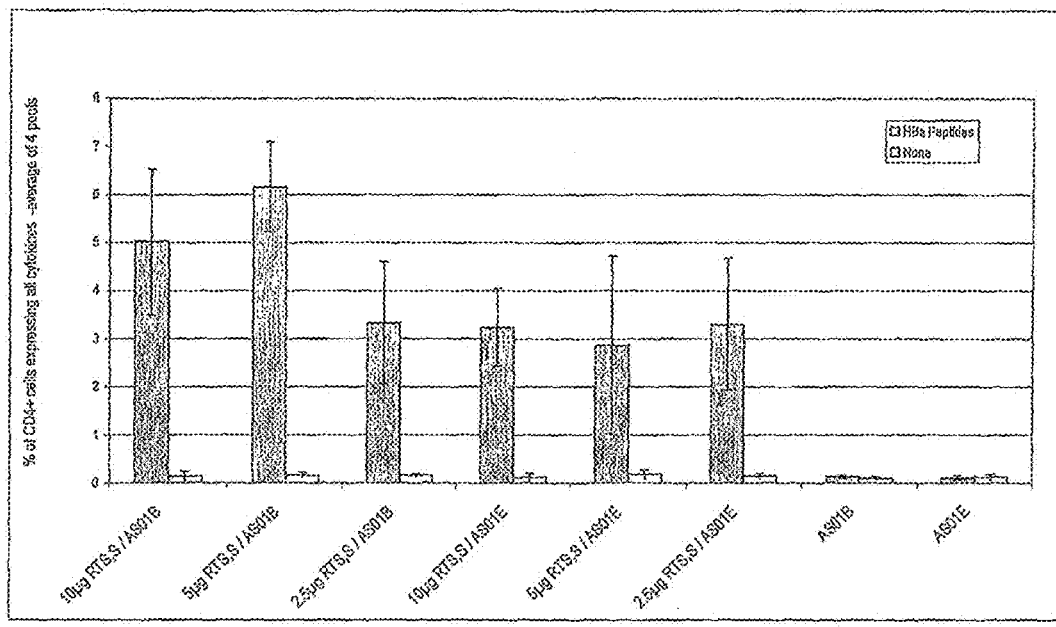
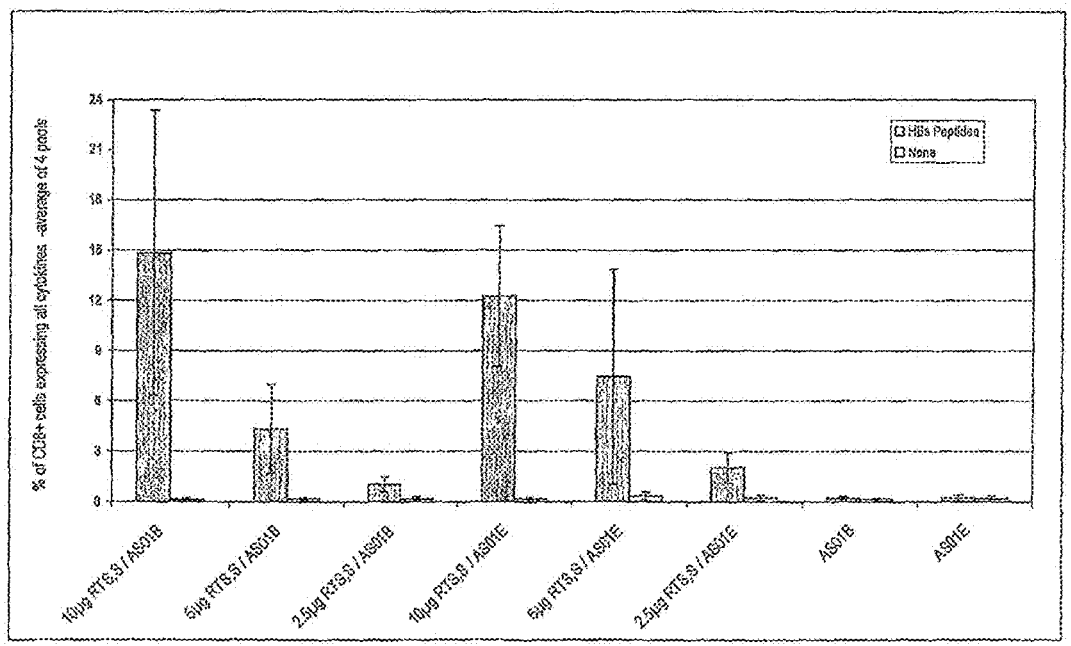

Figure 24:
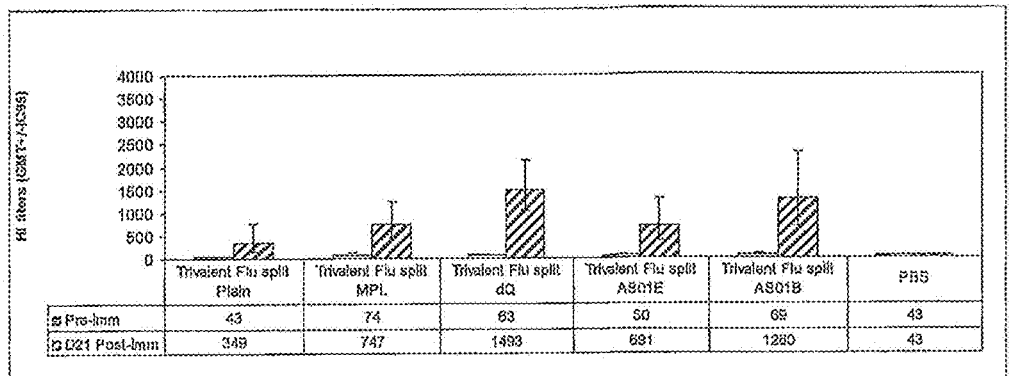
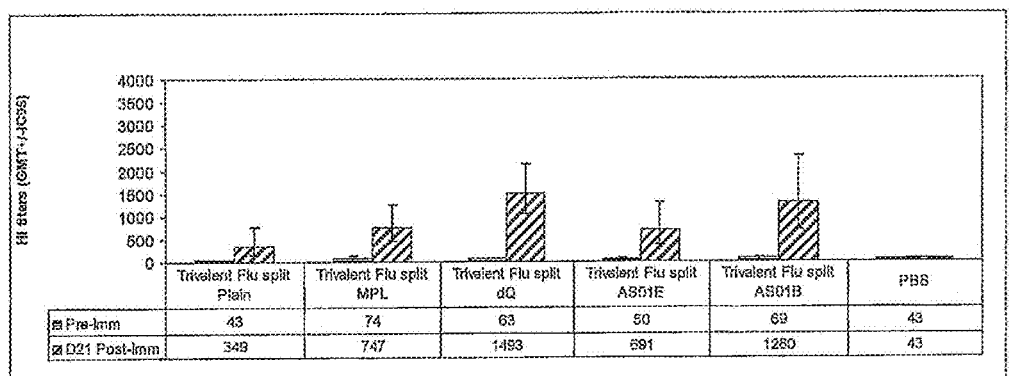
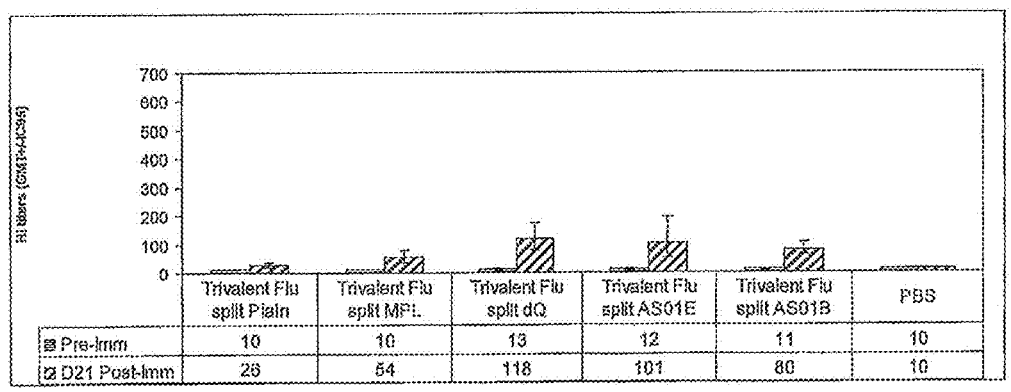

Figure 26: Preclinical results in mice comparing VZV gE vaccines adjuvant with AS01B or AS01E.
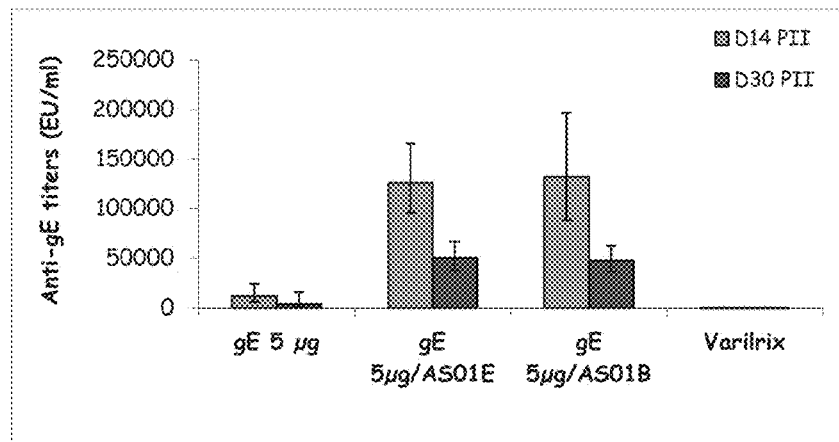
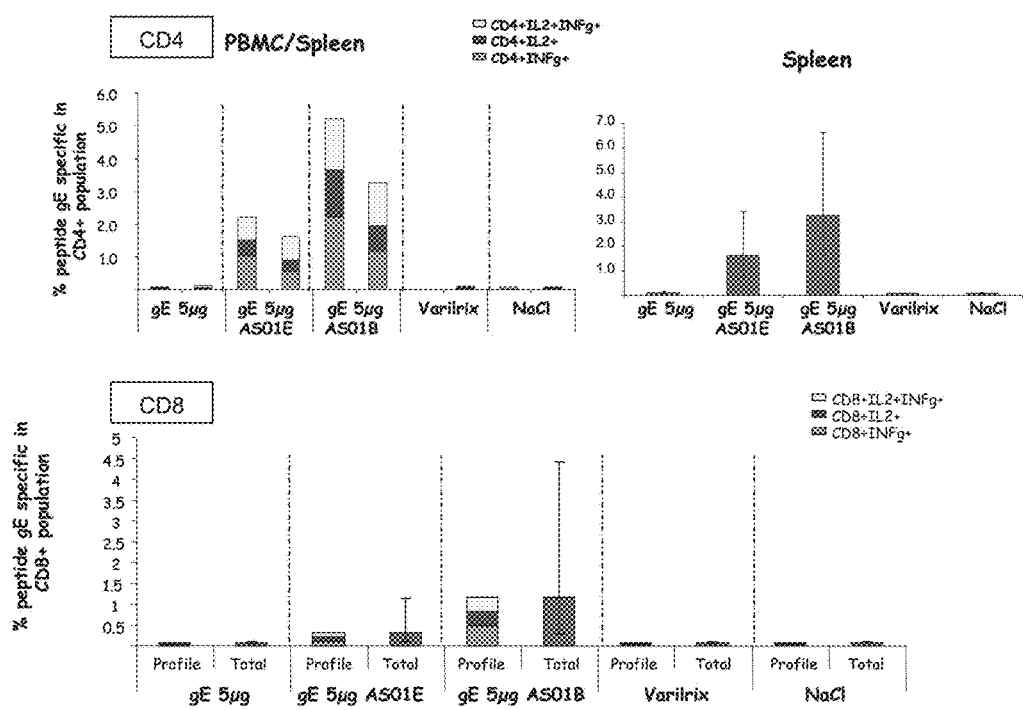

Figure 28:
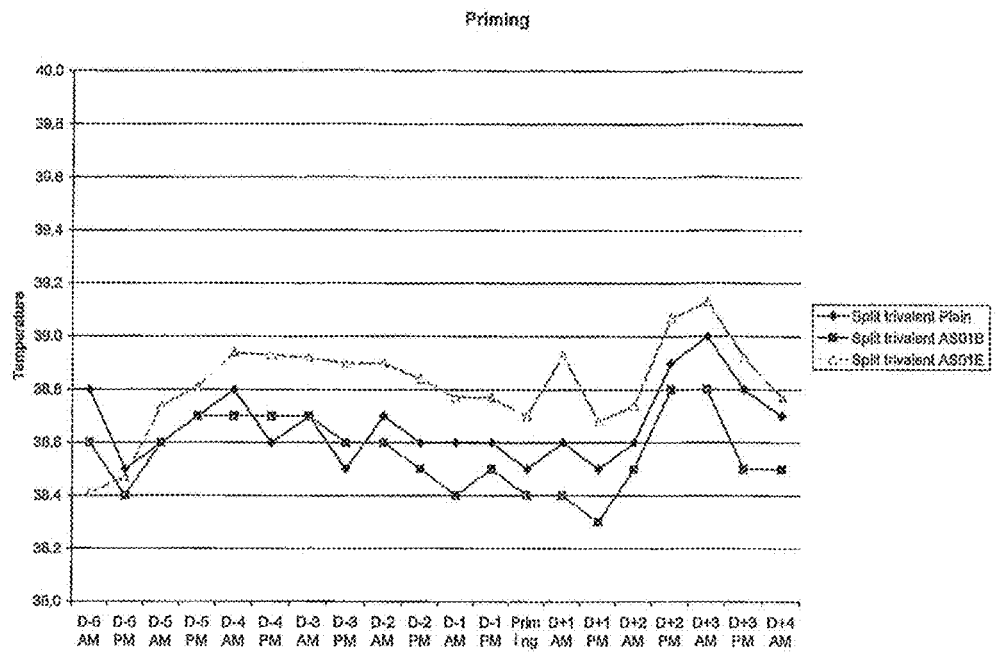
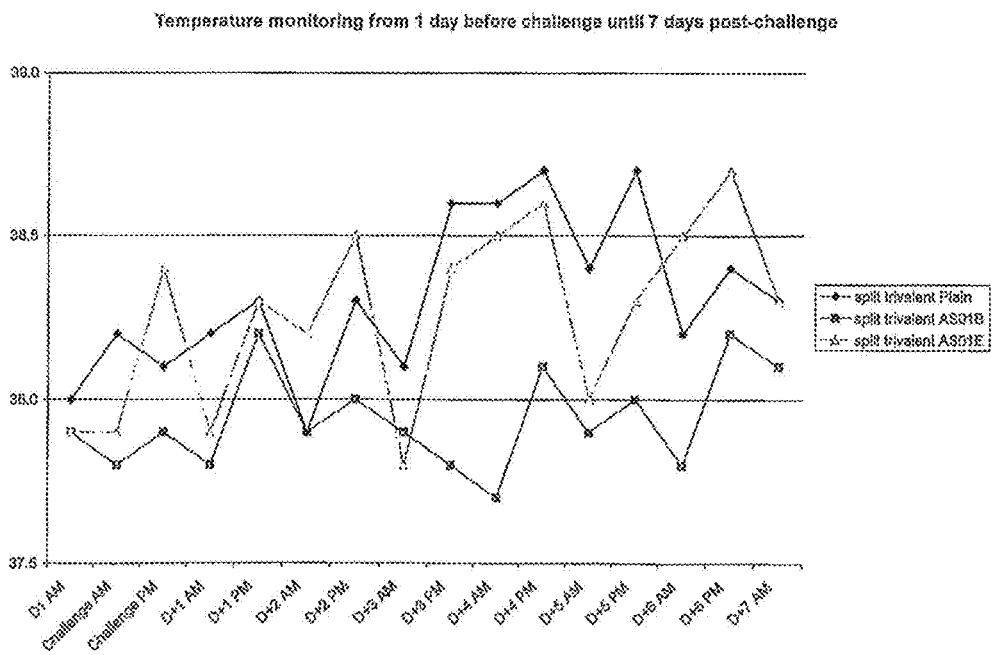

Figure 29:
Anti-A/New Caledonia/20/99 H1N1 - H1 titers
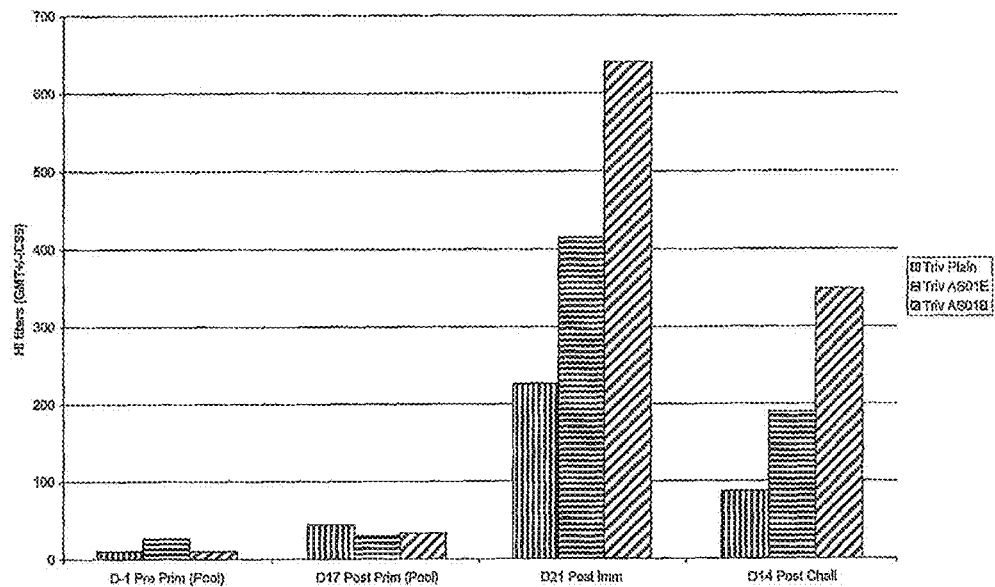
Anti-A/Wyoming/3/2003 H3N2 - H1 titers
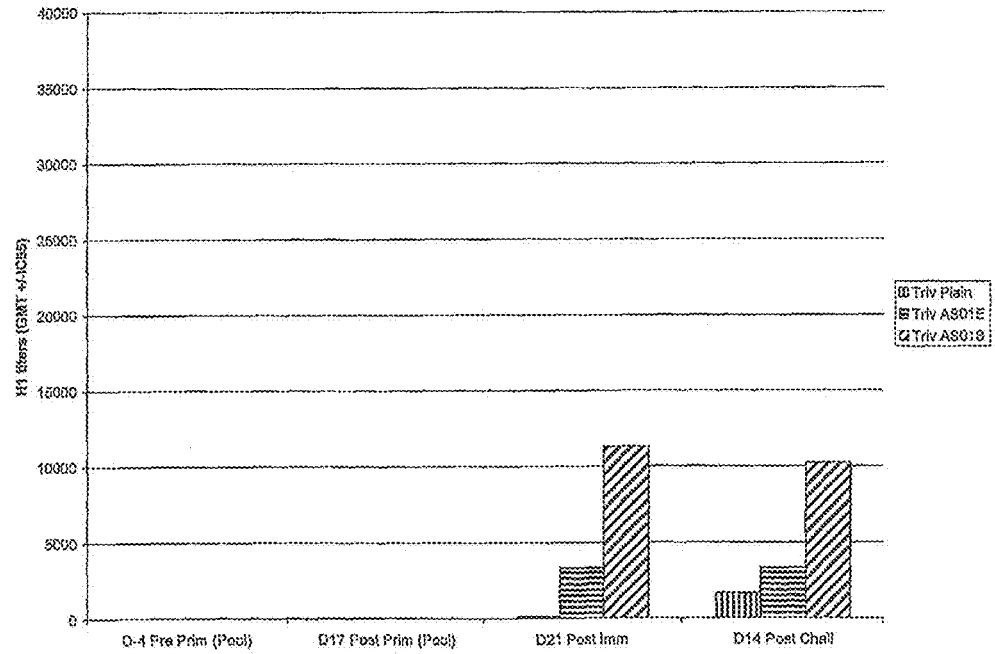

Figure 30:
Anti-B/Jiangsu/10/2003 - HI titers
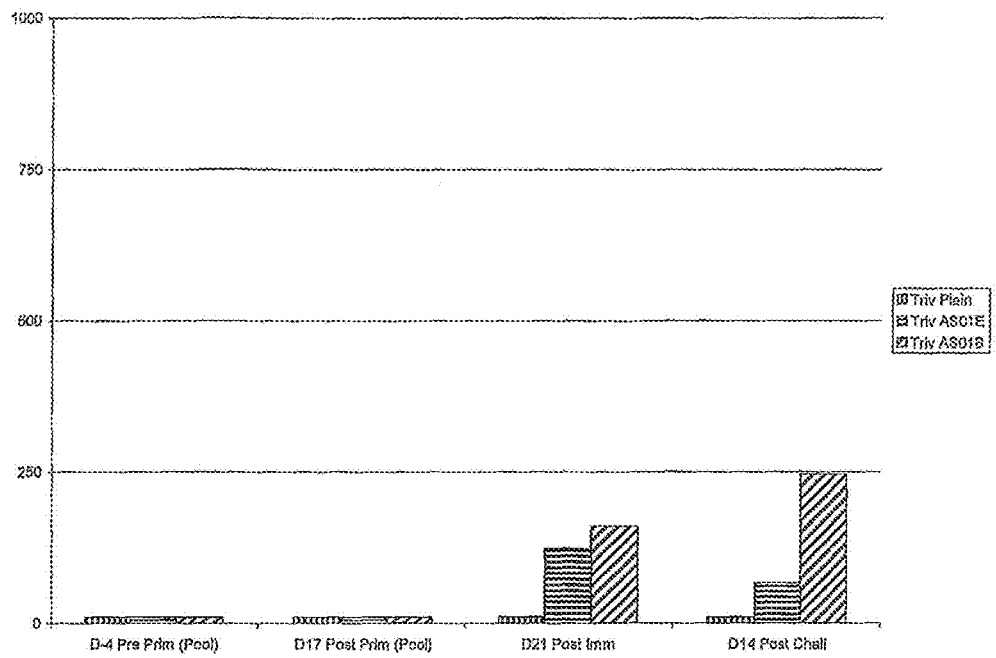
Anti-A/New York/55/2004 H3N2 HI titers
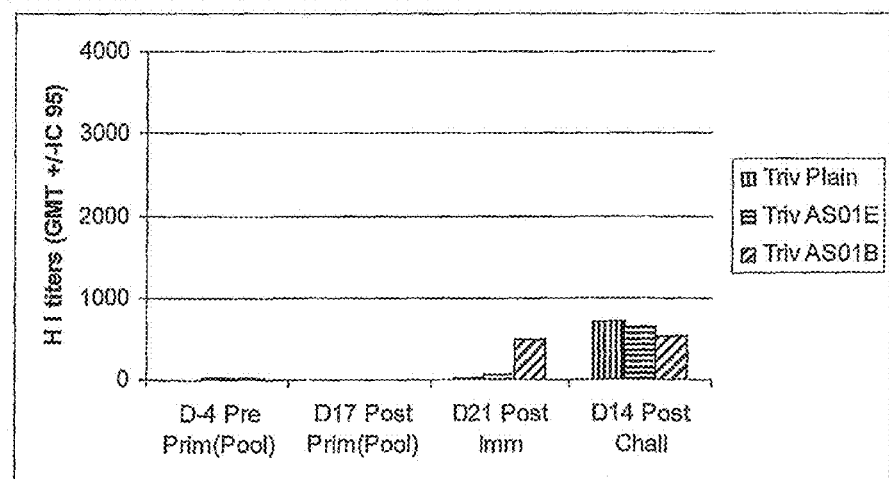

SEQUENCE LISTING

```
<160> NUMBER OF SEQ ID NOS: 1

<210> SEQ ID NO 1
<211> LENGTH: 12
<212> TYPE: PRT
<213> ORGANISM: HSV

<400> SEQUENCE: 1

Pro Glu Asp Ser Ala Leu Leu Glu Asp Pro Glu Asp
1               5                   10
```

VACCINE COMPOSITIONS COMPRISING A SAPONIN ADJUVANT

CROSS-REFERENCE TO RELATED APPLICATION

This is a United States Continuation Application which claims the priority of U.S. application Ser. No. 13/020,045 filed Feb. 3, 2011, now pending, which is a United States Continuation Application claiming priority to U.S. application Ser. No. 12/096,838 filed Jun. 10, 2008, now abandoned, which was filed pursuant to 35 USC 371 as a United States National Phase Application of International Patent Application Serial No. PCT/GB2006/004634 filed on Dec. 12, 2006, which claims the priority of 0525321.6 filed on Dec. 13, 2005, 0609902.2 filed on May 18, 2006, 0620336.8 filed on Oct. 12, 2006, 0620337.6 filed on Oct. 12, 2006 in the United Kingdom which are incorporated herein in their entirety.

STATEMENT REGARDING SEQUENCE LISTING

Applicants respectfully request that the sequence listing provided in electronic form (as .txt file) in lieu of a paper copy, be incorporated by reference into the specification. The name of the text file containing the sequence listing is VB61750C2_Sequence_Listing.txt. It is hereby stated that the content of the Sequence Listing does not include new matter.

FIELD OF THE INVENTION

The present invention relates to improved vaccine compositions, methods for making them, and their use in medicine. In particular the invention relates to adjuvanted vaccine compositions wherein the adjuvant is a liposomal formulation, comprising a saponin and a lipopolysaccharide. The present invention further relates to influenza vaccine formulations and vaccination regimes for immunizing against influenza disease.

BACKGROUND OF THE INVENTION

New compositions or vaccines with an improved immunogenicity are always needed. As one strategy, adjuvants have been used to try and improve the immune response raised to any given antigen.

Lipopolysaccharides (LPS) are the major surface molecule of, and occur exclusively in, the external leaflet of the outer membrane of gram-negative bacteria. LPS impede destruction of bacteria by serum complements and phagocytic cells, and are involved in adherence for colonisation. LPS are a group of structurally related complex molecules of approximately 10,000 Daltons in size and consist of three covalently linked regions:
  (i) an O-specific polysaccharide chain (O-antigen) at the outer region
  (ii) a core oligosaccharide central region
  (iii) lipid A—the innermost region which serves as the hydrophobic anchor, it comprises glucosamine disaccharide units which carry long chain fatty acids.

The biological activities of LPS, such as lethal toxicity, pyrogenicity and adjuvanticity, have been shown to be related to the lipid A moiety. In contrast, immunogenicity is associated with the O-specific polysaccharide component (O-antigen). Both LPS and lipid A have long been known for their strong adjuvant effects, but the high toxicity of these molecules has precluded their use in vaccine formulations. Significant effort has therefore been made towards reducing the toxicity of LPS or lipid A while maintaining their adjuvanticity.

The *Salmonella minnesota* mutant R595 was isolated in 1966 from a culture of the parent (smooth) strain (Luderitz et al. 1966 *Ann. N. Y. Acad. Sci.* 133:349-374). The colonies selected were screened for their susceptibility to lysis by a panel of phages, and only those colonies that displayed a narrow range of sensitivity (susceptible to one or two phages only) were selected for further study. This effort led to the isolation of a deep rough mutant strain which is defective in LPS biosynthesis and referred to as *S. minnesota* R595.

In comparison to other LPS, those produced by the mutant *S. minnesota* R595 have a relatively simple structure.
  (i) they contain no O-specific region—a characteristic which is responsible for the shift from the wild type smooth phenotype to the mutant rough phenotype and results in a loss of virulence
  (ii) the core region is very short—this characteristic increases the strain susceptibility to a variety of chemicals
  (iii) the lipid A moiety is highly acylated with up to 7 fatty acids.

4'-monophosporyl lipid A (MPL), which may be obtained by the acid hydrolysis of LPS extracted from a deep rough mutant strain of gram-negative bacteria, retains the adjuvant properties of LPS while demonstrating a toxicity which is reduced by a factor of more than 1000 (as measured by lethal dose in chick embryo eggs) (Johnson et al. 1987 Rev. Infect. Dis. 9 Suppl:S512-S516). LPS is typically refluxed in mineral acid solutions of moderate strength (e.g. 0.1 M HCl) for a period of approximately 30 minutes. This process results in dephosphorylation at the 1 position, and decarbohydration at the 6' position, yielding MPL.

3-O-deacylated monophosphoryl lipid A (3D-MPL), which may be obtained by mild alkaline hydrolysis of MPL, has a further reduced toxicity while again maintaining adjuvanticity, see U.S. Pat. No. 4,912,094 (Ribi Immunochemicals). Alkaline hydrolysis is typically performed in organic solvent, such as a mixture of chloroform/methanol, by saturation with an aqueous solution of weak base, such as 0.5 M sodium carbonate at pH 10.5.

Further information on the preparation of 3D-MPL is available in, for example, U.S. Pat. No. 4,912,094 and WO02/078637 (Corixa Corporation).

*Quillaja* saponins are a mixture of triterpene glycosides extracted from the bark of the tree *Quillaja saponaria*. Crude saponins have been extensively employed as veterinary adjuvants. Quil-A is a partially purified aqueous extract of the *Quillaja* saponin material. QS21 is a Hplc purified non toxic fraction of Quil A and its method of its production is disclosed (as QA21) in U.S. Pat. No. 5,057,540.

By way of example, influenza vaccines and vaccines against human papilloma virus (HPV) have been developed with adjuvants.

Influenza viruses are one of the most ubiquitous viruses present in the world, affecting both humans and livestock. Influenza results in an economic burden, morbidity and even mortality, which are significant.

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of host-derived lipid material. Influenza virus comprises two surface antigens, glycoproteins neuraminidase (NA) and haemagglutinin (HA), which appear as spikes, 10 to 12 nm long, at the surface of the particles. It is these surface proteins, particularly the haemagglutinin that determine the antigenic specificity of the influenza subtypes.

These surface antigens progressively, sometimes rapidly, undergo some changes leading to the antigenic variations in influenza. These antigenic changes, called 'drifts' and 'shifts' are unpredictable and may have a dramatic impact from an immunological point of view as they eventually lead to the emergence of new influenza strains that enable the virus to escape the immune system causing the well known, almost annual, epidemics.

The influenza virus strains to be incorporated into influenza vaccine each season are determined by the World Health Organisation in collaboration with national health authorities and vaccine manufacturers.

HA is the most important antigen in defining the serological specificity of the different influenza strains. This 75-80 kD protein contains numerous antigenic determinants, several of which are in regions that undergo sequence changes in different strains (strain-specific determinants) and others in regions which are common to many HA molecules (common to determinants).

Influenza viruses cause epidemics almost every winter, with infection rates for type A or B virus as high as 40% over a six-week period. Influenza infection results in various disease states, from a sub-clinical infection through mild upper respiratory infection to a severe viral pneumonia. Typical influenza epidemics cause increases in incidence of pneumonia and lower respiratory disease as witnessed by increased rates of hospitalization or mortality. The severity of the disease is primarily determined by the age of the host, his immune status and the site of infection.

Elderly people, 65 years old and over, are especially vulnerable, accounting for 80-90% of all influenza-related deaths in developed countries. Individuals with underlying chronic diseases are also most likely to experience such complications. Young infants also may suffer severe disease. These groups in particular therefore need to be protected. Besides these 'at risk'-groups, the health authorities are also recommending to vaccinate healthy adults who are in contact with elderly persons.

Vaccination plays a critical role in controlling annual influenza epidemics. Currently available influenza vaccines are either inactivated or live attenuated influenza vaccine. Inactivated flu vaccines are composed of three possible forms of antigen preparation: inactivated whole virus, subvirions where purified virus particles are disrupted with detergents or other reagents to solubilise the lipid envelope (so-called "split" vaccine) or purified HA and NA (subunit vaccine). These inactivated vaccines are given intramuscularly (i.m.) or intranasaly (i.n.).

Influenza vaccines, of all kinds, are usually trivalent vaccines. They generally contain antigens derived from two influenza A virus strains and one influenza B strain. A standard 0.5 ml injectable dose in most cases contains 15 µg of haemagglutinin antigen component from each strain, as measured by single radial immunodiffusion (SRD) (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and immunoelectrophoresis techniques for the assay of haemagglutinin antigen of influenza virus. J. Biol. Stand. 9 (1981) 317-330).

Influenza vaccines currently available are considered safe in all age groups (De Donato et al. 1999, Vaccine, 17, 3094-3101). However, there is little evidence that current influenza vaccines work in small children under two years of age. Furthermore, reported rates of vaccine efficacy for prevention of typical confirmed influenza illness are 23-72% for the elderly, which are significantly lower than the 60-90% efficacy rates reported for younger adults (Govaert, 1994, J. Am. Med. Assoc., 21, 166-1665; Gross, 1995, Ann Intern. Med. 123, 523-527). The effectiveness of an influenza vaccine has been shown to correlate with serum titres of hemagglutination inhibition (HI) antibodies to the viral strain, and several studies have found that older adults exhibit lower HI titres after influenza immunisation than do younger adults (Murasko, 2002, Experimental gerontology, 37, 427-439).

New vaccines with an improved immunogenicity are therefore still needed. Formulation of vaccine antigen with potent adjuvants is a possible approach for enhancing immune responses to subvirion antigens.

A sub-unit influenza vaccine adjuvanted with the adjuvant MF59, in the form of an oil-in-water emulsion is commercially available, and has demonstrated its ability to induce a higher antibody titer than that obtained with the non-adjuvanted sub-unit vaccine (De Donato et al. 1999, Vaccine, 17, 3094-3101). However, in a later publication, the same vaccine has not demonstrated its improved profile compared to a non-adjuvanted split vaccine (Puig-Barbera et al., 2004, Vaccine 23, 283-289).

By way of background, during inter-pandemic periods, influenza viruses circulate that are related to those from the preceding epidemic. The viruses spread among people with varying levels of immunity from infections earlier in life. Such circulation, over a period of usually 2-3 years, promotes the selection of new strains that have changed enough to cause an epidemic again among the general population; this process is termed 'antigenic drift'. 'Drift variants' may have different impacts in different communities, regions, countries or continents in any one year, although over several years their overall impact is often similar. In other words, an influenza pandemics occurs when a new influenza virus appears against which the human population has no immunity. Typical influenza epidemics cause increases in incidence of pneumonia and lower respiratory disease as witnessed by increased rates of hospitalisation or mortality. The elderly or those with underlying chronic diseases are most likely to experience such complications, but young infants also may suffer severe disease.

At unpredictable intervals, novel influenza viruses emerge with a key surface antigen, the haemagglutinin, of a totally different subtype from strains circulating the season before. Here, the resulting antigens can vary from 20% to 50% from the corresponding protein of strains that were previously circulating in humans. This can result in virus escaping 'herd immunity' and establishing pandemics. This phenomenon is called 'antigenic shift'. It is thought that at least in the past pandemics have occurred when an influenza virus from a different species, such as an avian or a porcine influenza virus, has crossed the species barrier. If such viruses have the potential to spread from person to person, they may spread worldwide within a few months to a year, resulting in a pandemic. For example, in 1957 (Asian Flu pandemic), viruses of the H2N2 subtype replaced H1N1 viruses that had been circulating in the human population since at least 1918 when the virus was first isolated. The H2 HA and N2 NA underwent antigenic drift between 1957 and 1968 until the HA was replaced in 1968 (Hong-Kong Flu pandemic) by the emergence of the H3N2 influenza subtype, after which the N2 NA continued to drift along with the H3 HA (Nakajima et al., 1991, Epidemiol. Infect. 106, 383-395).

The features of an influenza virus strain that give it the potential to cause a pandemic outbreak are: it contains a new haemagglutinin compared to the haemagglutinin in the currently circulating strains, which may or not be accompanied by a change in neuraminidase subtype; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9, H7 or H6 which are found in birds. In either case the majority, or at least a large proportion of, or even the entire population has not previously encountered the antigen and is immunologically naïve to it.

Papillomaviruses are small DNA tumour viruses, which are highly species specific. So far, over 100 individual human papillomavirus (HPV) genotypes have been described. HPVs are generally specific either for the skin (e.g. HPV-1 and -2) or mucosal surfaces (e.g. HPV-6 and -11) and usually cause benign tumours (warts) that persist for several months or years. Such benign tumours may be distressing for the individuals concerned but tend not to be life threatening, with a few exceptions.

Some HPVs are also associated with cancers. The strongest positive association between an HPV and human cancer is that which exists between HPV-16 and HPV-18 and cervical carcinoma. Cervical cancer is the most common malignancy in developing countries, with about 500,000 new cases occurring in the world each year. It is now technically feasible to actively combat primary HPV-16 infections, and even established HPV-16-containing cancers, using vaccines. For a review on the prospects for prophylactic and therapeutic vaccination against HPV-16 see Cason J., Clin. Immunother. 1994; 1(4) 293-306 and Hagenesee M. E., Infections in Medicine 1997 14(7) 555-556, 559-564.

Although minor variations do occur, all HPV genomes described have at least eight early genes, E1 to E8 and two late genes L1 and L2. In addition, an upstream regulatory region harbors the regulatory sequences which appear to control most transcriptional events of the HPV genome.

HPV L1 based vaccines are disclosed in WO94/00152, WO94/20137, WO93/02184 and WO94/05792. Such a vaccine can comprise the L1 antigen as a monomer, a capsomer or a virus like particle. Methods for the preparation of VLPs are well known in the art, and include VLP disassembly-reassembly approaches to provide enhanced homogeneity, for example as described in WO9913056 and U.S. Pat. No. 6,245,568. Such particles may additionally comprise L2 proteins. L2 based vaccines are described, for example, in WO93/00436. Other HPV vaccine approaches are based on the early proteins, such as E7 or fusion proteins such as L2-E7.

There is still a need for improved vaccines, especially in the case of influenza and in particular influenza pandemics and for the elderly population, or in the case of HPV vaccines.

Adjuvants containing combinations of lipopolysaccharide and *Quillaja* saponins have been disclosed previously, for example in EP0671948. This patent demonstrated a strong synergy when a lipopolysaccharide (3D-MPL) was combined with a *Quillaja* saponin (QS21). It has now been found that good adjuvant properties may be achieved with combinations of lipopolysaccharide and *quillaja* saponin as immunostimulants in an adjuvant composition even when the immunostimulants are present at low amounts in a human dose.

SUMMARY OF THE INVENTION

In first aspect of the present invention, there is provided an immunogenic composition comprising an antigen or antigenic preparation thereof, in combination with an adjuvant composition comprising an immunologically active saponin fraction derived from the bark of *Quillaja saponaria Molina* presented in the form of a liposome and a lipopolysaccharide.

In a second aspect of the present invention, there is provided an immunogenic composition comprising an influenza virus or antigenic preparation thereof, in combination with a saponin adjuvant presented in the form of a liposome. In a specific embodiment of this aspect, the immunogenic composition further comprises a Lipid A derivative, such as 3D-MPL.

Suitably the saponin adjuvant in the form of a liposome according to the invention comprises an active fraction of the saponin derived from the bark of *Quillaja saponaria Molina*, such as QS21, and a sterol, such as cholesterol, in a ratio saponin:sterol from 1:1 to 1:100 w/w.

In particular, said immunogenic composition comprises an antigen with a CD4 T cell epitope. Alternatively, said immunogenic composition comprises an antigen with a B cell epitope.

The invention also relates to the use of an influenza virus or antigenic preparation thereof, and an adjuvant comprising an immunologically active saponin fraction derived from the bark of *Quillaja saponaria Molina* presented in the form of a liposome and a lipopolysaccharide in the manufacture of an immunogenic composition for the prevention of influenza virus infection and/or disease.

The invention also relates to the use of a human papilloma virus antigen or antigens or antigenic preparation thereof, and an adjuvant comprising an immunologically active saponin fraction derived from the bark of *Quillaja saponaria Molina* presented in the form of a liposome and a lipopolysaccharide in the manufacture of an immunogenic composition for the prevention of human papilloma virus infection and/or disease.

The invention also relates to the use of a Cytomegalovirus antigen or antigens or antigenic preparation thereof, and an adjuvant comprising an immunologically active saponin fraction derived from the bark of *Quillaja saponaria Molina* presented in the form of a liposome and a lipopolysaccharide in the manufacture of an immunogenic composition for the prevention of Cytomegalovirus infection and/or disease.

The invention also relates to the use of a *Streptococcus pneumoanie* antigen or antigens or antigenic preparation thereof, and an adjuvant comprising an immunologically active saponin fraction derived from the bark of *Quillaja saponaria Molina* presented in the form of a liposome and a lipopolysaccharide defined in the manufacture of an immunogenic composition for the prevention of *Streptococcus pneumonaie* infection and/or disease.

The invention also relates to the use of a *Plasmodium falciparum* antigen or antigens or antigenic preparation thereof, and an adjuvant comprising an immunologically active saponin fraction derived from the bark of *Quillaja saponaria Molina* presented in the form of a liposome and a lipopolysaccharide in the manufacture of an immunogenic composition for the prevention of *Plasmodium falciparum* infection and/or malarial disease.

The invention also relates to the use of a Varicella Zoster virus antigen or antigens or antigenic preparation thereof, and an adjuvant comprising an immunologically active saponin fraction derived from the bark of *Quillaja saponaria Molina* presented in the form of a liposome and a lipopolysaccharide in the manufacture of an immunogenic composition for the prevention of Varicella Zoster virus infection and/or disease.

In another aspect there is provided the use of (a) an antigen or antigenic preparation thereof, and (b) an adjuvant as hereinabove defined in the manufacture of an immunogenic composition for inducing, in a human, at least one, or at least two, or all of the following: (i) an improved CD4 T-cell immune response against said antigen or antigenic preparation thereof, (ii) an improved humoral immune response against said antigen or antigenic preparation thereof, (iii) an improved B-memory cell response against said antigen or antigenic preparation thereof.

In particular said antigen is an influenza virus, HPV, Cytomegalovirus (CMV), Varicella zoster virus (VZV), *Streptococcus pneumoniae* or malaria antigen or antigenic preparation thereof, and said human is an immuno-compromised individual or population, such as a high risk adult, an elderly adult or an infant. In a specific embodiment, there is provided the use of an antigen or antigenic preparation thereof and an adjuvant as herein defined in the preparation of an immunogenic composition for vaccination of a human, in particular a human elderly adult, against the pathogen from which the antigen in the immunogenic composition is derived. Specifically said antigen is an influenza virus, human papilloma virus, Cytomegalovirus,Varicella Zoster virus, *Streptococcus pneumoniae*, *Plasmodium parasite*, antigen or antigens or antigenic preparation thereof.

There is also provided a method of vaccination comprising delivery of an antigen or antigenic composition, in particular an influenza virus or HPV, Cytomegalovirus, Varicella Zoster virus, *Streptococcus pneumoniae*, *Plasmodium parasite*, or antigenic preparation thereof and an adjuvant as hereinabove defined to an individual or population in need thereof.

In a specific embodiment, the immunogenic composition is capable of inducing an improved CD4 T-cell immune response against said antigen or antigenic preparation thereof, and in particular is further capable of inducing either a humoral immune response or an improved B-memory cell response or both, compared to that obtained with the un-adjuvanted antigen or antigenic composition. Specifically said CD4 T-cell immune response involves the induction of a cross-reactive CD4 T helper response. Specifically said humoral immune response involves the induction of a cross-reactive humoral immune response.

In a further embodiment, there is provided a method or use as hereinabove defined, for protection against infection or disease caused by a pathogen which is a variant of the pathogen from which the antigen in the immunogenic composition is derived. In another embodiment, there is provided a method or use as hereinabove defined for protection against infections or disease caused by a pathogen which comprises an antigen which is a variant of that antigen in the immunogenic composition. In a specific embodiment, there is provided the use of an antigen, in particular an influenza or HPV, or antigenic preparation thereof in the manufacture of an immunogenic composition for revaccination of humans previously vaccinated with an immunogenic composition comprising an antigen, in particular an influenza or HPV or antigenic preparation thereof, in combination with an adjuvant as herein described.

In a specific embodiment, the composition used for the revaccination may additionally contain an adjuvant. In another specific embodiment, the immunogenic composition for revaccination contains an antigen which shares common CD4 T-cell epitopes with an antigen or antigenic composition used for a previous vaccination. Specifically, the immunogenic composition for revaccination contains an influenza virus or antigenic preparation thereof which shares common CD4 T-cell epitopes with the influenza virus or virus antigenic preparation thereof used for the first vaccination.

In one aspect, the revaccination is made in subjects who have been vaccinated the previous season against influenza. Typically revaccination is made at least 6 months after the first vaccination, preferably 8 to 14 months after, more preferably at around 10 to 12 months after. In another aspect the revaccination is made in subjects who have been vaccinated with a composition comprising an influenza virus or antigenic preparation thereof wherein at least one strain is associated with a pandemic outbreak or has the potential to be associated with a pandemic outbreak.

In a further aspect of the present invention, there is provided the use of an influenza virus or antigenic preparation thereof from a first influenza strain in the manufacture of an immunogenic composition as herein defined for protection against influenza infections caused by a variant influenza strain.

The invention also relates to a method of vaccination comprising delivery of an influenza virus or antigenic preparation thereof and an adjuvant as herein defined.

In another aspect, there is provided a method of vaccination of an immuno-compromised human individual or population such as high risk adults or elderly, comprising administering an influenza immunogenic composition comprising an influenza virus or antigenic preparation thereof in combination with an adjuvant as herein defined.

In still another embodiment, the invention provides a method for revaccinating humans previously vaccinated with an influenza immunogenic composition comprising an influenza antigen or antigenic preparation thereof from at least one influenza virus strains in combination with an adjuvant as herein defined, said method comprising administering to said human an immunogenic composition comprising an influenza virus or antigenic preparation thereof, either adjuvanted or un-adjuvanted.

The invention also relates to a method for the preparation of an immunogenic composition comprising combining a saponin adjuvant in the form of a liposome with an influenza virus or antigenic preparation thereof, and optionally with 3D-MPL.

Other aspects and advantages of the present invention are described further in the following detailed description of the preferred embodiments thereof.

DESCRIPTION OF FIGURES

FIG. 2A-2D—Humoral response against various strains of influenza following immunization of ferrets with experimental formulations: Hemagglutination Inhibition Test (GMT+/−IC95) before and after heterologous priming (H1N1 A/Stockholm/24/90), after immunization (H1N1

A/New Caledonia/20/99, H3N2 A/Panama/2007/99 and B/Shangdong/7/97) and after heterologous challenge (H3N2 A/Wyoming/3/2003)

Figure 3:
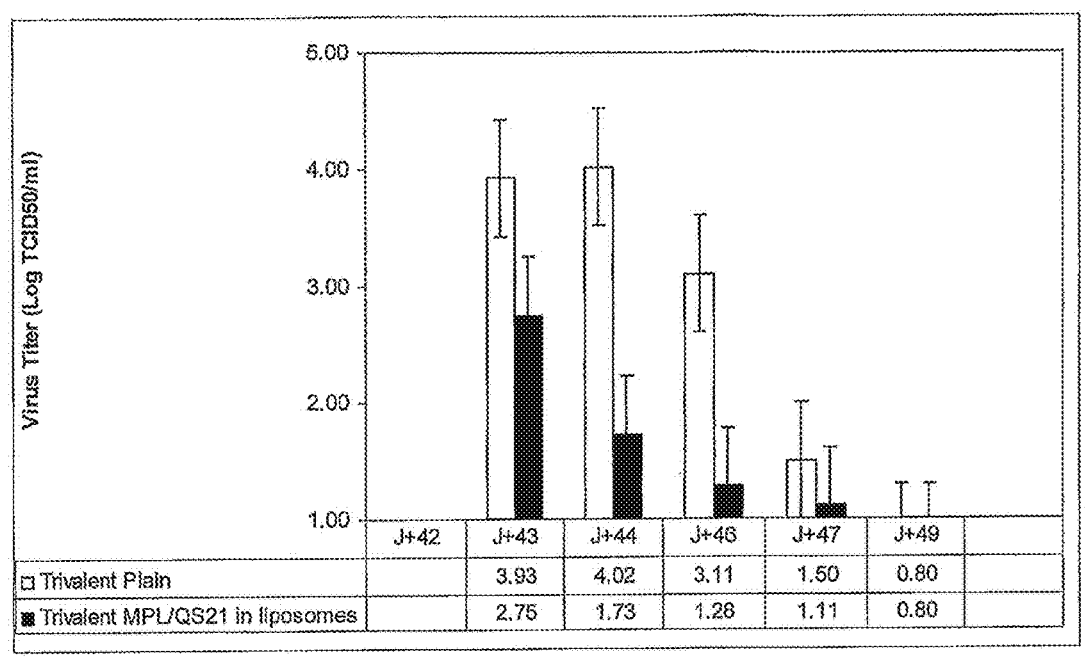

FIG. 3—Ferret study: Viral titration in nasal washes after challenge (Day 42)

Figure 4:
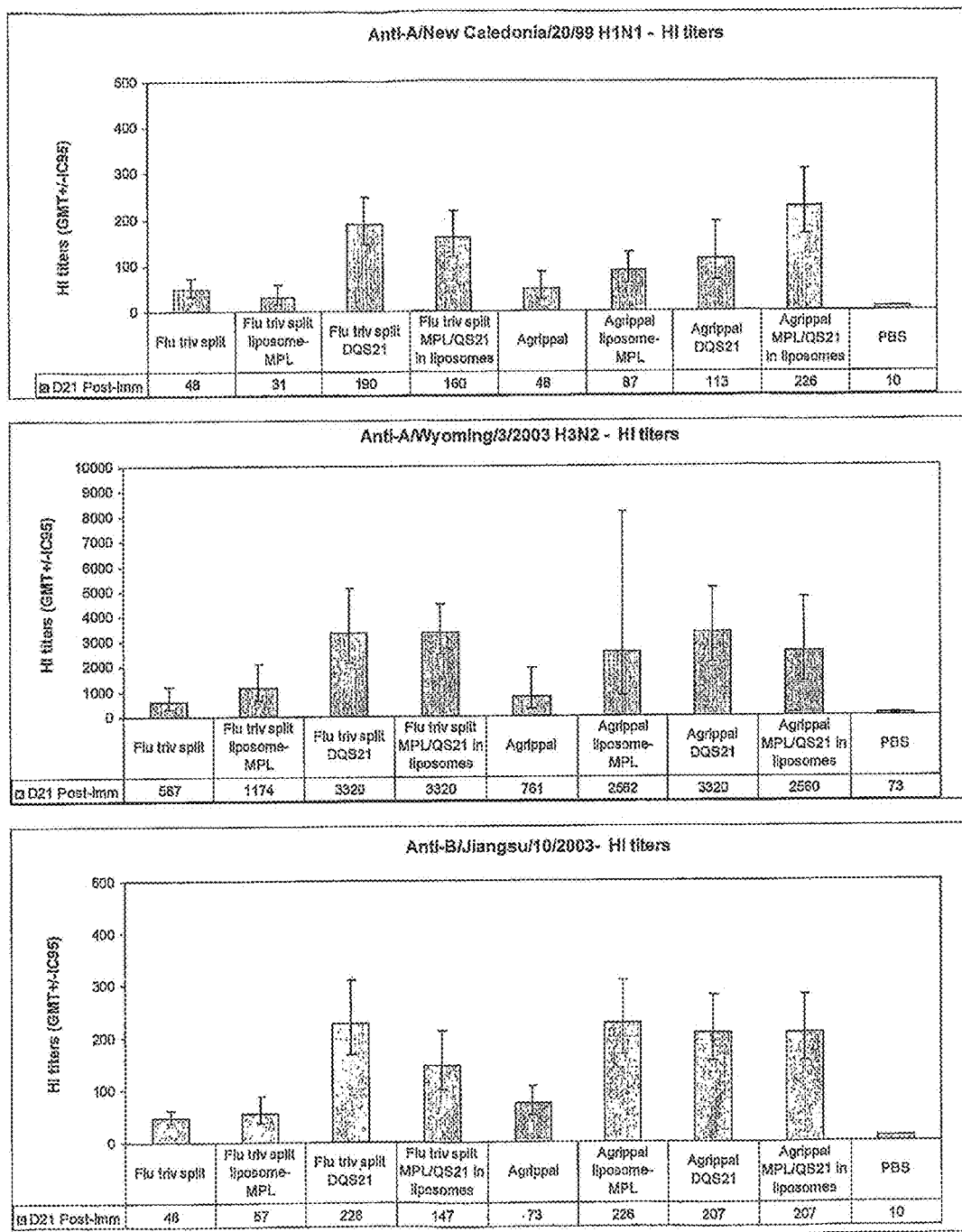

FIG. 4—Mice study: Humoral response against the three vaccine strains of influenza following immunization of mice with experimental formulations: Hemagglutination Inhibition Test (GMT+/−IC95) 21 days after immunization (H1N1 A/New Caledonia/20/99, H3N2 A/Wyoming/3/2003 and B/Jiangsu/10/2003).

FIG. 5—Mice study: Cell mediated immune response: Flu-specific CD4+ T cell responses on Day 7 Post-immunization.

FIG. 6—Mice study: CMI for CD4—Pooled strain (all double)—Day 0 and Day 21

FIG. 7—GMTs at days 0 and 21 for HI antibodies

Figure 8:
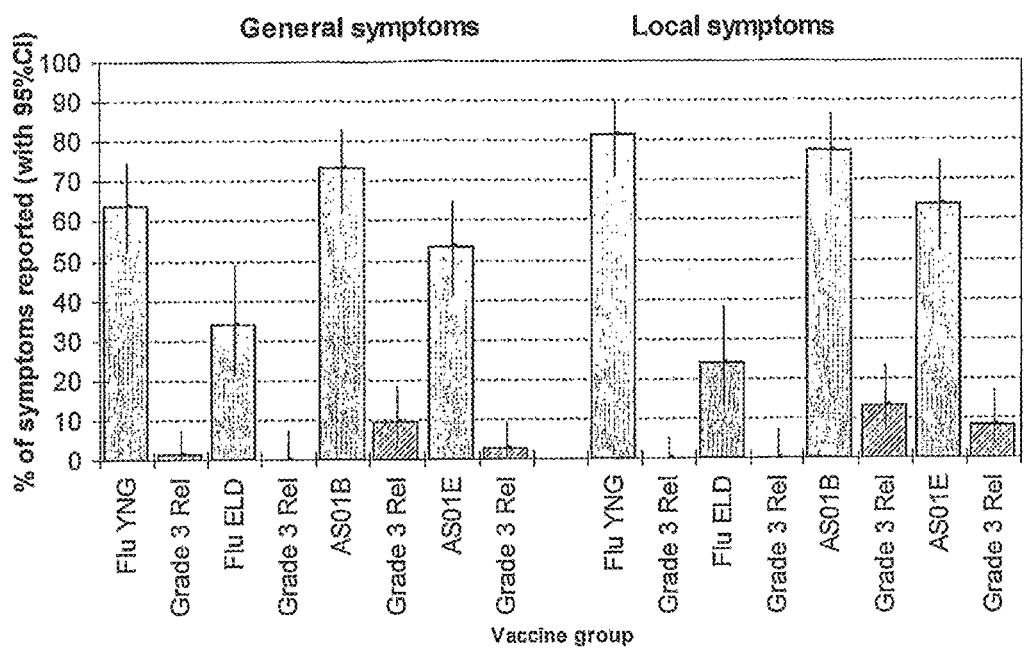

FIG. 8: Incidence of local and general symptoms in humans (Total and grade 3 related) reported during the 7-day follow up period following immunisation with adjuvanted influenza virus formulations, comparing adjuvants having two different concentrations of immunostimulants.

Figure 9:
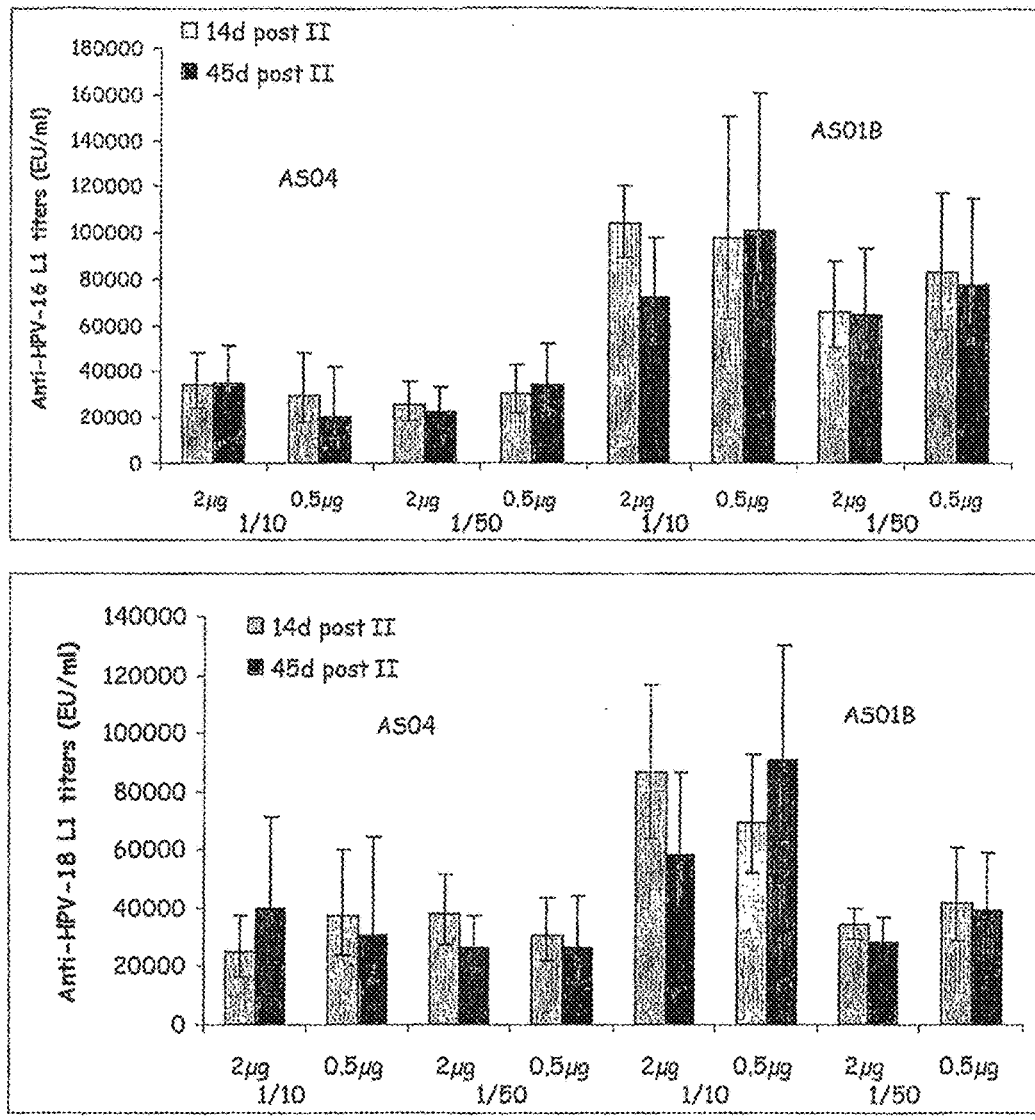

FIG. 9: Humoral responses to HPV 16 and 18 L1 in mice following immunisation with adjuvanted HPV formulations, comparing adjuvants having two different concentrations of immunostimulants FIG. 10: Cell mediated immune response in mice: Intracellular Cytokine Staining—VLP16 and 18 CD4+ T cells following immunisation with adjuvanted HPV formulations, comparing adjuvants having two different concentrations of immunostimulants FIG. 11: Production of Specific B Memory cells following immunisation with adjuvanted HPV formulations, comparing adjuvants having two different concentrations of immunostimulants FIG. 12: Preclinical comparison of adjuvanted *S. pneumoniae* vaccines in mice, comparing adjuvants having two different concentrations of immunostimulants.

Figure 13:
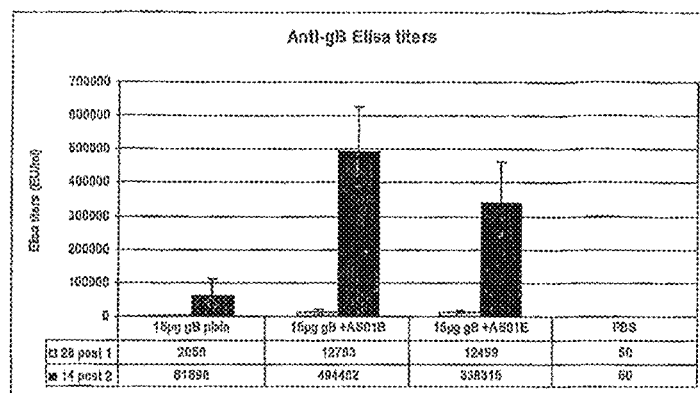

FIG. 13: Guinea pig Anti-gB ELISA titers following immunisation with adjuvanted Gb vaccine, comparing adjuvants having two different concentrations of immunostimulants.

Figure 14:
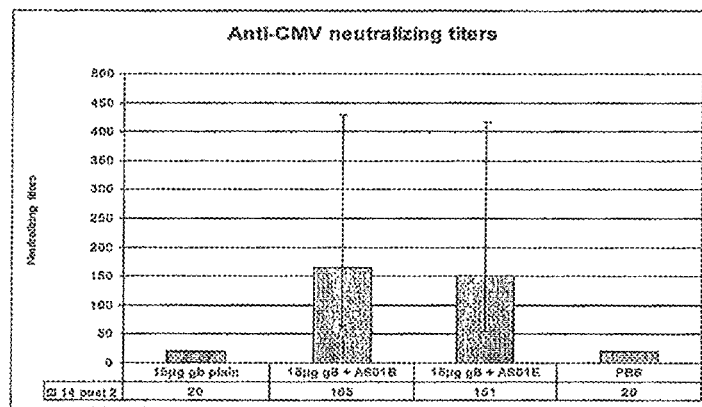

FIG. 14: Guinea Pig Anti CMV neutralizing titers following immunisation with adjuvanted Gb vaccine, comparing adjuvants having two different concentrations of immunostimulants.

Figure 15:
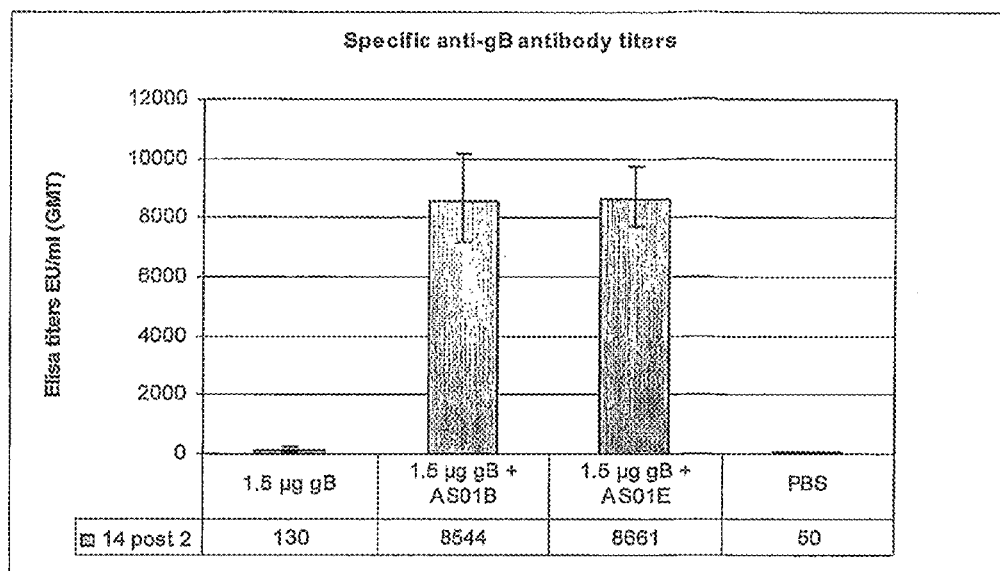

FIG. 15: Mice Anti-gB ELISA titers following immunisation with adjuvant gB vaccine.

Figure 16:
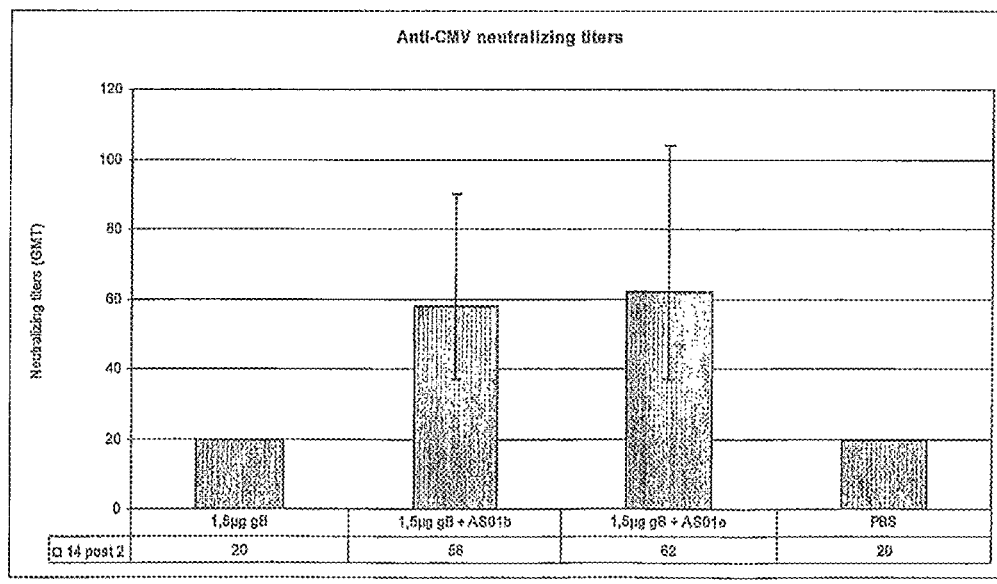

FIG. 16: Mice anti CMV neutralising titers following immunisation with adjuvanted gB vaccine.

FIG. 17: Mice study: Cell Mediated immunity—CMV specific CD4+ and CD8+ cells following re-stimulation with a pool of gB peptides (7 days post second immunisation)

Figure 18:
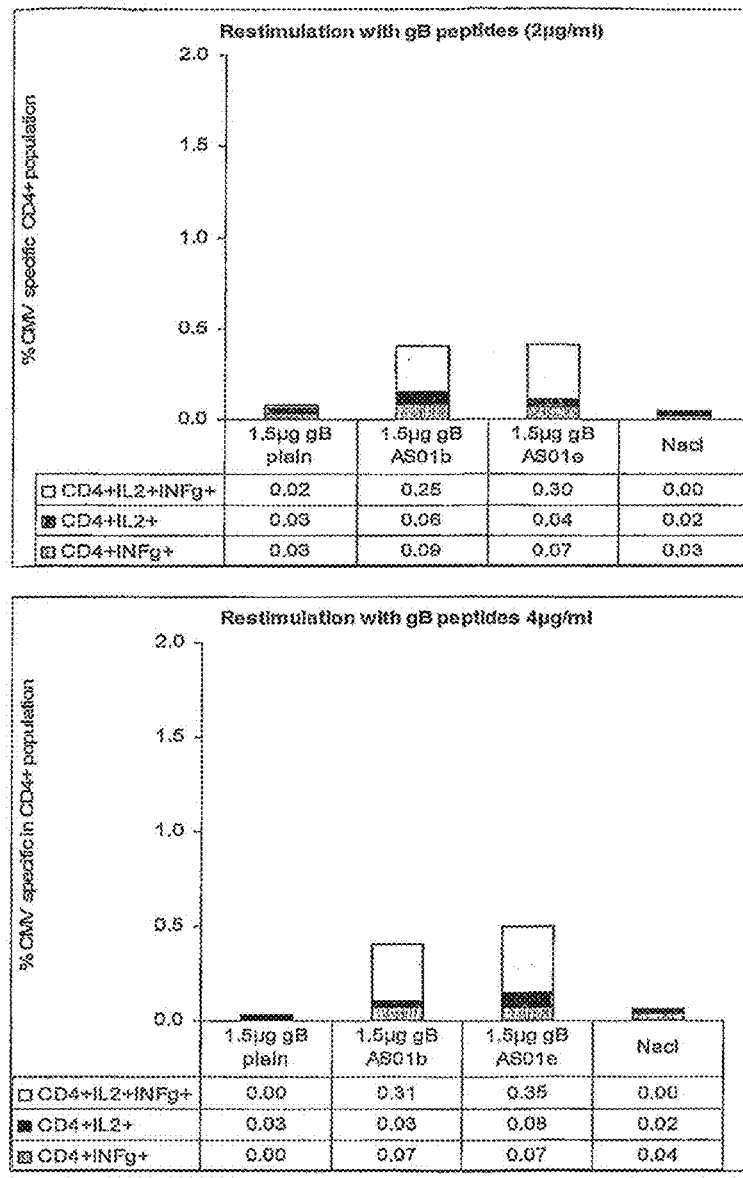

FIG. 18: Mice study. Cell Mediated immunity—CMV specific CD4+ cells following re-stimulation with two different dosages of a pool of gB peptides (21 days post second immunisation).

FIG. 19: Mice study. Cell Mediated immunity—CMV specific CD8+ cells following re-stimulation with two different dosages of a pool of gB peptides (21 days post second immunisation).

Figure 20:
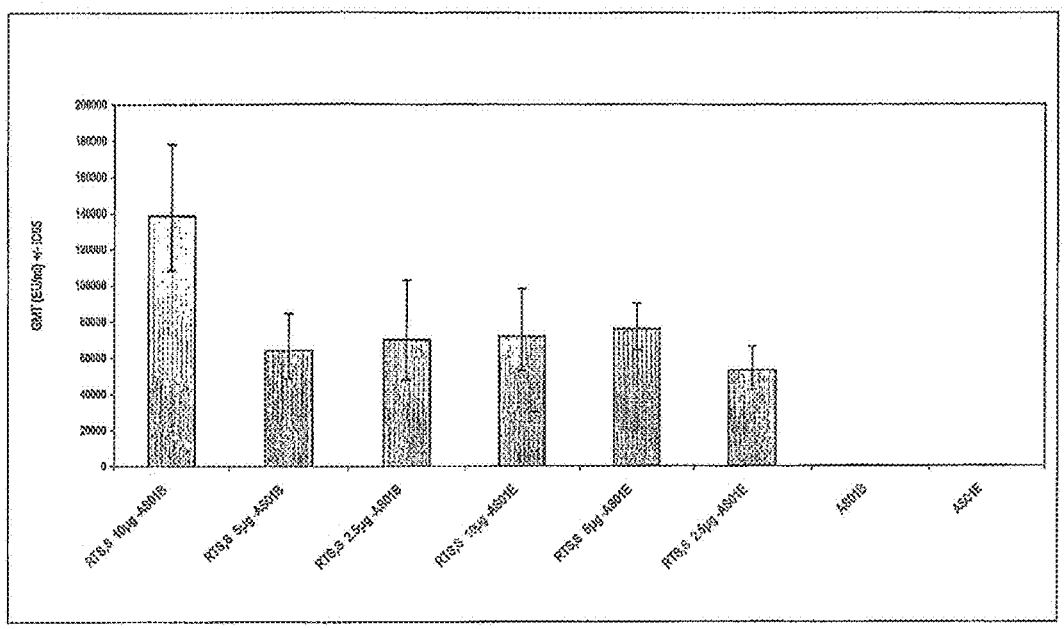

FIG. 20: Geometric mean antibody titers (GMT) against Circumsporozoite protein CSP following immunization with adjuvanted RTS,S vaccine in mice; comparing adjuvants having immunostimulants at two different concentrations.

Figure 21:
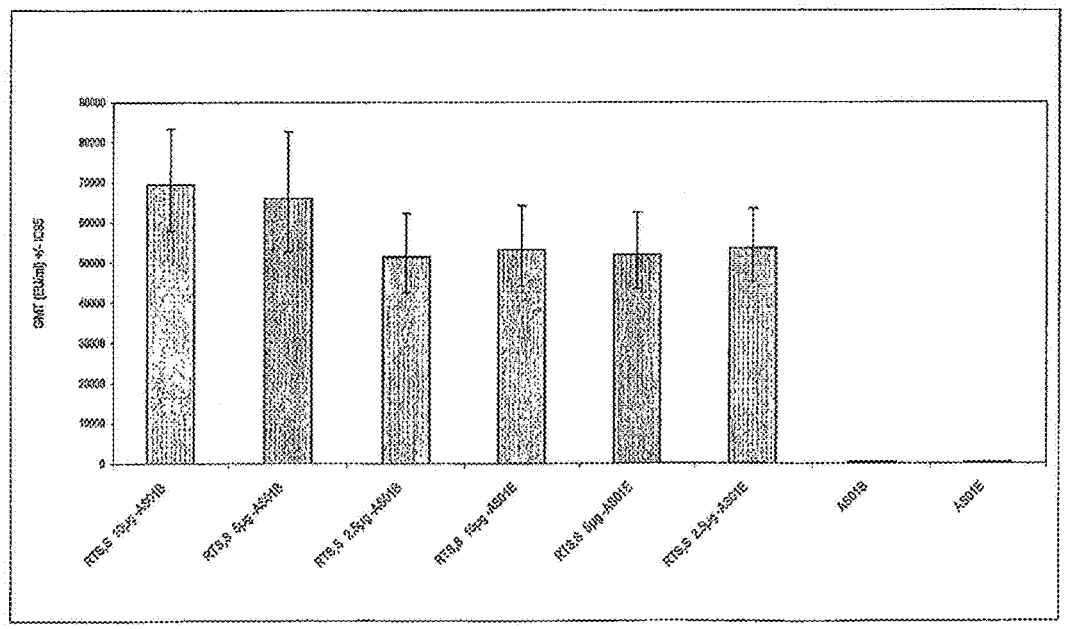

FIG. 21: Geometric mean antibody titers (GMT) against Hepatitis B surface antigen (HBs) following immunization with adjuvanted RTS,S vaccine in mice; comparing adjuvants with immunostimulants at two different concentrations.

FIG. 22: Ex vivo expression of IL-2 and/or IFN gamma by CSP-specific CD4 and CD8 T cells following immunization with an adjuvanted RTS,S immunogenic composition, comparing adjuvants with immunostimulants at two different concentrations.

FIG. 23: Ex vivo expression of IL-2 and/or IFN gamma by HBs-specific CD4 and CD8 T cells following immunization with an adjuvanted RTS,S immunogenic composition, comparing adjuvants with immunostimulants at two different concentrations.

FIG. 24: Humoral responses in mice following immunisation with adjuvanted trivalent split influenza vaccine (A/New Caledonia,A/Wyoming, B/Jiangsu), immunostimulants at two different concentrations.

Figure 25:
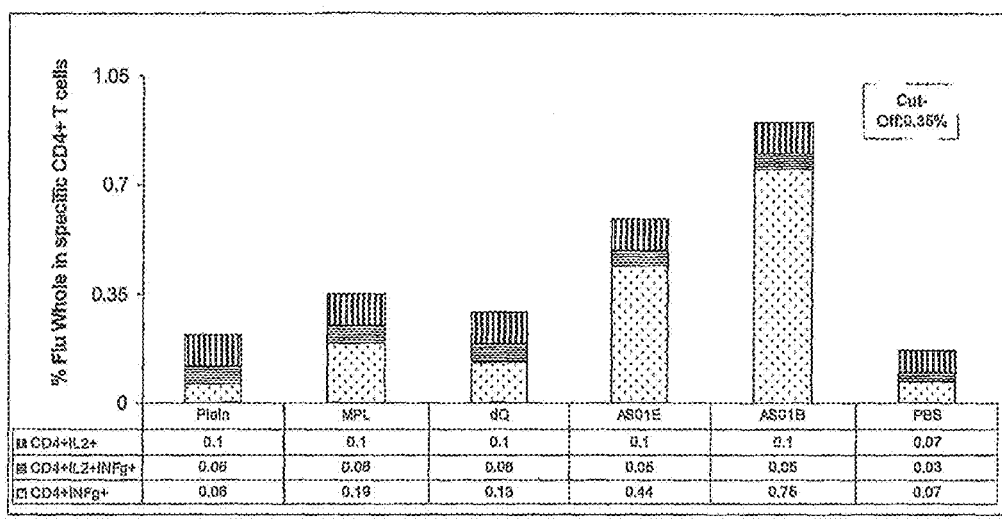

FIG. 25: Cell mediated immune response in mice following immunisation with adjuvanted trivalent influenza vaccine (A/New Caledonia,A/Wyoming, B/Jiangsu), immunostimulants at two different concentrations.

FIG. 26: Preclinical results in mice comparing VZV gE vaccines adjuvant with AS01B or AS01E.

Figure 27:
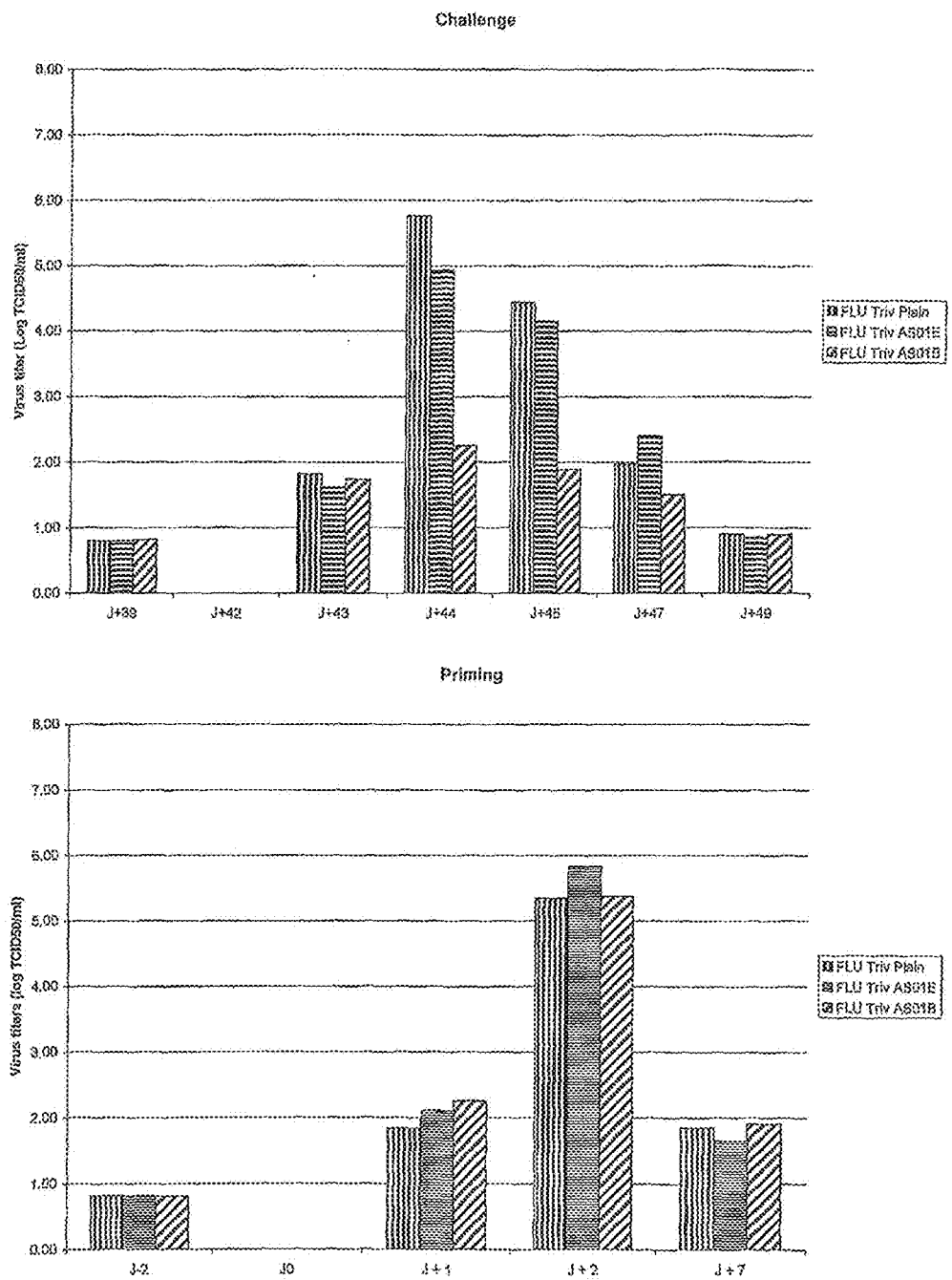

FIG. 27: viral nasal wash titres following priming and challenge with influenza virus antigens—immunisation with A/New Caledonia,A/Wyoming, B/Jiangsu either plain or adjuvanted with adjuvant compositions comprising immunostimulants at two different concentrations, in ferrets FIG. 28: Body temperature monitoring in ferrets following priming and challenge with influenza antigens. Immunisation with A/New Caledonia,A/Wyoming, B/Jiangsu either plain or adjuvanted with adjuvant compositions comprising immunostimulants at two different concentrations, FIG. 29: Anti HI titers for the A strains in the trivalent vaccine formulation following immunisation and challenge with influenza antigen preparations. Immunisation with A/New Caledonia,A/Wyoming, B/Jiangsu either plain or adjuvanted with adjuvant compositions comprising immunostimulants at two different concentrations, FIG. 30: Anti HI titres for B/Jiangsu and the drift strain used for challenge following immunisation and challenge with influenza antigen preparations. Immunisation with A/New Caledonia,A/Wyoming, B/Jiangsu either plain or adjuvanted with adjuvant compositions comprising immunostimulants at two different concentrations,

DETAILED DESCRIPTION

The present inventors have discovered that an adjuvant composition which comprises a saponin presented in the form of a liposome, and a lipopolysaccharide, where each immunostimulant is present at a level at or below 30 μg per human dose can improve immune responses to an antigenic preparation, whilst at the same time having lower reactogenicity than some of the prior art formulations where the immunostimulants were present at higher levels per human dose.

The present inventors have further found that an influenza formulation comprising an influenza virus or antigenic preparation thereof together with an adjuvant comprising a saponin presented in the form of a liposome, and optionally additionally with a lipid A derivative such as 3D-MPL, was capable of improving the CD4 T-cell immune response against said antigen or antigenic composition compared to that obtained with the un-adjuvanted virus or antigenic preparation thereof. The formulations adjuvanted with saponin presented in the form of a liposome are advantageously used to induce anti-influenza CD4-T cell responses capable of detection of influenza epitopes presented by MHC class II molecules. The present applicant has found that it is effective to target the cell-mediated immune system in order to increase responsiveness against homologous and drift influenza strains (upon vaccination and infection).

It is a specific embodiment of the present invention that the compositions for use in the present invention may be able to provide, in humans, better sero-protection against influenza following revaccination, as assessed by the number of human subjects meeting the influenza correlates of protection. Furthermore, it is another specific embodiment that the composition for use in the present invention will also be able to induce a higher B cell memory response following the first vaccination of a human subject, and a higher humoral response following revaccination, compared to the un-adjuvanted composition.

The adjuvanted influenza compositions according to the invention have several advantages:

1) An improved immunogenicity: they will allow to restore weak immune response in the elderly people (over 50 years of age, typically over 65 years of age) to levels seen in young people (antibody and/or T cell responses);
2) An improved cross-protection profile: increased cross-protection against variant (drifted) influenza strains;
3) They will also allow a reduced antigen dosage to be used for a similar response, thus ensuring an increased capacity in case of emergency (pandemics for example).

In another aspect of the invention, the inventors have discovered that the adjuvant composition as defined herein demonstrates immunogenicity results for both antibody production and post-vaccination frequency of influenza-specific CD4 which are equivalent to, or sometimes greater than, those generated with non-adjuvanted vaccine. This effect is in particular of value in the elderly population and can be achieved with an adjuvant as herein defined containing a lower dose of immunostimulants. In addition, reactogenicity symptoms showed a trend to be higher in the group who received the vaccine adjuvanted with the highest immunostimulants concentration compared to the group who received the adjuvanted vaccine wherein the immunostimulants is at a lower concentration.

These findings can be applied to other forms of the same antigens, and to other antigens.

Saponin Adjuvant

The adjuvant composition of the invention comprises a saponin adjuvant presented in the form of a liposome.

A particularly suitable saponin for use in the present invention is Quil A and its derivatives. Quil A is a saponin preparation isolated from the South American tree *Quillaja saponaria Molina* and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria Molina*, which induces CD8+ cytotoxic T cells (CTLs), Th1 cells and a predominant IgG2a antibody response and is a preferred saponin in the context of the present invention.

In a suitable form of the present invention, the saponin adjuvant within the immunogenic composition is a derivative of *saponaria molina* quil A, preferably an immunologically active fraction of Quil A, such as QS-17 or QS-21, suitably QS-21. In one embodiment the compositions of the invention contain the immunologically active saponin fraction in substantially pure form. Preferably the compositions of the invention contain QS21 in substantially pure form, that is to say, the QS21 is at least 90% pure, for example at least 95% pure, or at least 98% pure.

In a specific embodiment, QS21 is provided in its less reactogenic composition where it is quenched with an exogenous sterol, such as cholesterol for example. Several particular forms of less reactogenic compositions wherein QS21 is quenched with an exogenous cholesterol exist. In a specific embodiment, the saponin/sterol is in the form of a liposome structure (WO 96/33739, Example 1). In this embodiment the liposomes suitably contain a neutral lipid, for example phosphatidylcholine, which is suitably non-crystalline at room temperature, for example eggyolk phosphatidylcholine, dioleoyl phosphatidylcholine (DOPC) or dilauryl phosphatidylcholine. The liposomes may also contain a charged lipid which increases the stability of the lipsome-QS21 structure for liposomes composed of saturated lipids. In these cases the amount of charged lipid is suitably 1-20% w/w, preferably 5-10%. The ratio of sterol to phospholipid is 1-50% (mol/mol), suitably 20-25%.

Suitable sterols include β-sitosterol, stigmasterol, ergosterol, ergocalciferol and cholesterol. In one particular embodiment, the adjuvant composition comprises cholesterol as sterol. These sterols are well known in the art, for example cholesterol is disclosed in the Merck Index, 11th Edn., page 341, as a naturally occurring sterol found in animal fat.

Adjuvant compositions of the invention comprising QS21 and a sterol, cholesterol in particular, show a decreased reactogenicity when compared to compositions in which the sterol is absent, while the adjuvant effect is maintained. Reactogenicity studies may be assessed according to the methods disclosed in WO 96/33739. The sterol according to the invention is taken to mean an exogenous sterol, i.e. a sterol which is not endogenous to the organism from which the antigenic preparation is taken but is added to the antigen preparation or subsequently at the moment of formulation. Typically, the sterol may be added during subsequent formulation of the antigen preparation with the saponin adjuvant, by using, for example, the saponin in its form quenched with the sterol. Suitably the exogenous sterol is associated to the saponin adjuvant as described in WO 96/33739.

Where the active saponin fraction is QS21, the ratio of QS21:sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). The sterol is suitably cholesterol.

Other useful saponins are derived from the plants *Aesculus hippocastanum* or *Gyophilla struthium*. Other saponins which have been described in the literature include Escin, which has been described in the Merck index ($12^{Th}$ ed: entry 3737) as a mixture of saponins occurring in the seed of the horse chestnut tree, Lat: *Aesculus hippocastanum*. Its isolation is described by chromatography and purification (Fiedler, *Arzneimittel-Forsch.* 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August; 44(8):1454-1464)). Sapoalbin from *Gypsophilla struthium* (R. Vochten et al., 1968, J. Pharm.

Belg., 42, 213-226) has also been described in relation to ISCOM production for example.

A key aspect of the present invention is the fact that the immunologically active saponin, which is preferably QS21, can be used at lower amounts than had previously been thought useful, suitably at below 30 µg, for example between 1 and 30 µg, per human dose of the immunogenic composition.

The invention therefore provides a human dose of an immunogenic composition comprising immunologically active saponin, preferably QS21, at a level of 30 µg or less, for example between 1 and 30 µg.

In one embodiment, an immunogenic composition in a volume which is suitable for a human dose which human dose of the immunogenic composition comprises QS21 at a level of around 25 µg, for example between 20-30 µg, suitably between 21-29 µg or between 22 and 28 µg or between 23 and 27 µg or between 24 and 26 µg, or 25 µg.

In another embodiment, the human dose of the immunogenic composition comprises QS21 at a level of around 10 µg per, for example between 5 and 15 µg, suitably between 6 and 14 µg, for example between 7 and 13 µg or between 8 and 12 µg or between 9 and 11 µg, or 10 µg.

In a further embodiment, the human dose of the immunogenic composition comprises QS21 at a level of around 5 µg, for example between 1 and 9 µg, or between 2 and 8 µg or suitably between 3 and 7 µg or 4 and 6 µg, or 5 µg.

A suitable amount of QS21 is for example any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, µg (w/v) per human dose of the immunogenic composition.

By the term "human dose" is meant a dose which is in a volume suitable for human use. Generally this is between 0.3 and 1.5 ml. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. The invention is characterised in that each human dose contains 30 µg or less, for example between 1 and 30 µg, of QS21.

The invention further provides an adjuvant composition comprising 30 µg or less, for example between 1 and 30 µg, of QS21. Typically such an adjuvant composition will be in a human dose suitable volume. Where the adjuvant is in a liquid form to be combined with a liquid form of an antigenic composition, the adjuvant composition will be in a human dose suitable volume which is approximately half of the intended final volume of the human dose, for example a 360 µl volume for an intended human dose of 0.7 ml, or a 250 µl volume for an intended human dose of 0.5 ml. The adjuvant composition is diluted when combined with the antigen composition to provide the final human dose of vaccine. The final volume of such dose will of course vary dependent on the initial volume of the adjuvant composition and the volume of antigen composition added to the adjuvant composition. In an alternative embodiment, liquid adjuvant is used to reconstitute a lyophilised antigen composition. In this embodiment, the human dose suitable volume of the adjuvant composition is approximately equal to the final volume of the human dose. The liquid adjuvant composition is added to the vial containing the lyophilised antigen composition. The final human dose can vary between 0.5 and 1.5 ml. In a particular embodiment the human dose is 0.5 ml, in this embodiment the vaccine composition of the invention will comprise a level of QS21 at or below 30 µg, for example between 1 and 30 µg, per 0.5 ml human dose, furthermore in this embodiment an adjuvant composition of the invention will comprise a level of QS21 at or below 30 µg, for example between 1 and 30 µg, per 250 µl of adjuvant composition, or per 500 µl of adjuvant composition dependent on whether the adjuvant composition is intended to be combined with a liquid or lyophilised antigen composition respectively.

Specifically when combined with an influenza antigen, an amount of QS21 can be used, for example, at an amount of 1 to 100 µg (w/v) per composition dose, preferably in an amount of 10 to 50 µg (w/v) per composition dose. A suitable amount of QS21 is for example any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 µg (w/v) per composition dose. More preferably, QS21 amount ranges from 25 to 75 µg (w/v) per composition dose. Usually a composition dose will be ranging from about 0.5 ml to about 1 ml. A typical vaccine dose are 0.5 ml, 0.6 ml, 0.7 ml, 0.8 ml, 0.9 ml or 1 ml. In a preferred embodiment, a final concentration of 50 µg of QS21 is contained per ml of vaccine composition, or 25 µg per 0.5 ml vaccine dose. In other preferred embodiments, a final concentration of 35.7 µg or 71.4 µg of QS21 is contained per ml of vaccine composition. Specifically, a 0.5 ml vaccine dose volume contains 25 µg or 50 µg of QS21 per dose.

The dose of QS21 is suitably able to enhance an immune response to an antigen in a human. In particular a suitable QS21 amount is that which improves the immunological potential of the composition compared to the unadjuvanted composition, or compared to the composition adjuvanted with another QS21 amount, whilst being acceptable from a reactogenicity profile.

3D-MPL Adjuvant

The composition further comprises an additional adjuvant which is a lipopolysaccharide, suitably a non-toxic derivative of lipid A, particularly monophosphoryl lipid A or more particularly 3-Deacylated monophoshoryl lipid A (3D-MPL).

3D-MPL is sold under the name MPL by GlaxoSmithKline Biologicals N.A. and is referred throughout the document as MPL or 3D-MPL. see, for example, U.S. Pat. Nos. 4,436,727; 4,877,611; 4,866,034 and 4,912,094. 3D-MPL primarily promotes CD4+ T cell responses with an IFN-g (Th1) phenotype. 3D-MPL can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3D-MPL is used. Small particle 3D-MPL has a particle size such that it may be sterile-filtered through a 0.22 µm filter. Such preparations are described in WO 94/21292.

A key aspect of the present invention is the fact that the lipopolysaccharide, which is preferably 3D-MPL, can be used at lower amounts than had previously been thought useful, suitably at a level of 30 µg or less, for example between 1 and 30 µg, per human dose of the immunogenic composition.

The invention therefore provides a human dose of an immunogenic composition comprising lipopolysaccharide, preferably 3D-MPL, at a level of 30 µg or less, for example between 1 and 30 µg.

In one embodiment, the human dose of the immunogenic composition comprises 3D-MPL at a level of around 25 µg, for example between 20-30 µg, suitably between 21-29 µg or between 22 and 28 µg or between 23 and 27 µg or between 24 and 26 µg, or 25 µg. In another embodiment, the human dose of the immunogenic composition comprises 3D-MPL at a level of around 10 µg, for example between 5 and 15 µg, suitably between 6 and 14 µg, for example between 7 and 13 µg or between 8 and 12 µg or between 9 and 11 µg, or 10 µg.

In a further embodiment, the human dose of the immunogenic composition comprises 3D-MPL at a level of around 5 µg, for example between 1 and 9 µg, or between 2 and 8 µg or suitably between 3 and 7 µg or 4 and 6 µg, or 5 µg.

A suitable amount of 3D-MPL is for example any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, µg (w/v) per human dose of the immunogenic composition.

In one embodiment, the volume of the human dose is 0.5 ml. In a further embodiment, the immunogenic composition is in a volume suitable for a human dose which volume is higher than 0.5 ml, for example 0.6, 0.7, 0.8, 0.9 or 1 ml. In a further embodiment, the human dose is between 1 ml and 1.5 ml. The invention is characterised in that each human dose contains 30 µg or less, for example between 1 and 30 µg of 3D-MPL.

The invention further provides an adjuvant composition comprising 30 µg or less, for example between 1 and 30 µg, of 3D-MPL. Typically such an adjuvant composition will be in a human dose suitable volume. Where the adjuvant is in a liquid form to be combined with a liquid form of an antigenic composition, the adjuvant composition will be in a human dose suitable volume which is approximately half of the intended final volume of the human dose, for example a 360 µl volume for an intended human dose of 0.7 ml, or a 250 µl volume for an intended human dose of 0.5 ml. The adjuvant composition is diluted when combined with the antigen composition to provide the final human dose of immunogenic composition. The final volume of such dose will of course vary dependent on the initial volume of the adjuvant composition and the volume of antigen composition added to the adjuvant composition. In an alternative embodiment, liquid adjuvant composition is used to reconstitute a lyophilised antigen composition. In this embodiment, the human dose suitable volume of the adjuvant composition is approximately equal to the final volume of the human dose. The liquid adjuvant composition is added to the vial containing the lyophilised antigen composition. The final human dose can vary between 0.5 and 1.5 ml. In a particular embodiment the human dose is 0.5 ml, in this embodiment the vaccine composition of the invention will comprise a level of 3D-MPL at or below 30 µg, for example between 1 and 30 µg, per 0.5 ml human dose, furthermore in this embodiment an adjuvant composition of the invention will comprise a level of 3D-MPL at or below 30 µg, for example between 1 and 30 µg, per 250 µl of adjuvant composition, or per 500 µl of adjuvant composition dependent on whether the adjuvant composition is intended to be combined with a liquid or lyophilised antigen composition respectively.

When the immunogenic composition contains an influenza virus or antigenic preparation thereof, the adjuvant composition which comprises a saponin in the form of a liposome optionally additionally contains a lipid A derivative, particularly monophosphoryl lipid A or more particularly 3D-MPL. In this embodiment, 3D-MPL can be used, for example, at an amount of 1 to 100 µg (w/v) per composition dose, preferably in an amount of 10 to 50 µg (w/v) per composition dose. A suitable amount of 3D-MPL is for example any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 µg (w/v) per composition dose. More preferably, 3D-MPL amount ranges from 25 to 75 µg (w/v) per composition dose. Usually a composition dose will be ranging from about 0.5 ml to about 1 ml. A typical vaccine dose are 0.5 ml, 0.6 ml, 0.7 ml, 0.8 ml, 0.9 ml or 1 ml. In one embodiment, a final concentration of 50 µg of 3D-MPL is contained per ml of vaccine composition, or 25 µg per 0.5 ml vaccine dose. In another embodiment, a final concentration of 35.7 µg or 71.4 µg of 3D-MPL is contained per ml of vaccine composition. Specifically, a 0.5 ml vaccine dose volume contains 25 µg or 50 µg of 3D-MPL per dose.

The dose of 3D-MPL is suitably able to enhance an immune response to an antigen in a human. In particular a suitable 3D-MPL amount is that which improves the immunological potential of the composition compared to the unadjuvanted composition, or compared to the composition adjuvanted with another MPL amount, whilst being acceptable from a reactogenicity profile.

Suitable compositions of the invention are those wherein liposomes are initially prepared without MPL (as described in WO 96/33739), and MPL is then added, suitably as small particles of below 100 nm particles or particles that are susceptible to sterile filtration through a 0.22 µm membrane. The MPL is therefore not contained within the vesicle membrane (known as MPL out). Compositions where the MPL is contained within the vesicle membrane (known as MPL in) also form an aspect of the invention. The antigen can be contained within the vesicle membrane or contained outside the vesicle membrane. Suitably soluble antigens are outside and hydrophobic or lipidated antigens are either contained inside or outside the membrane.

In one embodiment the adjuvant composition of the invention comprises both lipopolysaccharide and immunologically active saponin. In a specific embodiment of the invention, the lipopolysaccharide is 3D-MPL and the immunologically active saponin is QS21. In a further embodiment of the invention, the adjuvant composition consists essentially of a lipopolysaccharide and immunologically active saponin in a liposomal formulation. Suitably in one form of this embodiment, the adjuvant composition consists essentially of 3D-MPL and QS21, with optionally sterol which is preferably cholesterol.

In a further embodiment of the invention, the adjuvant composition comprises in a liposomal formulation lipopolysaccharide and immunologically active saponin in combination with one or more further immunostimulants or adjuvants. Suitably in one form of this embodiment the lipopolysaccharide is 3D-MPL and the immunologically active saponin is QS21.

In a specific embodiment, QS21 and 3D-MPL are present in the same final concentration per human dose of the immunogenic composition. In one aspect of this embodiment, a human dose of immunogenic composition comprises a final level of 25 µg of 3D-MPL and 25 µg of QS21. In a further embodiment, a human dose of immunogenic composition comprises a final level of 10 µg each of MPL and QS21. In a further specific embodiment is provided an adjuvant composition having a volume of 250 µl and comprising a level of 25 µg of 3D-MPL and 25 µg of QS21, or 10 µg each of MPL and QS21.

Antigens that may be used with the adjuvant compositions of the present invention include viral, parasitic, bacterial or tumour associated antigens, for example:

An influenza virus or antigenic preparation thereof for use according to the present invention, which may be a split influenza virus or split virus antigenic preparation thereof. In an alternative embodiment the influenza preparation may contain another type of inactivated influenza antigen, such as inactivated whole virus or purified HA and NA (subunit vaccine), or an influenza virosome. In a still further embodiment, the influenza virus may be a live attenuated influenza preparation.

A split influenza virus or split virus antigenic preparation thereof for use according to the present invention is suitably an inactivated virus preparation where virus particles are disrupted with detergents or other reagents to solubilise the lipid envelope. Split virus or split virus antigenic preparations thereof are suitably prepared by fragmentation of whole influenza virus, either infectious or inactivated, with solubilising concentrations of organic solvents or detergents and subsequent removal of all or the majority of the solubilising agent and some or most of the viral lipid material. By split virus antigenic preparation thereof is meant a split virus preparation which may have undergone some degree of purification compared to the split virus whilst retaining most of the antigenic properties of the split virus components. For example, when produced in eggs, the split virus may be depleted from egg-contaminating proteins, or when produced in cell culture, the split virus may be depleted from host cell contaminants. A split virus antigenic preparation may comprise split virus antigenic components of more than one viral strain. Vaccines containing split virus (called 'influenza split vaccine') or split virus antigenic preparations generally contain residual matrix protein and nucleoprotein and sometimes lipid, as well as the membrane envelope proteins. Such split virus vaccines will usually contain most or all of the virus structural proteins although not necessarily in the same proportions as they occur in the whole virus.

Alternatively, the influenza virus may be in the form of a whole virus vaccine. This may prove to be an advantage over a split virus vaccine for a pandemic situation as it avoids the uncertainty over whether a split virus vaccine can be successfully produced for a new strain of influenza virus. For some strains the conventional detergents used for producing the split virus can damage the virus and render it unusable. Although there is always the possibility to use different detergents and/or to develop a different process for producing a split vaccine, this would take time, which may not be available in a pandemic situation. In addition to the greater degree of certainty with a whole virus approach, there is also a greater vaccine production capacity than for split virus since considerable amounts of antigen are lost during additional purification steps necessary for preparing a suitable split vaccine.

In another embodiment, the influenza virus preparation is in the form of a purified sub-unit influenza vaccine. Sub-unit influenza vaccines generally contain the two major envelope proteins, HA and NA, and may have an additional advantage over whole virion vaccines as they are generally less reactogenic, particularly in young vaccinees. Sub-unit vaccines can be produced either recombinantly or purified from disrupted viral particles.

In another embodiment, the influenza virus preparation is in the form of a virosome. Virosomes are spherical, unilamellar vesicles which retain the functional viral envelope glycoproteins HA and NA in authentic conformation, intercalated in the virosomes' phospholipids bilayer membrane.

Said influenza virus or antigenic preparation thereof may be egg-derived or cell-culture derived.

For example, the influenza virus antigen or antigenic preparations thereof according to the invention may be derived from the conventional embryonated egg method, by growing influenza virus in eggs and purifying the harvested allantoic fluid. Eggs can be accumulated in large numbers at short notice. Alternatively, they may be derived from any of the new generation methods using cell or cell culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 cells. Suitable cell substrates are not limited to cell lines; for example primary cells such as chicken embryo fibroblasts and avian cell lines are also included.

The influenza virus antigen or antigenic preparation thereof may be produced by any of a number of commercially applicable processes, for example the split flu process described in patent no. DD 300 833 and DD 211 444, incorporated herein by reference. Traditionally split flu was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate as described in patent no. DD 155 875, incorporated herein by reference. Detergents that can be used as splitting agents include cationic detergents e.g. cetyl trimethyl ammonium bromide (CTAB), other ionic detergents e.g. laurylsulfate, taurodeoxycholate, or non-ionic detergents such as the ones described above including Triton X-100 (for example in a process described in Lina et al, 2000, Biologicals 28, 95-103) and Triton N-101, or combinations of any two or more detergents.

The preparation process for a split vaccine may include a number of different filtration and/or other separation steps such as ultracentrifugation, ultrafiltration, zonal centrifugation and chromatography (e.g. ion exchange) steps in a variety of combinations, and optionally an inactivation step e.g. with heat, formaldehyde or β-propiolactone or U.V. which may be carried out before or after splitting. The splitting process may be carried out as a batch, continuous or semi-continuous process. A preferred splitting and purification process for a split immunogenic composition is described in WO 02/097072.

Preferred split flu vaccine antigen preparations according to the invention comprise a residual amount of Tween 80 and/or Triton X-100 remaining from the production process, although these may be added or their concentrations adjusted after preparation of the split antigen. Preferably both Tween 80 and Triton X-100 are present. The preferred ranges for the final concentrations of these non-ionic surfactants in the vaccine dose are:

Tween 80: 0.01 to 1%, more preferably about 0.1% (v/v)
Triton X-100: 0.001 to 0.1 (% w/v), more preferably 0.005 to 0.02% (w/v).

In a specific embodiment, the final concentration for Tween 80 ranges from 0.025%-0.09% w/v. In another specific embodiment, the antigen is provided as a 2 fold concentrated mixture, which has a Tween 80 concentration ranging from 0.025%-0.2% (w/v) and has to be diluted two times upon final formulation with the adjuvanted (or the buffer in the control formulation).

In another specific embodiment, the final concentration for Triton X-100 ranges from 0.004%-0.017% w/v. In another specific embodiment, the antigen is provided as a 2 fold concentrated mixture, which has a Triton X-100 concentration ranging from 0.005%-0.034% (w/v) and has to be diluted two times upon final formulation with the adjuvanted (or the buffer in the control formulation).

Preferably the influenza preparation is prepared in the presence of low level of thiomersal, or preferably in the absence of thiomersal. Preferably the resulting influenza preparation is stable in the absence of organomercurial preservatives, in particular the preparation contains no residual thiomersal. In particular the influenza virus preparation comprises a haemagglutinin antigen stabilised in the absence of thiomersal, or at low levels of thiomersal (generally 5 µg/ml or less). Specifically the stabilization of B influenza strain is performed by a derivative of alpha tocopherol, such as alpha tocopherol succinate (also known as vitamin E succinate, i.e. VES). Such preparations and methods to prepare them are disclosed in WO 02/097072.

A preferred composition contains three inactivated split virion antigens prepared from the WHO recommended strains of the appropriate influenza season.

Preferably the influenza virus or antigenic preparation thereof and the adjuvant according to the invention are contained in the same container. It is referred to as 'one vial approach'. Preferably the vial is a pre-filled syringe. In an alternative embodiment, the influenza virus or antigenic preparation thereof and adjuvant according to the invention are contained in separate containers or vials and admixed shortly before or upon administration into the subject. It is referred to as 'two vials approach'. By way of example, when the vaccine is a 2 components vaccine for a total dose volume of 0.7 ml, the concentrated antigens (for example the concentrated trivalent inactivated split virion antigens) are presented in one vial (335 µl) (antigen container) and a pre-filled syringe contains the adjuvant (360 µl) (adjuvant container). At the time of injection, the content of the vial containing the concentrated trivalent inactivated split virion antigens is removed from the vial by using the syringe containing the adjuvant followed by gentle mixing of the syringe. Prior to injection, the used needle is replaced by an intramuscular needle and the volume is corrected to 530 µl. In this example, one dose of the reconstituted adjuvanted influenza vaccine candidate corresponds to 530 µl.

In one aspect of the invention, where there is a multivalent composition, then at least one influenza strain in said multivalent immunogenic composition as herein defined is associated with a pandemic outbreak or have the potential to be associated with a pandemic outbreak. Such strain may also be referred to as 'pandemic strains' in the text below. In particular, when the vaccine is a multivalent vaccine such as a bivalent, or a trivalent or a quadrivalent vaccine, at least one strain is associated with a pandemic outbreak or has the potential to be associated with a pandemic outbreak. Suitable strains are, but not limited to: H5N1, H9N2, H7N7, and H2N2.

Said influenza virus or antigenic preparation thereof is suitably multivalent such as bivalent or trivalent or quadrivalent. Preferably the influenza virus or antigenic preparation thereof is trivalent or quadrivalent, having an antigen from three different influenza strains, at least one strain being associated with a pandemic outbreak or having the potential to be associated with a pandemic outbreak.

The features of an influenza virus strain that give it the potential to cause a pandemic outbreak are: it contains a new haemagglutinin compared to the haemagglutinin in the currently circulating strains; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9, H7 or H6 which are found in birds. In either case the majority, or at least a large proportion of, or even the entire population has not previously encountered the antigen and is immunologically naïve to it.

Certain parties are generally at an increased risk of becoming infected with influenza in a pandemic situation. The elderly, the chronically ill and small children are particularly susceptible but many young and apparently healthy people are also at risk. For H2 influenza, the part of the population born after 1968 is at an increased risk. It is important for these groups to be protected effectively as soon as possible and in a simple way.

Another group of people who are at increased risk are travelers. People travel more today than ever before and the regions where most new viruses emerge, China and South East Asia, have become popular travel destinations in recent years. This change in travel patterns enables new viruses to reach around the globe in a matter of weeks rather than months or years.

Thus for these groups of people there is a particular need for vaccination to protect against influenza in a pandemic situation or a potential pandemic situation. Suitable strains are, but not limited to: H5N1, H9N2, H7N7, and H2N2.

Optionally the composition may contain more than three valencies, for example three non pandemic strains plus a pandemic strain. Alternatively the composition may contain three pandemic strains. Preferably the composition contains three pandemic strains.

Also examples of antigens for the immunogenic composition of the invention are Streptococcal antigens such as from Group A *Streptococcus*, or Group B *Streptococcus*, but most preferably from *Streptococcus pneumoniae*. At least one protein and/or at least one saccharide antigen is most preferably used. The at least one *Streptococcus pneumoniae* protein antigen(s) is most preferably selected from the group consisting of: pneumolysin, PspA or transmembrane deletion variants thereof, PspC or transmembrane deletion variants thereof, PsaA or transmembrane deletion variants thereof, glyceraldehyde-3-phosphate dehydrogenase, CbpA or transmembrane deletion variants thereof, PhtA, PhtD, PhtB, PhtE, SpsA, LytB, LytC, LytA, Sp125, Sp101, Sp128, Sp130 and Sp133, or immunologically functional equivalent thereof (for instance fusions of domains of the above proteins, for instance the PhtDE fusion proteins described in WO01/98334 and WO 03/54007).

Certain compositions are described in WO 00/56359 and WO 02/22167 and WO 02/22168 (incorporated by reference herein).

The antigen may comprise capsular saccharide antigens (preferably conjugated to a carrier protein), wherein the saccharides (most preferably polysaccharides) are derived from at least four serotypes of pneumococcus. In one embodiment the four serotypes include 6B, 14, 19F and 23F. In a further embodiment, at least 7 serotypes are included in the composition, for example those derived from serotypes 4, 6B, 9V, 14, 18C, 19F, and 23F. In a further embodiment, at least 10 serotypes are included in the composition, for example the composition in one embodiment includes capsular saccharides derived from serotypes 1, 4, 5, 6B, 7F, 9V, 14, 18C, 19F and 23F (preferably conjugated to a carrier protein). In another embodiment, the immunogenic composition comprises capsular saccharides derived from serotypes 1, 3, 4, 5, 6B, 7F, 9V, 14, 18C, 19F and 23F In a preferred embodiment of the invention at least 13 saccharide antigens (preferably conjugated to a carrier protein) are included, although further saccharide antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

Although the above saccharides are advantageously in their full-length, native polysaccharide form, it should be understood that size-reduced polysaccharides may also be used which are still immunogenic (see for example EP 497524 and 497525) if necessary when coupled to a protein carrier.

For the prevention/amelioration of pneumonia in the elderly (+55 years) population and Otitis media in Infants (up to 18 months) and toddlers (typically 18 months to 5 years), it is a preferred embodiment of the invention to combine a multivalent *Streptococcus pneumonia* saccharide as herein described with a *Streptococcus pneumoniae* protein preferably selected from the group of proteins listed above. A combination of pneumococcal proteins may also be advantageously utilised as described below.

Pneumococcal Proteins

*Streptococcus pneumoniae* antigens are preferably selected from the group consisting of: a protein from the polyhistidine triad family (Pht), a protein from the Lyt family, a choline binding protein, proteins having an LPXTG motif (where X is any amino acid), proteins having a Type II Signal sequence motif of LXXC (where X is any amino acid), and proteins having a Type I Signal sequence motif. Preferred examples within these categories (or motifs) are the following proteins (or truncate or immunologically functional equivalent thereof):

The Pht (Poly Histidine Triad) family comprises proteins PhtA, PhtB, PhtD, and PhtE. The family is characterised by a lipidation sequence, two domains separated by a proline-rich region and several histidine triads, possibly involved in metal or nucleoside binding or enzymatic activity, (3-5) coiled-coil regions, a conserved N-terminus and a heterogeneous C terminus. It is present in all strains of pneumococci tested. Homologous proteins have also been found in other Streptococci and *Neisseria*. Preferred members of the family comprise PhtA, PhtB and PhtD. More preferably, it comprises PhtA or PhtD. It is understood, however, that the terms Pht A, B, D, and E refer to proteins having sequences disclosed in the citations below as well as naturally-occurring (and man-made) variants thereof that have a sequence homology that is at least 90% identical to the referenced proteins. Preferably it is at least 95% identical and most preferably it is 97% identical.

With regards to the Pht proteins, PhtA is disclosed in WO 98/18930, and is also referred to Sp36. As noted above, it is a protein from the polyhistidine triad family and has the type II signal motif of LXXC.

PhtD is disclosed in WO 00/37105, and is also referred to Sp036D. As noted above, it also is a protein from the polyhistidine triad family and has the type II LXXC signal motif.

PhtB is disclosed in WO 00/37105, and is also referred to Sp036B. Another member of the PhtB family is the C3-Degrading Polypeptide, as disclosed in WO 00/17370. This protein also is from the polyhistidine triad family and has the type II LXXC signal motif. A preferred immunologically functional equivalent is the protein Sp42 disclosed in WO 98/18930. A PhtB truncate (approximately 79 kD) is disclosed in WO99/15675 which is also considered a member of the PhtX family.

PhtE is disclosed in WO00/30299 and is referred to as BVH-3.

SpsA is a Choline binding protein (Cbp) disclosed in WO 98/39450.

The Lyt family is membrane associated proteins associated with cell lysis. The N-terminal domain comprises choline binding domain(s), however the Lyt family does not have all the features found in the choline binding protein family (Cbp) family noted below and thus for the present invention, the Lyt family is considered distinct from the Cbp family. In contrast with the Cbp family, the C-terminal domain contains the catalytic domain of the Lyt protein family. The family comprises LytA, B and C. With regards to the Lyt family, LytA is disclosed in Ronda et al., Eur J Biochem, 164:621-624 (1987). LytB is disclosed in WO 98/18930, and is also referred to as Sp46. LytC is also disclosed in WO 98/18930, and is also referred to as Sp91. A preferred member of that family is LytC.

Another preferred embodiment are Lyt family (particularly LytA) truncates wherein "Lyt" is defined above and "truncates" refers to proteins lacking 50% or more of the Choline binding region. Preferably such proteins lack the entire choline binding region.

Sp125 is an example of a pneumococcal surface protein with the Cell Wall Anchored motif of LPXTG (where X is any amino acid). Any protein within this class of pneumococcal surface protein with this motif has been found to be useful within the context of this invention, and is therefore considered a further protein of the invention. Sp125 itself is disclosed in WO 98/18930, and is also known as ZmpB—a zinc metalloproteinase.

Sp101 is disclosed in WO 98/06734 (where it has the reference #y85993. It is characterised by a Type I signal sequence.

Sp133 is disclosed in WO 98/06734 (where it has the reference #y85992. It is also characterised by a Type I signal sequence.

Sp128 and Sp130 are disclosed in WO 00/76540.

The proteins used in the present invention are preferably selected from the group PhtD, PhtA and PhtE, or a combination of 2 or all 3 of these proteins (i.e. PhtA+D, A+E, D+E or A+D+E). Further pneumococcal protein antigens that may be included are one or more from the group consisting of: pneumolysin (also referred to as Ply; preferably detoxified by chemical treatment or mutation) [WO 96/05859, WO 90/06951, WO 99/03884], PsaA and transmembrane deletion variants thereof (Berry & Paton, Infect Immun 1996 December; 64(12):5255-62), PspA and transmembrane deletion variants thereof (U.S. Pat. No. 5,804,193, WO 92/14488, WO 99/53940), PspC and transmembrane deletion variants thereof (WO 97/09994, WO 99/53940), a member of the Choline binding protein (Cbp) family [e.g. CbpA and transmembrane deletion variants thereof (WO 97/41151; WO 99/51266)], Glyceraldehyde-3-phosphate-dehydrogenase (Infect. Immun. 1996 64:3544), HSP70 (WO 96/40928), PcpA (Sanchez-Beato et al. *FEMS Microbiol Lett* 1998, 164:207-14), M like protein (SB patent application No. EP 0837130), and adhesin 18627 (SB Patent application No. EP 0834568). The present invention also encompasses immunologically functional equivalents or truncates of such proteins (as defined above).

Concerning the Choline Binding Protein family, members of that family were originally identified as pneumococcal proteins that could be purified by choline-affinity chromatography. All of the choline-binding proteins are non-covalently bound to phosphorylcholine moieties of cell wall teichoic acid and membrane-associated lipoteichoic acid. Structurally, they have several regions in common over the entire family, although the exact nature of the proteins (amino acid sequence, length, etc.) can vary. In general, choline binding proteins comprise an N terminal region (N), conserved repeat regions (R1 and/or R2), a proline rich region (P) and a conserved choline binding region (C), made up of multiple repeats, that comprises approximately one half of the protein. As used in this application, the term "Choline Binding Protein family (Cbp)" is selected from the group consisting of Choline Binding Proteins as identified in WO 97/41151, PbcA, SpsA, PspC, CbpA, CbpD, and CbpG. CbpA is disclosed in WO 97/41151. CbpD and CbpG are disclosed in WO 00/29434. PspC is disclosed in WO 97/09994. PbcA is disclosed in WO 98/21337. Preferably the Choline Binding Proteins are selected from the group consisting of CbpA, PbcA, SpsA and PspC.

If a Cbp is the further protein utilised it may be a Cbp truncate wherein "Cbp" is defined above and "truncate" refers to proteins lacking 50% or more of the Choline binding region (C). Preferably such proteins lack the entire choline binding region. More preferably, the such protein truncates lack (i) the choline binding region and (ii) a portion of the N-terminal half of the protein as well, yet retain at least one repeat region (R1 or R2). More preferably still, the truncate has 2 repeat regions (R1 and R2). Examples of such preferred embodiments are NR1xR2, R1xR2, NR1xR2P and R1xR2P as illustrated in WO99/51266 or WO99/51188, however, other choline binding proteins lacking a similar choline binding region are also contemplated within the scope of this invention.

Cbp truncate-Lyt truncate chimeric proteins (or fusions) may also be used in the composition of the invention. Preferably this comprises NR1xR2 (or R1xR2 or NR1xR2P or R1xR2P) of Cbp and the C-terminal portion (Cterm, i.e., lacking the choline binding domains) of Lyt (e.g., LytC-Cterm or Sp91Cterm). More preferably Cbp is selected from the group consisting of CbpA, PbcA, SpsA and PspC. More preferably still, it is CbpA. Preferably, Lyt is LytC (also referred to as Sp91).

A PspA or PsaA truncate lacking the choline binding domain (C) and expressed as a fusion protein with Lyt may also be used. Preferably, Lyt is LytC.

In a pneumococcal composition it is possible to combine different pneumococcal proteins of the invention. Preferably the combination of proteins of the invention are selected from 2 or more (3 or 4) different categories such as proteins having a Type II Signal sequence motif of LXXC (where X is any amino acid, e.g., the polyhistidine triad family (Pht)), choline binding proteins (Cbp), proteins having a Type I Signal sequence motif (e.g., Sp101), proteins having a LPXTG motif (where X is any amino acid, e.g., Sp128, Sp130), toxins (e.g., Ply), etc. Preferred examples within these categories (or motifs) are the proteins mentioned above, or immunologically functional equivalents thereof. Toxin+Pht, toxin+Cbp, Pht+Cbp, and toxin+Pht+Cbp are preferred category combinations.

Preferred beneficial combinations include, but are not limited to, PhtD+NR1xR2, PhtD+NR1xR2-Sp91Cterm chimeric or fusion proteins, PhtD+Ply, PhtD+Sp128, PhtD+PsaA, PhtD+PspA, PhtA+NR1xR2, PhtA+NR1xR2-Sp91Cterm chimeric or fusion proteins, PhtA+Ply, PhtA+Sp128, PhtA+PsaA, PhtA+PspA, NR1xR2+LytC, NR1xR2+PspA, NR1xR2+PsaA, NR1xR2+Sp128, R1xR2+LytC, R1xR2+PspA, R1xR2+PsaA, R1xR2+Sp128, R1xR2+PhtD, R1xR2+PhtA. Preferably, NR1xR2 (or R1xR2) is from CbpA or PspC. More preferably it is from CbpA.

A particularly preferred combination of pneumococcal proteins comprises Ply (or a truncate or immunologically functional equivalent thereof)+PhtD (or a truncate or immunologically functional equivalent thereof) optionally with NR1xR2 (or R1xR2 or NR1xR2P or R1xR2P). Preferably, NR1xR2 (or R1xR2 or NR1xR2P or R1xR2P) is from CbpA or PspC. More preferably it is from CbpA.

The antigen may be a pneumococcus saccharide conjugate comprising polysaccharide antigens derived from at least four serotypes, preferably at least seven serotypes, more preferably at least ten serotypes, and at least one, but preferably 2, 3, or 4, *Streptococcus pneumoniae* proteins preferably selected from the group of proteins described above. Preferably one of the proteins is PhtD (or an immunologically functional equivalent thereof) and/or Ply (or an immunologically functional equivalent thereof).

A problem associated with the polysaccharide approach to vaccination, is the fact that polysaccharides per se are poor immunogens. To overcome this, saccharides may be conjugated to protein carriers, which provide bystander T-cell help. It is preferred, therefore, that the saccharides utilised in the invention are linked to such a protein carrier. Examples of such carriers which are currently commonly used for the production of saccharide immunogens include the Diphtheria and Tetanus toxoids (DT, DT CRM197 and TT respectively), Keyhole Limpet Haemocyanin (KLH), OMPC from *N. meningitidis*, and the purified protein derivative of Tuberculin (PPD).

A preferred carrier for the pneumococcal saccharide based immunogenic compositions (or vaccines) is protein D from *Haemophilus influenzae* (EP 594610-B), or fragments thereof. Fragments suitable for use include fragments encompassing T-helper epitopes. In particular a protein D fragment will preferably contain the N-terminal ⅓ of the protein. A protein D carrier is useful as a carrier in compositions where multiple pneumococcal saccharide antigens are conjugated. One or more pneumococcal saccharides in a combination may be advantageously conjugated onto protein D.

A further preferred carrier for the pneumococcal saccharide is the pneumococcal protein itself (as defined above in section "Pneumococcal Proteins of the invention").

The saccharide may be linked to the carrier protein by any known method (for example, by Likhite, U.S. Pat. No. 4,372,945 and by Armor et al., U.S. Pat. No. 4,474,757). Preferably, CDAP conjugation is carried out (WO 95/08348).

Preferably the protein:saccharide (weight:weight) ratio of the conjugates is 0.3:1 to 1:1, more preferably 0.6:1 to 0.8:1, and most preferably about 0.7:1.

Particularly preferred compositions of the invention comprise one or more conjugated pneumococcal saccharides, and one or more pneumococcal proteins of the invention In addition, pneumococcal saccharides and proteins can be stably stored as bulk components adsorbed onto aluminium phosphate in a liquid form.

In another aspect of the invention, the vaccine composition may comprise a human cytomegalovirus (HCMV) antigen. HCMV is a human DNA virus belonging to the family of herpes viruses, and is a major cause of congenital defects in newborns and also causes serious medical conditions in immunocompromised patients. Clinical disease causes a variety of symptoms including fever, hepatitis, pneumonitis and infectious mononucleosis.

In one embodiment, the HCMV antigen is a chimeric fusion protein or an immunogenic derivative thereof comprising a portion of an HCMV glycoprotein fused to a portion of an HSV glycoprotein. The HCMV glycoprotein is typically gB, and the HSV glycoprotein is typically gD, in particular HSV type 2 gD (gD2). The fusion is typically between an amino acid in the N-terminal part of a portion of the HCMV gB protein and an amino acid at the C terminus of a portion of the HSV gD protein. Both the HCMV gB protein and the HSV gD protein components of the fusion protein may lack a membrane anchor domain.

The portion of the HCMV gB protein may comprise a non-cleavable form of HCMV gB. Suitably this is achieved by changing one or more amino acids at a cleavage site of the protein, for example by exchanging Arg458 and Arg459 for Glu and Thr, respectively. The portion of the HSV protein may comprise the signal sequence of gD2 (amino acids 1 to 25) and optionally amino acids 26 to 52 of gD2 and/or the sequence from gD2 which is PEDSALLEDPED (SEQ ID NO 1) or functionally equivalents thereof, which may be shorter or longer. Further sequences from HSV gD may be added to the fusion protein, for example at the C terminus of the HCMV gB protein.

In one embodiment, the fusion protein comprises amino acids 1 to 52 of the HSV gD2 protein fused to residues 28 to 685 of the HCMV gB protein. Such a fusion protein is designated HCMV gB685*. In a further embodiment, the amino acid sequence PEDSALLEDPED (SEQ ID NO 1), which is derived from an internal gD2 sequence, may be included at the C terminal end of the protein HCMV gB685* to produce the protein designated HCMV gB685**. These specific fusion proteins are described in more detail in WO 95/31555.

Another immunogen suitable for use as an HCMV vaccine is pp65, an HCMV matrix protein as described in WO 94/00150 (City of Hope).

In a further embodiment of the present invention, immunogenic compositions contain an antigen or antigenic preparation derived from the Human Papilloma Virus (HPV) considered to be responsible for genital warts (HPV 6 or HPV 11 and others), and/or the HPV viruses responsible for cervical cancer (HPV16, HPV18 and others).

In one embodiment the forms of genital wart prophylactic, or therapeutic, compositions comprise L1 particles or capsomers, and fusion proteins comprising one or more antigens selected from the HPV proteins E1, E2, E5 E6, E7, L1, and L2.

In one embodiment the forms of fusion protein are: L2E7 as disclosed in WO 96/26277, and proteinD(⅓)-E7 disclosed in GB 9717953.5 (PCT/EP98/05285).

A preferred HPV cervical infection or cancer, prophylactic or therapeutic composition may comprise HPV 16 or 18 antigens. For example, L1 or L2 antigen monomers, or L1 or L2 antigens presented together as a virus like particle (VLP) or the L1 protein alone presented in a VLP or caposmer structure. Such antigens, virus like particles and capsomers are per se known. See for example WO94/00152, WO94/20137, WO94/05792, and WO93/02184.

Additional early proteins may be included alone or as fusion proteins such as E7, E2 or preferably E5 for example; particularly preferred embodiments of this includes a VLP comprising L1E7 fusion proteins (WO 96/11272).

In one embodiment the HPV 16 antigens comprise the early proteins E6 or E7 in fusion with a protein D carrier to form Protein D—E6 or E7 fusions from HPV 16, or combinations thereof; or combinations of E6 or E7 with L2 (WO 96/26277).

Alternatively the HPV 16 or 18 early proteins E6 and E7, may be presented in a single molecule, preferably a Protein D-E6/E7 fusion. Such a composition may optionally contain either or both E6 and E7 proteins from HPV 18, preferably in the form of a Protein D-E6 or Protein D-E7 fusion protein or Protein D E6/E7 fusion protein.

The composition of the present invention may additionally comprise antigens from other HPV types, preferably from HPV 31 or 33.

Oncogenic HPV types include HPV 31, 33, 35, 39, 45, 51, 52, 56, 58, 59, 66 and 68. Thus the composition of the present invention may comprise antigens from one or more of these HPV types, in addition to HPV 16 and/or HPV 18.

HPV L1 VLPs or capsomers useful in the invention may comprise or consist of full length L1 or an immunogenic fragment of L1. Where the VLP or capsomer comprises or consists of an immunogenic fragment of L1, then suitable immunogenic fragments of HPV L1 include truncations, deletions, substitution, or insertion mutants of L1. Such immunogenic fragments are suitably capable of raising an immune response, said immune response being capable of recognising an L1 protein such as a virus like particle, from the HPV type from which the L1 protein was derived.

Suitable immunogenic L1 fragments include truncated L1 proteins. In one aspect the truncation removes a nuclear localisation signal. In another aspect the truncation is a C terminal truncation. In a further aspect the C terminal truncation removes fewer than 50 amino acids, such as fewer than 40 amino acids. Where the L1 is from HPV 16 then in another aspect the C terminal truncation removes 34 amino acids from HPV 16 L1. Where the L1 is from HPV 18 then in a further aspect the C terminal truncation removes 35 amino acids from HPV 18 L1.

Suitable truncated HPV 16 and 18 L1 sequences are given in WO 06/114312.

The HPV 16 sequence may also be that disclosed in WO9405792 or U.S. Pat. No. 6,649,167, for example, suitably truncated. Suitable truncates are truncated at a position equivalent to that discussed above, as assessed by sequence comparison.

An alternative HPV 18 sequence is disclosed in WO9629413, which may be suitably truncated. Suitable truncates are truncated at a position equivalent to that described above, as assessed by sequence comparison.

Other HPV 16 and HPV 18 sequences are well known in the art and may be suitable for use in the present invention.

Where there is an L1 protein from another HPV type then C terminal truncations corresponding to those made for HPV 16 and HPV 18 may be used, based upon DNA or protein sequence alignments. Suitable truncations of HPV 31 and 45 L1 proteins are given in WO 06/114312.

Suitable truncations of, for example, HPV 31, 33, 35, 39, 45, 51, 52, 56, 58, 59, 66 and 68 may also be made, in one aspect removing equivalent C terminal portions of the L1 protein to those described above, as assessed by sequence alignment.

The L1 protein or immunogenic fragment of the invention may optionally be in the form of a fusion protein, such as the fusion of the L1 protein with L2 or an early protein.

The HPV L1 protein is suitably in the form of a capsomer or virus like particle (VLP). In one aspect HPV VLPs may be used in the present invention. HPV VLPs and methods for the production of VLPs are well known in the art. VLPs typically are constructed from the L1 and optionally L2 structural proteins of the virus, see for example WO9420137, U.S. Pat. No. 5,985,610, WO9611272, U.S. Pat. Nos. 6,599,508B1, 6,361,778B1, EP 595935. Any suitable HPV VLP may be used in the present invention which provides cross protection, such as an L1 or L1+L2 VLP. Suitably the VLP is an L1-only VLP.

The composition of the invention may contain a combination of HPV 16 L1 VLPs and HPV 18 L1 VLPs, or a combination of HPV L1 VLPs from HPV 16, 18, 31 and 45, or larger combinations, and includes HPV 16 and 18 or HPV 16, 18, 31 and 45 L1 VLPs, or large combinations, wherein the L1 is optionally truncated as described herein.

In a particular embodiment of the invention, one or more additional antigens from cancer-causing HPV types are used with HPV 16 and/or 18 antigens, the antigens being selected from the following HPV types: HPV 31, 45, 33, 58 and 52. As described herein, the antigen may in each case be L1 for example in the form of L1 VLPs or capsomers. Thus HPV antigens for use in the compositions, methods and uses described herein may comprise or consist of L1 VLPs or capsomers from HPV 16, 18, 31, 45, 33, 58 and 52. The L1 VLPs may be L1-only VLPs or in combination with another antigen such as L2 in L1+L2 VLPs. The L1 protein may suitably be truncated as described herein.

VLP formation can be assessed by standard techniques such as, for example, electron microscopy and dynamic laser light scattering.

The VLP may comprise full length L1 protein. In one aspect the L1 protein used to form the VLP is a truncated L1 protein, as described above.

VLPs may be made in any suitable cell substrate such as yeast cells or insect cells e.g. in a baculovirus expression system, and techniques for preparation of VLPs are well known in the art, such as WO9913056, U.S. Pat. Nos. 6,416,945B1, 6,261,765B1 and 6,245,568, and references therein, the entire contents of which are hereby incorporated by reference.

VLPS may be made by disassembly and reassembly techniques, which can provide for more stable and/or homogeneous papillomavirus VLPs. For example, McCarthy et al, 1998 "Quantitative Disassembly and Reassembly of Human Papillomavirus Type 11 Virus like Particles in Vitro" J. Virology 72(1):33-41, describes the disassembly and reassembly of recombinant L1 HPV 11 VLPs purified from insect cells in order to obtain a homogeneous preparation of VLP's. WO9913056 and U.S. Pat. No. 6,245,568 also describe disassembly/reassembly processes for making HPV VLPs.

In one aspect HPV VLPS are made as described WO9913056 or U.S. Pat. No. 6,245,568

Compositions of the present invention may comprise antigens or antigenic preparations derived from parasites that cause Malaria such as *Plasmodium falciparum* or *Plasmodium vivax*. For example, possible antigens derived from *Plasmodium falciparum* include circumsporozoite protein (CS protein), RTS,S MSP1, MSP3, LSA1, LSA3, AMA1 and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published under Number WO 93/10152 claiming priority from UK patent application No. 9124390.7. When expressed in yeast RTS is produced as a lipoprotein particle, and when it is co-expressed with the S antigen from HBV it produces a mixed particle known as RTS,S. TRAP antigens are described in the International Patent Application No. PCT/GB89/00895, published under WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, Pfs27/25, Pfs16, Pfs48/45, Pfs230 and their analogues in *Plasmodium* spp. One embodiment of the present invention is a composition comprising RTS,S or CS protein or a fragment thereof such as the CS portion of RTS,S in combination with one or more further malarial antigens which may be selected for example from the group consisting of MSP1, MSP3, AMA1, LSA1 or LSA3. Possible antigens from *P. vivax* include circumsporozoite protein (CS protein) and Duffy antigen binding protein and fragments thereof, such as PvRII (see e.g. WO02/12292).

Other possible antigens that may be used in the immunogenic compositions of the present invention include:

Streptococcal antigens such as from Group A *Streptococcus*, or Group B *Streptococcus*, antigens are suitably derived from HIV-1, (such as F4 antigen or fragments thereof or gag or fragments thereof such as p24, tat, nef, gp120 or gp160 or fragments of any of these), human herpes viruses, such as gD or derivatives thereof or Immediate Early protein such as ICP27 from HSV1 or HSV2, cytomegalovirus ((esp Human) (such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F, N and G proteins or derivatives thereof), parainfluenza virus, measles virus, mumps virus, human papilloma viruses (for example HPV6, 11, 16, 18), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by R. Gluck, Vaccine, 1992, 10, 915-920) or purified or recombinant proteins thereof, such as HA, NP, NA, or M proteins, or combinations thereof), or derived from bacterial pathogens such as *Neisseria* spp, including *N. gonorrhea* and *N. meningitidis* (for example capsular saccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans; H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P.* aeruginosa; *Staphylococcus* spp., including *S. aureus, S. epidermidis; Enterococcus* spp., including *E. faecalis, E. faecium; Clostridium* spp., including *C. tetani* (for example tetanus toxin and derivatives thereof), *C. botulinum* (for example botulinum toxin and derivatives thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheria* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp., including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. carinii; Trichomonas* spp., including *T. vaginalis; Schisostoma* spp., including *S. mansoni*, or derived from yeast such as *Candida* spp., including *C. albicans; Cryptococcus* spp., including *C. neoformans*.

Other preferred specific antigens for *M. tuberculosis* are for example Tb Ra12, Tb H9, Tb Ra35, Tb38-1, Erd 14, DPV, MTI, MSL, mTTC2 and hTCC1 (WO 99/51748), Mtb72F and M72. Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI (WO 99/51748). A particular Ra12-Tbh9-Ra35 sequence that may be mentioned is defined by SEQ ID No 6 of WO2006/117240 together with variants in which Ser 704 of that sequence is mutated to other than serine, e.g. to Ala, and derivatives thereof incorporating an N-terminal His tag of an appropriate length (e.g. SEQ ID No 2 or 4 of WO2006/117240)".

Exemplary antigens for *Chlamydia* species, e.g., *C. trachomatis*, are selected from CT858, CT089, CT875, MOMP, CT622, PmpD, PmpG and fragments thereof, SWIB and immunogenic fragments of any one thereof (such as PmpDpd and PmpGpd) and combinations thereof. Preferred combinations of antigens include CT858, CT089 and CT875. Specific sequences and combinations that may be employed are described in WO2006/104890. Preferred bacterial compositions comprise antigens derived from *Haemophilus* spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Derivatives of Hepatitis B Surface antigen are well known in the art and include, inter alia, those PreS1, PreS2 S antigens set forth described in European Patent applications EP-A-414 374; EP-A-0304 578, and EP 198-474. In one preferred aspect the vaccine formulation of the invention comprises the HIV-1 antigen, gp120, especially when expressed in CHO cells. In a further embodiment, the composition of the invention comprises gD2t as hereinabove defined.

The compositions may also contain an anti-tumour antigen and be useful for the immunotherapeutic treatment of cancers. For example, the antigen may be a tumour rejection antigen such as those for prostate, breast, colorectal, lung, pancreatic, renal or melanoma cancers. Exemplary antigens include MAGE 1, 3 and MAGE 4 or other MAGE antigens such as disclosed in WO99/40188, PRAME, BAGE, Lage (also known as NY Eos 1) SAGE and HAGE (WO 99/53061) or GAGE (Robbins and Kawakami, 1996, Current Opinions in Immunology 8, pps 628-636; Van den Eynde et al., International Journal of Clinical & Laboratory Research (submitted 1997); Correale et al. (1997), Journal of the National Cancer Institute 89, p293. Indeed these antigens are expressed in a wide range of tumour types such as melanoma, lung carcinoma, sarcoma and bladder carcinoma.

MAGE antigens for use in the present invention may be expressed as a fusion protein with an expression enhancer or an Immunological fusion partner. In particular, the Mage protein may be fused to Protein D from *Haemophilus infuenzae* B or a lapidated derivative thereof. In particular, the fusion partner may comprise the first ⅓ of Protein D. Such constructs are disclosed in WO99/40188.

Other tumour-specific antigens include, but are not restricted to KSA (GA733) tumour-specific gangliosides such as GM 2, and GM3 or conjugates thereof to carrier proteins; or said antigen may be a self peptide hormone such as whole length Gonadotrophin hormone releasing hormone (GnRH, WO 95/20600), a short 10 amino acid long peptide, useful in the treatment of many cancers, or in immunocastration.

In a preferred embodiment prostate antigens are utilised, such as Prostate specific antigen (PSA), PAP, PSCA (PNAS 95(4) 1735-1740 1998), PSMA or antigen known as Prostase. Prostase is a prostate-specific serine protease (trypsin-like), 254 amino acid-long, with a conserved serine protease catalytic triad H-D-S and a amino-terminal pre-propeptide sequence, indicating a potential secretory function (P. Nelson, Lu Gan, C. Ferguson, P. Moss, R. Gelinas, L. Hood & K. Wand, "Molecular cloning and characterisation of prostase, an androgen-regulated serine protease with prostate restricted expression, In Proc. Natl. Acad. Sci. USA (1999) 96, 3114-3119). A putative glycosylation site has been described. The predicted structure is very similar to other known serine proteases, showing that the mature polypeptide folds into a single domain. The mature protein is 224 amino acids-long, with one A2 epitope shown to be naturally processed.

Prostase nucleotide sequence and deduced polypeptide sequence and homologs are disclosed in Ferguson, et al. (Proc. Natl. Acad. Sci. USA 1999, 96, 3114-3119) and in International Patent Applications No. WO 98/12302 (and also the corresponding granted patent U.S. Pat. No. 5,955, 306), WO 98/20117 (and also the corresponding granted patents U.S. Pat. Nos. 5,840,871 and 5,786,148) (prostate-specific kallikrein) and WO 00/04149 (P703P).

The present invention provides compositions comprising prostase protein fusions based on prostase protein and fragments and homologues thereof ("derivatives"). Such derivatives are suitable for use in therapeutic vaccine formulations which are suitable for the treatment of a prostate tumours. Typically the fragment will contain at least 20, preferably 50, more preferably 100 contiguous amino acids as disclosed in the above referenced patent and patent applications.

A further preferred prostate antigen is known as P501S, sequence ID no 113 of Wo98/37814. Immunogenic fragments and portions thereof comprising at least 20, preferably 50, more preferably 100 contiguous amino acids as disclosed in the above referenced patent application. See for example PS108 (WO 98/50567).

Other prostate specific antigens are known from Wo98/37418, and WO/004149. Another is STEAP PNAS 96 14523 14528 7-12 1999.

Other tumour associated antigens useful in the context of the present invention include: Plu—1 J Biol. Chem 274 (22) 15633-15645, 1999, HASH-1, HasH-2, Cripto (Salomon et al Bioessays 199, 21 61-70,U.S. Pat. No. 5,654,140) Criptin U.S. Pat. No. 5,981,215. Additionally, antigens particularly relevant for therapy of cancer also comprise tyrosinase and survivin. Mucin derived peptides such as Muc1 see for example U.S. Pat. Nos. 5,744,144 5,827,666 WO 8805054, U.S. Pat. No. 4,963,484. Specifically contemplated are Muc 1 derived peptides that comprise at least one repeat unit of the Muc 1 peptide, preferably at least two such repeats and which is recognised by the SM3 antibody (U.S. Pat. No. 6,054,438). Other mucin derived peptides include peptide from Muc 5.

The antigen of the invention may be a breast cancer antigens such as her 2/Neu, mammaglobin (U.S. Pat. No. 5,668,267) or those disclosed in WO/00 52165, WO99/33869, WO99/19479, WO 98/45328. Her 2 neu antigens are disclosed inter alia, in U.S. Pat. No. 5,801,005. Preferably the Her 2 neu comprises the entire extracellular domain (comprising approximately amino acid 1-645) or fragments thereof and at least an immunogenic portion of or the entire intracellular domain approximately the C terminal 580 amino acids. In particular, the intracellular portion should comprise the phosphorylation domain or fragments thereof. Such constructs are disclosed in WO00/44899. A particularly preferred construct is known as ECD PD a second is known as ECD PD See Wo/00/44899. The her 2 neu as used herein can be derived from rat, mouse or human.

The compositions may contain antigens associated with tumour-support mechanisms (e.g. angiogenesis, tumour invasion) for example tie 2, VEGF.

It is foreseen that compositions of the present invention may use antigens derived from *Borrelia* sp. For example, antigens may include nucleic acid, pathogen derived antigen or antigenic preparations, recombinantly produced protein or peptides, and chimeric fusion proteins. In particular the antigen is OspA. The OspA may be a full mature protein in a lipidated form virtue of the host cell (*E. coli*) termed (Lipo-OspA) or a non-lipidated derivative.Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Compositions of the present invention may be used for the prophylaxis or therapy of allergy. Such vaccines would comprise allergen specific (for example Der p1) and allergen non-specific (for example peptides derived from human IgE, including but not restricted to the stanworth decapeptide (EP 0 477 231 B1)).

Compositions of the present invention may also be used for the prophylaxis or therapy of chronic disorders others than allergy, cancer or infectious diseases. Such chronic disorders are diseases such as atherosclerosis, and Alzheimer.

The compositions of the present invention are particularly suited for the immunotherapeutic treatment of diseases, such as chronic conditions and cancers, but also for the therapy of persistent infections. Accordingly the compositions of the present invention are particularly suitable for the immunotherapy of infectious diseases, such as Tuberculosis (TB), AIDS and Hepatitis B (HepB) virus infections.

Also, in the context of AIDS, there is provided a method of treatment of an individual susceptible to or suffering from AIDS. The method comprising the administration of a vaccine of the present invention to the individual, thereby reducing the amount of CD4+ T-cell decline caused by subsequent HIV infection, or slowing or halting the CD4+ T-cell decline in an individual already infected with HIV.

Other antigens include bacterial (preferably capsular) saccharides other than (or in addition to) those pneumococcal antigens described above. Polysaccharide antigens are conveniently stored in liquid bulk adsorbed onto aluminium phosphate—it is therefore straightforward to generate vaccine compositions of the invention by admixing said liquid bulk with the adjuvant of the invention extemporaneously. Preferably the other bacterial saccharides are selected from a group consisting of: *N. meningitidis* serogroup A capsular saccharide (MenA), *N. meningitidis* serogroup C capsular saccharide (MenC), *N. meningitidis* serogroup Y capsular saccharide (MenY), *N. meningitidis* serogroup W-135 capsular saccharide (MenW), Group B *Streptococcus* group I capsular saccharide, Group B *Streptococcus* group II capsular saccharide, Group-B *Streptococcus* group III capsular saccharide, Group B *Streptococcus* group IV capsular saccharide, Group B *Streptococcus* group V capsular saccharide, *Staphylococcus aureus* type 5 capsular saccharide, *Staphylococcus aureus* type 8 capsular saccharide, Vi saccharide from *Salmonella typhi*, *N. meningitidis* LPS, *M. catarrhalis* LPS, and *H. influenzae* LPS. By LPS it is meant either native lipo-polysaccharide (or lipo-oligosaccharide), or lipo-polysaccharide where the lipid A portion has been detoxified by any of a number of known methods (see for example WO 97/18837 or WO 98/33923), or any molecule comprising the 0-polysaccharide derived from said LPS. By *N. meningitidis* LPS it is meant one or more of the 12 known immunotypes (L1, L2, L3, L4, L5, L6, L7, L8, L9, L10, L11 or L12).

Particularly preferred combinations are compositions comprising: 1) conjugated Hib, conjugated MenA and conjugated MenC; 2) conjugated Hib, conjugated MenY and conjugated MenC; 3) conjugated Hib and conjugated MenC; and 4) conjugated MenA, conjugated MenC, conjugated MenY and conjugated MenW-135. The amount of PS in each of the above conjugates may be 5 or 10 □g each per 0.5 mL human dose. Preferably Hib, MenA, MenC, MenW-135 and MenY are TT conjugates.

A problem associated with the polysaccharide approach to vaccination, is the fact that polysaccharides per se are poor immunogens. To overcome this, saccharides of the invention may be conjugated to protein carriers, which provide bystander T-cell help. It is preferred, therefore, that the saccharides utilised in the invention are linked to such a protein carrier. Examples of such carriers which are currently commonly used for the production of saccharide immunogens include the Diphtheria and Tetanus toxoids (DT, DT CRM197 and TT respectively), Keyhole Limpet Haemocyanin (KLH), protein D from *Haemophilus influen-* zae (EP 594610-B), OMPC from *N. meningitidis*, and the purified protein derivative of Tuberculin (PPD).

The saccharide may be linked to the carrier protein by any known method (for example, by Likhite, U.S. Pat. No. 4,372,945 and by Armor et al., U.S. Pat. No. 4,474,757). Preferably, CDAP conjugation is carried out (WO 95/08348).

Preferably the protein:saccharide (weight:weight) ratio of the conjugates is 0.3:1 to 1:1, more preferably 0.6:1 to 0.8:1, and most preferably about 0.7:1.

Combinations of antigens which provide protection against pneumococcus and a different pathogen are included in the present invention. Many Paediatric vaccines are now given as a combination vaccine so as to reduce the number of injections a child has to receive. Thus for Paediatric vaccines other antigens from other pathogens may be formulated with the pneumococcal vaccines of the invention. For example the vaccines of the invention can be formulated with (or administered separately but at the same time) the well known 'trivalent' combination vaccine comprising Diphtheria toxoid (DT), tetanus toxoid (TT), and pertussis components [typically detoxified Pertussis toxoid (PT) and filamentous haemagglutinin (FHA) with optional pertactin (PRN) and/or agglutinin 1+2], for example the marketed vaccine INFANRIX-DTPa™ (SmithKlineBeecham Biologicals) which contains DT, TT, PT, FHA and PRN antigens, or with a whole cell pertussis component for example as marketed by SmithKlineBeecham Biologicals s.a., as Tritanrix™. The combined vaccine may also comprise other antigen, such as Hepatitis B surface antigen (HBsAg), Polio virus antigens (for instance inactivated trivalent polio virus—IPV), *Moraxella catarrhalis* outer membrane proteins, non-typeable *Haemophilus influenzae* proteins, *N. meningitidis* B outer membrane proteins.

Examples of preferred *Moraxella catarrhalis* protein antigens which can be included in a combination vaccine (especially for the prevention of otitis media) are: OMP106 [WO 97/41731 (Antex) & WO 96/34960 (PMC)]; OMP21; LbpA &/or LbpB [WO 98/55606 (PMC)]; TbpA &/or TbpB [WO 97/13785 & WO 97/32980 (PMC)]; CopB [Helminen M E, et al. (1993) Infect. Immun. 61:2003-2010]; UspA1 and/or UspA2 [WO 93/03761 (University of Texas)]; OmpCD; HasR (PCT/EP99/03824); PilQ (PCT/EP99/03823); OMP85 (PCT/EP00/01468); lipo06 (GB 9917977.2); lipo10 (GB 9918208.1); lipo11 (GB 9918302.2); lipo18 (GB 9918038.2); P6 (PCT/EP99/03038); D15 (PCT/EP99/03822); OmpIA1 (PCT/EP99/06781); Hly3 (PCT/EP99/03257); and OmpE. Examples of non-typeable *Haemophilus influenzae* antigens which can be included in a combination vaccine (especially for the prevention of otitis media) include: Fimbrin protein [(U.S. Pat. No. 5,766,608—Ohio State Research Foundation)] and fusions comprising peptides therefrom [e.g. LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and/or TbpB; Hia; Hsf; Hin47; Hit Hmw1; Hmw2; Hmw3; Hmw4; Hap; D15 (WO 94/12641); protein D (EP 594610); P2; and P5 (WO 94/26304).

Other combinations contemplated are the pneumococcal saccharide & protein of the invention in combination with viral antigens, for example, from influenza (attenuated, split, or subunit [e.g., surface glycoproteins neuraminidase (NA) and haemagglutinin (HA). See, e.g., Chaloupka I. et al, Eur. Journal Clin. Microbiol. Infect. Dis. 1996, 15:121-127], RSV (e.g., F and G antigens or F/G fusions, see, e.g., Schmidt A. C. et al, J Virol, May 2001, p4594-4603), PIV3 (e.g., HN and F proteins, see Schmidt et al. supra), Varicella (e.g., attenuated, glycoproteins I-V, etc.), and any (or all) component(s) of MMR (measles, mumps, rubella).

A preferred Paediatric combination vaccine contemplated by the present invention for global treatment or prevention of otitis media comprises: one or more *Streptococcus pneumoniae* saccharide antigen(s) (preferably conjugated to protein D), one or more pneumococcal proteins (preferably those described above), and one or more surface-exposed antigen from *Moraxella catarrhalis* and/or non-typeable *Haemophilus influenzae*. Protein D can advantageously be used as a protein carrier for the pneumococcal saccharides (as mentioned above), and because it is in itself an immunogen capable of producing B-cell mediated protection against non-typeable *H. influenzae* (ntHi). The *Moraxella catarrhalis* or non-typeable *Haemophilus influenzae* antigens can be included in the vaccine in a sub-unit form, or may be added as antigens present on the surface of outer membrane vesicles (blebs) made from the bacteria.

Immunogenic Properties of the Immunogenic Composition Used for the Vaccination of the Present Invention In the present invention the immunogenic composition is preferably capable of inducing an improved CD4 T-cell immune response against at least one of the component antigen(s) or antigenic composition compared to the CD4 T-cell immune response obtained with the corresponding composition which in un-adjuvanted, i.e. does not contain any exogeneous adjuvant (herein also referred to as 'plain composition'). In a specific embodiment, where the immunogenic composition is an influenza composition and where the influenza vaccine preparation is from several influenza strains, one of which being a pandemic starin, said improved CD4 T-cell immune response is against the pandemic influenza strain.

By "improved CD4 T-cell immune response" is meant that a higher CD4 response is obtained in a mammal after administration of the adjuvanted immunogenic composition than that obtained after administration of the same composition without adjuvant. For example, a higher CD4 T-cell response is obtained in a human patient upon administration of an immunogenic composition comprising an influenza virus or antigenic preparation thereof together with adjuvant according to the invention, compared to the response induced after administration of an immunogenic composition comprising an influenza virus or antigenic preparation thereof which is un-adjuvanted. Such formulation will advantageously be used to induce anti-influenza CD4-T cell response capable of detection of influenza epitopes presented by MHC class II molecules.

In particular but not exclusively, said 'improved CD4 T-cell immune response' is obtained in an immunologically unprimed patient, i.e. a patient who is seronegative to said influenza virus or antigen. This seronegativity may be the result of said patient having never faced such virus or antigen (so-called 'naive' patient) or, alternatively, having failed to respond to said antigen once encountered. In a specific aspect said CD4 T-cell immune response is obtained in an immunocompromised subject such as an elderly, typically 65 years of age or above, or an adult younger than 65 years of age with a high risk medical condition (high risk' adult), or a child under the age of two.

The improved CD4 T-cell immune response may be assessed by measuring the number of cells producing any of the following cytokines:

cells producing at least two different cytokines (CD40L, IL-2, IFNγ, TNFα)

cells producing at least CD40L and another cytokine (IL-2, TNFα, IFNγ)

cells producing at least IL-2 and another cytokine (CD40L, TNFα, IFNγ)

cells producing at least IFNγ and another cytokine (IL-2, TNFα, CD40L)

cells producing at least TNFα and another cytokine (IL-2, CD40L, IFNγ)

There will be improved CD4 T-cell immune response when cells producing any of the above cytokines will be in a higher amount following administration of the adjuvanted composition compared to the administration of the un-adjuvanted composition. Typically at least one, preferably two of the five conditions mentioned herein above will be fulfilled. In a particular embodiment, the cells producing all four cytokines will be present at a higher amount in the adjuvanted group compared to the un-adjuvanted group.

The improved CD4 T-cell immune response conferred by an adjuvanted influenza composition of the present invention may be ideally obtained after one single administration. The single dose approach will be extremely relevant for example in a rapidly evolving outbreak situation. In certain circumstances, especially for the elderly population, or in the case of young children (below 9 years of age) who are vaccinated for the first time against influenza, or in the case of a pandemics, it may be beneficial to administer two doses of the same composition for that season. The second dose of said same composition (still considered as 'composition for first vaccination') may be administered during the on-going primary immune response and is adequately spaced. Typically the second dose of the composition is given a few weeks, or about one month, e.g. 2 weeks, 3 weeks, 4 weeks, 5 weeks, or 6 weeks after the first dose, to help prime the immune system in unresponsive or poorly responsive individuals.

In another embodiment, the administration of said immunogenic composition induces an improved B-memory cell response in patients administered with the adjuvanted immunogenic composition compared to the B-memory cell response induced in individuals immunized with the un-adjuvanted composition. An improved B-memory cell response is intended to mean an increased frequency of peripheral blood B lymphocytes capable of differentiation into antibody-secreting plasma cells upon antigen encounter as measured by stimulation of in-vitro differentiation.

In another embodiment, the administration of said immunogenic composition induces an improved humoral response in patients administered with the adjuvanted immunogenic composition compared to the humoral response induced in individuals immunized with the un-adjuvanted composition. Said humoral immune response may be measured according to any of the procedure detailed in Example I, and especially in sections I.1 (I.1.1), I.2 (I.2.1) and I.3 (I.3.5.2). When the immunogenic composition is an influenza composition specifically said humoral response is obtained against homologous and heterologous strains. In particular, said heterologous humoral immune response means a humoral response between influenza strains, and is termed 'cross-reactive' humoral immune response. Said 'cross-reactive' humoral immune response involves the induction of response against an influenza strain which is a variant (a drift) of the influenza strain used for vaccination. An example of such a response is illustrated in Example III.3.1 and in FIG. 2.

In a specific embodiment, the administration of said adjuvanted immunogenic composition induces at least two of the following responses: (i) an improved CD4 T-cell immune response, (ii) an improved B-memory cell response, (iii) an improved humoral response, against at least one of the component antigen(s) or antigenic composition compared to either immune response obtained with the corresponding composition which in un-adjuvanted, i.e. does not contain any exogeneous adjuvant (herein also referred to as 'plain composition').

In a still further specific embodiment, the vaccination with the composition for the first vaccination, adjuvanted, has no measurable impact on the CD8 response.

It is a specific embodiment of the invention that the composition comprising an influenza virus or antigenic preparation thereof formulated with saponin adjuvant presented in the form of a liposome, in particular QS21 saponin in its quenched form with cholesterol, is effective in promoting T cell responses in an immuno-compromised human population. In one embodiment, said adjuvant further comprises 3D-MPL. In particular, the administration of a single dose of the immunogenic composition for first vaccination as described in the invention, is capable of providing better sero-protection, as assessed by the correlates of protection for influenza vaccines, following revaccination against influenza in a human elderly population, than does the vaccination with an un-adjuvanted influenza vaccine. The claimed adjuvanted formulation has also been able to induce an improved CD4 T-cell immune response against influenza virus compared to that obtained with the un-adjuvanted formulation. This finding can be associated with an increased responsiveness upon vaccination or infection vis-à-vis influenza antigenic exposure. Furthermore, this may also be associated with a cross-responsiveness, i.e. a higher ability to respond against variant influenza strains. This improved response may be especially beneficial in an immuno-compromised human population such as the elderly population (65 years of age and above) and in particular the high risk elderly population. This may result in reducing the overall morbidity and mortality rate and preventing emergency admissions to hospital for pneumonia and other influenza-like illness. This may also be of benefit to the infant population (below 5 years, preferably below 2 years of age). Furthermore it may allow inducing a CD4 T cell response which is more persistent in time, e.g. still present one year after the first vaccination, compared to the response induced with the un-adjuvanted formulation.

In a specific aspect, the CD4 T-cell immune response, such as the improved CD4 T-cell immune response obtained in an unprimed subject, involves the induction of a cross-reactive CD4 T helper response. In particular, the amount of cross-reactive CD4 T cells is increased. By 'cross-reactive' CD4 response is meant CD4 T-cell targeting shared epitopes between influenza strains.

Usually, available influenza vaccines are effective only against infecting strains of influenza virus that have haemagglutinin of similar antigenic characteristics. When the infecting (circulating) influenza virus has undergone minor changes (such as a point mutation or an accumulation of point mutations resulting in amino acid changes in the for example) in the surface glycoproteins in particular haemagglutinin (antigenic drift variant virus strain) the vaccine may still provide some protection, although it may only provide limited protection as the newly created variants may escape immunity induced by prior influenza infection or vaccination. Antigenic drift is responsible for annual epidemics that occur during interpandemic periods (Wiley & Skehel, 1987, Ann. Rev. Biochem. 56, 365-394). The induction of cross-reactive CD4 T cells provides an additional advantage to the composition of the invention, in that it may provide also cross-protection, in other words protection against heterologous infections, i.e. infections caused by a circulating influenza strain which is a variant (e.g. a drift) of the influenza strain contained in the immunogenic composition. This may be advantageous when the circulating strain is difficult to propagate in eggs or to produce in cell culture, rendering the use of a drifted strain a working alternative. This may also be advantageous when the subject received a first and a second vaccination several months or a year apart, and the influenza strain in the immunogenic composition used for a second immunization is a drift variant strain of the strain used in the composition used for the first vaccination.

The adjuvanted influenza immunogenic composition as herein defined has therefore a higher ability to induce sero-protection and cross-reactive CD4 T cells in vaccinated elderly subjects. This characteristic may be associated with a higher ability to respond against a variant strain of the strain present in the immunogenic composition. This may prove to be an important advantage in a pandemic situation. For example a multivalent influenza immunogenic composition comprising any or several of H5, a H2, a H9, H7 or H6 strain(s) may provide a higher ability to respond against a pandemic variant, i.e. a drift strain of said pandemic strain(s), either upon subsequent vaccination with or upon infection by said drift strain.

Detection of Cross-reactive CD4 T-cells Following Vaccination with Influenza Vaccine CD4 T-cells that are able to recognize both homologous and drifted Influenza strains have been named in the present document "cross-reactive". The adjuvanted influenza compositions as described herein have been capable to show heterosubtypic cross-reactivity since there is observable cross-reactivity against drifted Influenza strains. As said above, the ability of a pandemic vaccine formulation to be effective against drift pandemic strains may prove to be an important characteristic in the case of pandemics.

Consistently with the above observations, CD4 T-cell epitopes shared by different Influenza strains have been identified in human (Gelder C et al. 1998, Int Immunol. 10(2):211-22; Gelder C M et al. 1996 J Virol. 70(7):4787-90; Gelder C M et al. 1995 J Virol. 1995 69(12) :7497-506).

In a specific embodiment, the adjuvanted composition may offer the additional benefit of providing better protection against circulating strains which have undergone a major change (such as gene recombination for example, between two different species) in the haemagglutinin (antigenic shift) against which currently available vaccines have no efficacy.

Revaccination and Composition Used for Revaccination (Boosting Composition)

In one embodiment, the invention provides for the use of an influenza virus or antigenic preparation thereof in the manufacture of an immunogenic composition for revaccination of humans previously vaccinated with an immunogenic composition as claimed herein.

In one aspect of the present invention, there is provided the use of an influenza virus or antigenic preparation thereof, from a first pandemic influenza strain, in the manufacture of an adjuvanted immunogenic composition as herein defined for protection against influenza infections caused by a influenza strain which is a variant of said first influenza strain.

In another aspect, the invention provides for the use of an influenza virus or antigenic preparation thereof in the manufacture of an influenza immunogenic composition for revaccination of humans previously vaccinated with an adjuvanted influenza composition as claimed herein or with an adjuvanted influenza composition comprising a variant influenza strain, the adjuvant being as defined herein.

In another aspect the present invention provides for a method for vaccinating a human population or individual against one influenza virus strain followed by revaccination of said human or population against a variant influenza virus strain, said method comprising administering to said human (i) a first composition comprising an influenza virus or antigenic preparation thereof from a first influenza virus strain and an adjuvant as herein defined, and (ii) a second immunogenic composition comprising a influenza virus strain variant of said first influenza virus strain. In a specific embodiment said first strain is associated with a pandemic outbreak or has the potential to be associated with a pandemic outbreak. In another specific embodiment said variant strain is associated with a pandemic outbreak or has the potential to be associated with a pandemic outbreak. In particular, the re-vaccination is made with an influenza composition comprising at least one strain which is a circulating pandemic strain. Both the priming composition and the boosting composition can be multivalent, i.e. can contain at least two influenza virus strains. When the composition(s) is (are) multivalent, at least one strain is associated with a pandemic outbreak or has the potential to be associated with a pandemic outbreak.

Typically revaccination is made at least 6 months after the first vaccination(s), preferably 8 to 14 months after, more preferably at around 10 to 12 months after.

The immunogenic composition for revaccination (the boosting composition) may contain any type of antigen preparation, either inactivated or live attenuated. It may contain the same type of antigen preparation e.g. a split influenza virus or antigenic preparation thereof, a whole virion, or a purified HA and NA (sub-unit) vaccine, as the immunogenic composition used for the first vaccination. Alternatively the boosting composition may contain another type of influenza antigen than that used for the first vaccination. Preferably a split virus is used. The boosting composition may be adjuvanted or un-adjuvanted. The un-adjuvanted boosting composition may be Fluarix™/α-Rix®/Influsplit® given intramuscularly. The formulation contains three inactivated split virion antigens prepared from the WHO recommended strains of the appropriate influenza season.

The boosting composition may be adjuvanted or un-adjuvanted. In a specific embodiment, the boosting composition comprises a saponin adjuvant which is as defined herein.

In a specific embodiment, the immunogenic composition for revaccination (also called herein below the 'boosting composition') contains an influenza virus or antigenic preparation thereof which shares common CD4 T-cell epitopes with the influenza virus or antigenic preparation thereof used for the first vaccination. A common CD4 T cell epitope is intended to mean peptides/sequences/epitopes from different antigens which can be recognised by the same CD4 cell (see examples of described epitopes in: Gelder C et al. 1998, Int Immunol. 10(2):211-22; Gelder C M et al. 1996 J Virol. 70(7):4787-90; Gelder C M et al. 1995 J Virol. 1995 69(12):7497-506).

In an embodiment according to the invention, the boosting composition is a monovalent influenza composition comprising an influenza strain which is associated with a pandemic outbreak or has the potential to be associated with a pandemic outbreak. In particular said strain in the boosting composition is a circulating pandemic strain. Suitable strains are, but not limited to: H5N1, H9N2, H7N7, and H2N2. Said strain may be the same as that, or one of those, present in the composition used for the first vaccination. In an alternative embodiment said strain may be a variant strain, i.e. a drift strain, of the strain present in the composition used for the first vaccination.

In another specific embodiment, the boosting composition is a multivalent influenza vaccine. In particular, when the boosting composition is a multivalent vaccine such as a bivalent, trivalent or quadrivalent vaccine, at least one strain is associated with a pandemic outbreak or has the potential to be associated with a pandemic outbreak. In a specific embodiment, two or more strains in the boosting composition are pandemic strains. In another specific embodiment, the at least one pandemic strain in the boosting composition is of the same type as that, or one of those, present in the composition used for the first vaccination. In an alternative embodiment the at least one strain may be a variant strain, i.e. a drift strain, of the at least one pandemic strain present in the composition used for the first vaccination. In particular the at least one strain in the boosting composition is a circulating pandemic strain. The boosting composition may be adjuvanted or not.

Typically a boosting composition, where used, is given at the next influenza season, e.g. approximately one year after the first immunogenic composition. The boosting composition may also be given every subsequent year (third, fourth, fifth vaccination and so forth). The boosting composition may be the same as the composition used for the first vaccination. Suitably, the boosting composition contains an influenza virus or antigenic preparation thereof which is a variant strain of the influenza virus used for the first vaccination. In particular, the influenza viral strains or antigenic preparation thereof are selected according to the reference material distributed by the World Health Organisation such that they are adapted to the influenza strain which is circulating on the year of the revaccination.

The influenza antigen or antigenic composition used in revaccination preferably comprises an adjuvant, suitably as described above. The adjuvant may be a saponin presented in the form of a liposome, as herein above described, which is preferred, optionally containing an additional adjuvant such as 3D-MPL.

In one aspect revaccination induces any, preferably two or all, of the following: (i) an improved CD4 response against the influenza virus or antigenic preparation thereof, or (ii) an improved B cell memory response or (iii) an improved humoral response, compared to the equivalent response induced after a first vaccination with the un-adjuvanted influenza virus or antigenic preparation thereof. Preferably the immunological response(s) induced after revaccination with the adjuvanted influenza virus or antigenic preparation thereof as herein defined, is (are) higher than the corresponding response induced after the revaccination with the un-adjuvanted composition. Preferably the immunological responses induced after revaccination with an un-adjuvanted, preferably split, influenza virus are higher in the population first vaccinated with the adjuvanted, preferably split, influenza composition than the corresponding response in the population first vaccinated with the un-adjuvanted, preferably split, influenza composition.

In a specific embodiment, the revaccination of the subjects with a boosting composition comprising an influenza virus and a saponin adjuvant in the form of a liposome, as defined herein above, shows higher antibody titers than the corresponding values in the group of people first vaccinated with the un-adjuvanted composition and boosted with the un-adjuvanted composition. The effect of the adjuvant in enhancing the antibody response to revaccination is especially of importance in the elderly population which is known to have a low response to vaccination or infection by influenza virus. The adjuvanted composition-associated benefit was also marked in terms of improving the CD4 T-cell response following revaccination.

Specifically, the adjuvanted composition of the invention is capable of inducing a better cross-responsiveness against drifted strain (the influenza strain from the next influenza season) compared to the protection conferred by the control vaccine. Said cross-responsiveness has shown a higher persistence compared to that obtained with the un-adjuvanted formulation. The effect of the adjuvant in enhancing the cross-responsiveness against drifted strain is of important in a pandemic situation.

In a further embodiment the invention relates to a vaccination regime in which the first vaccination is made with an influenza composition, preferably a split influenza composition, containing at least one influenza strain that could potentially cause a pandemic outbreak and the revaccination is made with a circulating strain, either a pandemic strain or a classical strain.

CD4 Epitope in HA

This antigenic drift mainly resides in epitope regions of the viral surface proteins haemagglutinin (HA) and neuraminidase (NA). It is known that any difference in CD4 and B cell epitopes between different influenza strains, being used by the virus to evade the adaptive response of the host immune system, will play a major role in influenza vaccination and is.

CD4 T-cell epitopes shared by different Influenza strains have been identified in human (see for example: Gelder C et al. 1998, Int Immunol. 10(2):211-22; Gelder C M et al. 1996 J Virol. 70(7):4787-90; and Gelder C M et al. 1995 J Virol. 1995 69(12):7497-506).

In a specific embodiment, the revaccination is made by using a boosting composition which contains an influenza virus or antigenic preparation thereof which shares common CD4 T-cell epitopes with the influenza virus antigen or antigenic preparation thereof used for the first vaccination. The invention thus relates to the use of the immunogenic composition comprising a pandemic influenza virus or antigenic preparation thereof and a saponin in the form of a liposome, in particular QS21 in its detoxified form with cholesterol optionally with 3D-MPL, in the manufacture of a first vaccination-component of a multi-dose vaccine, the multi-dose vaccine further comprising, as a boosting dose, an influenza virus or antigenic preparation thereof which shares common CD4 T-cell epitopes with the pandemic influenza virus antigen or virus antigenic preparation thereof of the dose given at the first vaccination.

Vaccination Means

The immunogenic compositions of the invention may be administered by any suitable delivery route, such as intradermal, mucosal e.g. intranasal, oral, intramuscular or subcutaneous. Other delivery routes are well known in the art.

The intramuscular delivery route is preferred for the adjuvanted immunogenic composition.

Intradermal delivery is another suitable route. Any suitable device may be used for intradermal delivery, for example short needle devices such as those described in U.S. Pat. Nos. 4,886,499, 5,190,521, 5,328,483, 5,527,288, 4,270,537, 5,015,235, 5,141,496, 5,417,662. Intradermal vaccines may also be administered by devices which limit the effective penetration length of a needle into the skin, such as those described in WO99/34850 and EP1092444, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556 4,790,824, 4,941,880, 4,940,460, WO 97/37705 and WO 97/13537. Also suitable are ballistic powder/particle delivery devices which use compressed gas to accelerate vaccine in powder form through the outer layers of the skin to the dermis. Additionally, conventional syringes may be used in the classical mantoux method of intradermal administration.

Another suitable administration route is the subcutaneous route. Any suitable device may be used for subcutaneous delivery, for example classical needle. Preferably, a needle-free jet injector service is used, such as that published in WO 01/05453, WO 01/05452, WO 01/05451, WO 01/32243, WO 01/41840, WO 01/41839, WO 01/47585, WO 01/56637, WO 01/58512, WO 01/64269, WO 01/78810, WO 01/91835, WO 01/97884, WO 02/09796, WO 02/34317. More preferably said device is pre-filled with the liquid vaccine formulation.

Alternatively the vaccine is administered intranasally. Typically, the vaccine is administered locally to the nasopharyngeal area, preferably without being inhaled into the lungs. It is desirable to use an intranasal delivery device which delivers the vaccine formulation to the nasopharyngeal area, without or substantially without it entering the lungs.

Preferred devices for intranasal administration of the vaccines according to the invention are spray devices. Suitable commercially available nasal spray devices include Accuspray™ (Becton Dickinson). Nebulisers produce a very fine spray which can be easily inhaled into the lungs and therefore does not efficiently reach the nasal mucosa. Nebulisers are therefore not preferred.

Preferred spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO 91/13281 and EP 311 863 B and EP 516 636, incorporated herein by reference. Such devices are commercially available from Pfeiffer GmbH and are also described in Bommer, R. Pharmaceutical Technology Europe, September 1999.

Preferred intranasal devices produce droplets (measured using water as the liquid) in the range 1 to 200 μm, preferably 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Bi-dose delivery is a further preferred feature of an intranasal delivery system for use with the vaccines according to the invention. Bi-dose devices contain two sub-doses of a single vaccine dose, one sub-dose for administration to each nostril. Generally, the two sub-doses are present in a single chamber and the construction of the device allows the efficient delivery of a single sub-dose at a time. Alternatively, a monodose device may be used for administering the vaccines according to the invention.

Alternatively, the epidermal or transdermal vaccination route is also contemplated in the present invention.

In a specific aspect of the present invention, the adjuvanted immunogenic composition for the first administration may be given intramuscularly, and the boosting composition, either adjuvanted or not, may be administered through a different route, for example intradermal, subcutaneous or intranasal. In another specific embodiment, an immunogenic composition comprising specifically an influenza virus antigen or antigenic preparation thereof for the first administration may contain a standard HA content of 15 μg per influenza strain, and the boosting influenza composition may contain a low dose of HA, i.e. below 15 μg, and depending on the administration route, may be given in a smaller volume.

Populations to Vaccinate

The target population to vaccinate may be immuno-compromised human. Immuno-compromised humans generally are less well able to respond to an antigen, in particular to an influenza antigen, in comparison to healthy adults.

Preferably the target population is a population which is unprimed against influenza, either being naïve (such as visa à vis a pandemic strain), or having failed to respond previously to influenza infection or vaccination. Preferably the target population is elderly persons suitably aged 65 years and over, younger high-risk adults (i.e. between 18 and 64 years of age) such as people working in health institutions, or those young adults with a risk factor such as cardiovascular and pulmonary disease, or diabetes. Another target population is all children 6 months of age and over, especially children 6-23 months of age who experience a relatively high influenza-related hospitalization rate. Preferably the target population is elderly above 65 years of age.

Vaccination Regimes, Dosing and Additional Efficacy Criteria

Suitably the immunogenic compositions according to the present invention are a standard 0.5 ml injectable dose in most cases, and, when an influenza composition, contains 15 μg of haemagglutinin antigen component from the or each influenza strain, as measured by single radial immunodiffusion (SRD) (J. M. Wood et al.: J. Biol. Stand. 5 (1977) 237-247; J. M. Wood et al., J. Biol. Stand. 9 (1981) 317-330). Suitably the vaccine dose volume will be between 0.5 ml and 1 ml, in particular a standard 0.5 ml, or 0.7 ml vaccine dose volume. For influenza vaccines, slight adaptation of the dose volume will be made routinely depending on the HA concentration in the original bulk sample.

Suitably said immunogenic composition contains a low dose of HA antigen—e.g any of 1, 2, 3, 4, 5, 6, 7, 8, 9, 10, 11, 12, 13 or 14 μg of HA per influenza strain.

Advantageously, a vaccine dose according to the invention, in particular a low dose vaccine, may be provided in a smaller volume than the conventional injected split flu vaccines, which are generally around 0.5, 0.7 or 1 ml per dose. The low volume doses according to the invention are preferably below 500 more preferably below 300 μl and most preferably not more than about 200 μl or less per dose.

Thus, a preferred low volume vaccine dose according to one aspect of the invention is a dose with a low antigen dose in a low volume, e.g. about 15 μg or about 7.5 μg HA or about 3.0 μg HA (per strain) in a volume of about 200 μl.

The influenza medicament of the invention preferably meets certain international criteria for vaccines.

Standards are applied internationally to measure the efficacy of influenza vaccines. The European Union official criteria for an effective vaccine against influenza are set out in the Table 1 below. Theoretically, to meet the European Union requirements, an influenza vaccine has to meet only one of the criteria in the table, for all strains of influenza included in the vaccine. The compositions of the present invention suitably meet at least one such criteria.

However in practice, at least two or all three of the criteria will need to be met for all strains, particularly for a new vaccine such as a new vaccine for delivery via a different route. Under some circumstances two criteria may be sufficient. For example, it may be acceptable for two of the three criteria to be met by all strains while the third criterion is met by some but not all strains (e.g. two out of three strains). The requirements are different for adult populations (18-60 years) and elderly populations (>60 years).

TABLE 1

|  | 18-60 years | >60 years |
| --- | --- | --- |
| Seroconversion rate* | >40% | >30% |
| Conversion factor** | >2.5 | >2.0 |
| Protection rate*** | >70% | >60% |

*Seroconversion rate is defined as the percentage of vaccinees who have at least a 4-fold increase in serum haemagglutinin inhibition (HI) titres after vaccination, for each vaccine strain.
**Conversion factor is defined as the fold increase in serum HI geometric mean titres (GMTs) after vaccination, for each vaccine strain.
***Protection rate is defined as the percentage of vaccinees with a serum HI titre equal to or greater than 1:40 after vaccination (for each vaccine strain) and is normally accepted as indicating protection.

In a further aspect the invention provides a method of designing a vaccine for diseases known to be cured or treated through a CD4+ T cell activation, comprising
  1) selecting an antigen containing CD4+ epitopes, and
  2) combining said antigen with saponin adjuvant in the form of a liposome as defined herein above, wherein said vaccine upon administration in said mammal is capable of inducing an enhanced CD4 T cell response in said mammal.

The teaching of all references in the present application, including patent applications and granted patents, are herein fully incorporated by reference.

For the avoidance of doubt the terms 'comprising', 'comprise' and 'comprises' herein is intended by the inventors to be optionally substitutable with the terms 'consisting of', 'consist of', and 'consists of', respectively, in every instance.

The invention will be further described by reference to the following, non-limiting, examples:

Example I describes immunological read-out methods used in mice, ferret and human studies.

Example II describes preparation of the MPL/QS21 liposomal adjuvant

Example III describes a pre-clinical evaluation of adjuvanted and unadjuvanted influenza vaccines in ferrets.

Example IV shows a pre-clinical evaluation of adjuvanted and un-adjuvanted influenza vaccines in C57Bl/6 naïve and primed mice.

Example V describes a comparison of adjuvanted influenza vaccine with 3D-MPL at two different concentrations in mice.

Example VI describes a comparison of adjuvanted influenza vaccine with 3D-MPL at two different concentrations in elderly humans.

Example VII describes the pre-clinical evaluation of adjuvanted HPV vaccines in mice.

Example VIII describes a pre-clinical evaluation of adjuvanted and non-adjuvanted cytomegaolovirus immunogenic compositions.

Example IX describes the pre-clinical evaluation of an adjuvanted RTS,S vaccine composition with 3D-MPL at two different concentrations.

Example X describes the clinical evaluation of an adjuvanted RTS,S vaccine with 3D-MPL at two different concentrations.

EXAMPLE I

Immunological Read-out Methods

I.1. Mice Methods
I.1.1. Hemagglutination Inhibition Test
Test Procedure

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Heat inactivated sera were previously treated by Kaolin and chicken RBC to remove non-specific inhibitors. After pretreatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:20, an undetectable level was scored as a titer equal to 10.

Statistical Analysis

Statistical analysis were performed on post vaccination HI titers using UNISTAT. The protocol applied for analysis of variance can be briefly described as follow:
  Log transformation of data
  Shapiro-Wilk test on each population (group) in order to verify the normality of groups distribution
  Cochran test in order to verify the homogenicity of variance between the different populations (groups)
  Two-way Analysis of variance performed on groups
  Tukey HSD test for multiple comparisons I.1.2. Intracellular Cytokine Staining This technique allows a quantification of antigen specific T lymphocytes on the basis of cytokine production: effector T cells and/or effector-memory T cells produce IFN-γ and/or central memory T cells produce IL-2. PBMCs are harvested at day 7 post-immunization.

Lymphoid cells are re-stimulated in vitro in the presence of secretion inhibitor (Brefeldine):

These cells are then processed by conventional immuno-fluorescent procedure using fluorescent antibodies (CD4, CD8, IFN-γ and IL-2). Results are expressed as a frequency of cytokine positive cell within CD4/CD8 T cells. Intracellular staining of cytokines of T cells was performed on PBMC 7 days after the second immunization. Blood was collected from mice and pooled in heparinated medium RPMI+Add. For blood, RPMI+Add-diluted PBL suspensions were layered onto a Lympholyte-Mammal gradient according to the recommended protocol (centrifuge 20 min at 2500 rpm and R.T.). The mononuclear cells at the interface were removed, washed 2× in RPMI+Add and PBMCs suspensions were adjusted to $2\times10^6$ cells/ml in RPMI 5% fetal calf serum.

In vitro antigen stimulation of PBMCs was carried out at a final concentration of $1\times10^6$ cells/ml (tube FACS) with Flu trivalent split on µbeads (5 µg HA/strain) or Whole FI (1 µgHA/strain) and then incubated 2 hrs at 37° C. with the addition of anti-CD28 and anti-CD49d (1 µg/ml for both).

The addition of both antibodies, increased proliferation and cytokine production by activated T and NK cells and can provide a costimulatory signal for CTL induction.

In addition, PBMCs were also stimulated overnight with Flu trivalent split (30 µg HA/strain)- or Whole FI (5 µgHA/strain)-pulsed BMDCs ($1\times10^5$ cells/ml), which were prepared by pulsing BMDCs with Flu split (60 µg/HA strain) or Whole Flu trivalent FI (10 µgHA/strain) for 6 hrs at 37° C. Following the antigen restimulation step, PBMC are incubated O.N. at 37° C. in presence of Brefeldin (1 µg/ml) at 37° C. to inhibit cytokine secretion.

IFN-γ/IL-2/CD4/CD8 staining was performed as follows: Cell suspensions were washed, resuspended in 50 µl of PBS 1% FCS containing 2% Fc blocking reagent (1/50; 2.4G2). After 10 min incubation at 4° C., 50 µl of a mixture of anti-CD4-PE (2/50) and anti-CD8 perCp (3/50) was added and incubated 30 min at 4° C. After a washing in PBS 1% FCS, cells were permeabilized by resuspending in 200 µl of Cytofix-Cytoperm (Kit BD) and incubated 20 min at 4° C. Cells were then washed with Perm Wash (Kit BD) and resuspended with 50 µl of a mix of anti-IFN-γ APC (1/50)+ anti-IL-2 FITC (1/50) diluted in Perm Wash. After an incubation min 2 h max overnight at 4° C., cells were washed with Perm Wash and resuspended in PBS 1% FCS+1% paraformaldéhyde. Sample analysis was performed by FACS. Live cells were gated (FSC/SSC) and acquisition was performed on ~50,000 events (lymphocytes) or 35,000 events on CD4+ T cells. The percentages of IFN-γ+ or IL2+ were calculated on CD4+ and CD8+ gated populations.

I.2. Ferrets Methods

I.2.1. Hemagglutination Inhibition Test (HI)

Test Procedure.

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pretreatment, two-fold dilutions of sera were incubated with 4 hemagglutination units of each influenza strain. Chicken red blood cells were then added and the inhibition of agglutination was scored using tears for reading. The titers were expressed as the reciprocal of the highest dilution of serum that completely inhibited hemagglutination. As the first dilution of sera was 1:10, an undetectable level was scored as a titer equal to 5.

Statistical Analysis.

Statistical analysis were performed on HI titers (Day 41, before challenge) using UNISTAT. The protocol applied for analysis of variance can be briefly described as followed:

Log transformation of data.

Shapiro-wilk test on each population (group) in order to verify the normality of groups distribution.

Cochran test in order to verify the homogenicity of variance between the different populations (groups).

Test for interaction of one-way ANOVA.

Tuckey-HSD Test for multiple comparisons.

I.2.2. Nasal Washes

The nasal washes were performed by administration of 5 ml of PBS in both nostrils in awake animals. The inoculum was collected in a Petri dish and placed into sample containers on dry ice.

Viral Titration in Nasal Washes

All nasal samples were first sterile filtered through Spin X filters (Costar) to remove any bacterial contamination. 50 µl of serial ten-fold dilutions of nasal washes were transferred to microtiter plates containing 50 µl of medium (10 wells/dilution). 100 µl of MDCK cells ($2.4\times10^5$ cells/ml) were then added to each well and incubated at 35° C. for 5-7 days. After 6-7 days of incubation, the culture medium is gently removed and 100 µl of a 1/20 WST-1 containing medium is added and incubated for another 18 hrs.

The intensity of the yellow formazan dye produced upon reduction of WST-1 by viable cells is proportional to the number of viable cells present in the well at the end of the viral titration assay and is quantified by measuring the absorbance of each well at the appropriate wavelength (450 nanometers). The cut-off is defined as the OD average of uninfected control cells—0.3 OD (0.3 OD correspond to +/−3 StDev of OD of uninfected control cells). A positive score is defined when OD is <cut-off and in contrast a negative score is defined when OD is >cut-off. Viral shedding titers were determined by "Reed and Muench" and expressed as Log TCID50/ml.

I.3. Assays for Assessing the Immune Response in Humans

I.3.1. Hemagglutination Inhibition Assay

The immune response was determined by measuring HI antibodies using the method described by the WHO Collaborating Centre for influenza, Centres for Disease Control, Atlanta, USA (1991).

Antibody titre measurements were conducted on thawed frozen serum samples with a standardised and comprehensively validated micromethod using 4 hemagglutination-inhibiting units (4 HIU) of the appropriate antigens and a 0.5% fowl erythrocyte suspension. Non-specific serum inhibitors were removed by heat treatment and receptor-destroying enzyme.

The sera obtained were evaluated for HI antibody levels. Starting with an initial dilution of 1:10, a dilution series (by a factor of 2) was prepared up to an end dilution of 1:20480. The titration end-point was taken as the highest dilution step that showed complete inhibition (100%) of hemagglutination. All assays were performed in duplicate.

I.3.2. Neuraminidase Inhibition Assay

The assay was performed in fetuin-coated microtitre plates. A 2-fold dilution series of the antiserum was prepared and mixed with a standardised amount of influenza A H3N2, H1N1 or influenza B virus. The test was based on the biological activity of the neuraminidase which enzymatically releases neuraminic acid from fetuin. After cleavage of the terminal neuraminic acid β-D-galactose-N-acetyl-galactosamin was unmasked. Horseradish peroxidase (HRP)-labelled peanut agglutinin from *Arachis hypogaea*, which binds specifically to the galactose structures, was added to the wells. The amount of bound agglutinin can be detected and quantified in a substrate reaction with tetra-methylbenzidine (TMB). The highest antibody dilution that still inhibits the viral neuraminidase activity by at least 50% was indicated is the NI titre.

I.3.3. Neutralising Antibody Assay

Neutralising antibody measurements were conducted on thawed frozen serum samples. Virus neutralisation by antibodies contained in the serum was determined in a microneutralization assay. The sera were used without further treatment in the assay. Each serum was tested in triplicate. A standardised amount of virus was mixed with serial dilutions of serum and incubated to allow binding of the antibodies to the virus. A cell suspension containing a defined amount of MDCK cells was then added to the mixture of virus and antiserum and incubated at 33° C. After the incubation period, virus replication was visualised by hemagglutination of chicken red blood cells. The 50% neutralisation titre of a serum was calculated by the method of Reed and Muench, *Am J Epidemiol* 1938; 27: 493.

I.3.4. Cell-mediated Immunity was Evaluated by Cytokine Flow Cytometry (CFC)

Peripheral blood antigen-specific CD4 and CD8 T cells can be restimulated in vitro to produce IL-2, CD40L, TNF-alpha and IFN if incubated with their corresponding antigen. Consequently, antigen-specific CD4 and CD8 T cells can be enumerated by flow cytometry following conventional immunofluorescence labelling of cellular phenotype as well as intracellular cytokines production. In the present study, Influenza vaccine antigen as well as peptides derived from specific influenza protein were used as antigen to restimulate Influenza-specific T cells. Results were expressed as a frequency of cytokine(s)-positive CD4 or CD8 T cell within the CD4 or CD8 T cell sub-population.

I.3.5. Statistical Methods

I.3.5.1. Primary Endpoints

Percentage, intensity and relationship to vaccination of solicited local and general signs and symptoms during a 7 day follow-up period (i.e. day of vaccination and 6 subsequent days) after vaccination and overall.

Percentage, intensity and relationship to vaccination of unsolicited local and general signs and symptoms during a 21 day follow-up period (i.e. day of vaccination and 20 subsequent days) after vaccination and overall.

Occurrence of serious adverse events during the entire study.

I.3.5.2. Secondary Endpoints

For the Humoral Immune Response:

Observed Variables:
  At days 0 and 21: serum hemagglutination-inhibition (HI) and NI antibody titres, tested separately against each of the three influenza virus strains represented in the vaccine (anti-H1N1, anti-H3N2 & anti-B-antibodies).
  At days 0 and 21: neutralising antibody titres, tested separately against each of the three influenza virus strains represented in the vaccine Derived Variables (with 95% Confidence Intervals):
  Geometric mean titres (GMTs) of serum HI antibodies with 95% confidence intervals (95% CI) pre and post-vaccination
  Seroconversion rates* with 95% CI at day 21
  Conversion factors** with 95% CI at day 21
  Seroprotection rates*** with 95% CI at day 21
  Serum NI antibody GMTs' (with 95% confidence intervals) at all timepoints.
  *Seroconversion rate defined as the percentage of vaccinees who have at least a 4-fold increase in serum HI titres on day 21 compared to day 0, for each vaccine strain.
  **Conversion factor defined as the fold increase in serum HI GMTs on day 21 compared to day 0, for each vaccine strain.
  ***Protection rate defined as the percentage of vaccinees with a serum HI titre=40 after vaccination (for each vaccine strain) that usually is accepted as indicating protection.

For the Cell Mediated Immune (CMI) Response

Observed Variable

At days 0 and 21: frequency of cytokine-positive CD4/CD8 cells per $10^6$ in different tests. Each test quantifies the response of CD4/CD8 T cell to:
  Peptide Influenza (pf) antigen (the precise nature and origin of these antigens needs to be given/explained
  Split Influenza (sf) antigen
  Whole Influenza (wf) antigen.

Derived Variables:
  cells producing at least two different cytokines (CD40L, IL-2, IFNγ, TNFα)
  cells producing at least CD40L and another cytokine (IL-2, TNFα, IFNγ)
  cells producing at least IL-2 and another cytokine (CD40L, TNFα, IFNγ)
  cells producing at least IFNγ and another cytokine (IL-2, TNFα, CD40L)
  cells producing at least TNFα and another cytokine (IL-2, CD40L, IFNγ)

I.3.5.3. Analysis of Immunogenicity

The immunogenicity analysis was based on the total vaccinated cohort. For each treatment group, the following parameters (with 95% confidence intervals) were calculated:
  Geometric mean titres (GMTs) of HI and NI antibody titres at days 0 and 21
  Geometric mean titres (GMTs) of neutralising antibody titres at days 0 and 21.
  Conversion factors at day 21.
  Seroconversion rates (SC) at day 21 defined as the percentage of vaccinees that have at least a 4-fold increase in serum HI titres on day 21 compared to day 0.
  Protection rates at day 21 defined as the percentage of vaccinees with a serum HI titre=1:40.
  The frequency of CD4/CD8 T-lymphocytes secreting in response was summarised (descriptive statistics) for each vaccination group, at each timepoint (Day 0, Day 21) and for each antigen (Peptide influenza (pf), split influenza (sf) and whole influenza (wf).
  Descriptive statistics in individual difference between timepoint (Post-Pre) responses fore each vaccination group and each antigen (pf, sf, and wf) at each 5 different tests.
  A non-parametric test (Kruskall-Wallis test) was used to compare the location differences between the 3 groups and the statistical p-value was calculated for each antigen at each 5 different tests. All significance tests were two-tailed. P-values less than or equal to 0.05 were considered as statistically significant.

EXAMPLE II

Preparation of the MPL/QS21 Liposomal Adjuvant

II.3 Preparation of MPL Liquid Suspension

The MPL (as used throughout the document it is an abbreviation for 3D-MPL, i.e. 3-O-deacylated monophosphoryl lipid A) liquid bulk is prepared from 3D-MPL lyophilized powder. MPL liquid bulk is a stable concentrated (around 1 mg/ml) aqueous dispersion of the raw material, which is ready-to-use for vaccine or adjuvant formulation. A schematic representation of the preparation process is given in FIG. 1.

For a maximum batch size of 12 g, MPL liquid bulk preparation is carried over in sterile glass containers. The dispersion of MPL consists of the following steps:
  suspend the MPL powder in water for injection
  desaggregate any big aggregates by heating (thermal treatment)

reduce the particle size between 100 nm and 200 nm by microfluidization prefilter the preparation on a Sartoclean Pre-filter unit, 0.8/0.65 μm sterile filter the preparation at room temperature (Sartobran P unit, 0.22 μm)

MPL powder is lyophilized by microfluidisation resulting in a stable colloidal aqueous dispersion (MPL particles of a size susceptible to sterile filtration). The MPL lyophilized powder is dispersed in water for injection in order to obtain a coarse 10 mg/ml suspension. The suspension then undergoes a thermal treatment under stirring. After cooling to room temperature, the microfluidization process is started in order to decrease the particle size. Microfluidization is conducted using Microfluidics apparatus M110EH, by continuously circulating the dispersion through a microfluidization interaction chamber, at a defined pressure for a minimum amount of passages (number of cycles: $n_{min}$). The microfluidization duration, representing the number of cycles, is calculated on basis of the measured flow rate and the dispersion volume. On a given equipment at a given pressure, the resulting flow rate may vary from one interaction chamber to another, and throughout the lifecycle of a particular interaction chamber. In the present example the interaction chamber used is of the type F20Y Microfluidics. As the microfluidization efficiency is linked to the couple pressure—flow rate, the processing time may vary from one batch to another. The time required for 1 cycle is calculated on basis of the flow rate. The flow rate to be considered is the flow rate measured with water for injection just before introduction of MPL into the apparatus. One cycle is defined as the time (in minutes) needed for the total volume of MPL to pass once through the apparatus. The time needed to obtain n cycles is calculated as follows:

n×quantity of MPL to treat (ml)/flow rate (ml/min)

The number of cycles is thus adapted accordingly. Minimum amount of cycles to perform ($n_{min}$) are described for the preferred equipment and interaction chambers used. The total amount of cycles to run is determined by the result of a particle size measurement performed after $n_{min}$ cycles. A particle size limit ($d_{lim}$) is defined, based on historical data. The measurement is realized by photon correlation spectroscopy (PCS) technique, and $d_{lim}$ is expressed as an unimodal result ($Z_{average}$). Under this limit, the microfluidization can be stopped after $n_{min}$ cycles. Above this limit, microfluidization is continued until satisfactory size reduction is obtained, for maximum another 50 cycles.

If the filtration does not take place immediately after microfluidization, the dispersed MPL is stored at +2 to +8° C. awaiting transfer to the filtration area.

After microfluidization, the dispersion is diluted with water for injection, and sterile filtered through a 0.22 μm filter under laminal flow. The final MPL concentration is 1 mg/ml (0.80-1.20 mg/ml).

II.2 Preparation of MPL/QS21 Liposomal Adjuvant

This adjuvant, named AS01, comprises 3D-MPL and QS21 in a quenched form with cholesterol, and was made as described in WO 96/33739, incorporated herein by reference. In particular the AS01 adjuvant was prepared essentially as Example 1.1 of WO 96/33739. The AS01B adjuvant comprises: liposomes, which in turn comprise dioleoyl phosphatidylcholine (DOPC), cholesterol and 3D MPL [in an amount of 1000 μg DOPC, 250 μg cholesterol and 50 μg 3D-MPL, each value given approximately per vaccine dose], QS21 [50 μg/dose], phosphate NaCl buffer and water to a volume of 0.5 ml.

The AS01E adjuvant comprises the same ingredients than AS01B but at a lower concentration in an amount of 500 μg DOPC, 125 μg cholesterol, 25 μg 3D-MPL and 25 μg QS21, phosphate NaCl buffer and water to a volume of 0.5 ml.

In the process of production of liposomes containing MPL the DOPC (Dioleyl phosphatidylcholine), cholesterol and MPL are dissolved in ethanol. A lipid film is formed by solvent evaporation under vacuum. Phosphate Buffer Saline (9 mM $Na_2HPO_4$, 41 mM $KH_2PO_4$, 100 mM NaCl) at pH 6.1 is added and the mixture is submitted to prehomogenization followed by high pressure homogenisation at 15,000 psi (around 15 to 20 cycles). This leads to the production of liposomes which are sterile filtered through a 0.22 μm membrane in an aseptic (class 100) area. The sterile product is then distributed in sterile glass containers and stored in a cold room (+2 to +8° C.).

In this way the liposomes produced contain MPL in the membrane (the "MPL in" embodiment of WO 96/33739).

QS21 is added in aqueous solution to the desired concentration.

EXAMPLE III

Pre-clinical Evaluation of Adjuvanted and Unadjuvanted Influenza Vaccines in Ferrets III.1. Rationale and Objectives Influenza infection in the ferret model closely mimics human influenza, with regards both to the sensitivity to infection and the clinical response.

The ferret is extremely sensitive to infection with both influenza A and B viruses without prior adaptation of viral strains. Therefore, it provides an excellent model system for studies of protection conferred by administered influenza vaccines.

This study investigated the efficacy of various Trivalent Split vaccines, adjuvanted or not, to reduce disease symptoms (body temperature) and viral shedding in nasal secretions of ferrets challenged with homologous strains.

The objective of this experiment was to demonstrate the efficacy of an adjuvanted influenza vaccine compared to the plain (un-adjuvanted) vaccine.

The end-points were:

1) Primary end-point: reduction of viral shedding in nasal washes after homologous challenge:

2) Secondary end-points: Analysis of the humoral response by HI titers.

III.2. Experimental Design

III.2.1. Treatment/Group (Table 1)

Female ferrets (*Mustela putorius* furo) aged 14-20 weeks were obtained from MISAY Consultancy (Hampshire, UK). Ferrets were primed on day 0 with heterosubtypic strain H1N1 A/Stockholm/24/90 (4 Log $TCID_{50}$/ml). On day 21, ferrets were injected intramuscularly with a full human dose (500 μg vaccine dose, 15 μg HA/strain) of a combination of H1N1 A/New Caledonia/20/99, H3N2 A/Panama/2007/99 and B/Shangdong/7/97. Ferrets were then challenged on day 42 by intranasal route with an heterosubtypic strain H3N2 A/Wyoming/3/2003 (4.5 Log $TCID_{50}$/ml).

TABLE 1

| Group | Antigen(s) + dosage | Formulation + dosage | Comments (schedule/ route/ challenge) | In/ Po | Other treatments |
|---|---|---|---|---|---|
| 1 | Trivalent Plain | Full HD: 15 μg HA/strain | IM; Day 21 | In | Priming H1N1 (A/Stockholm/24/ 90) Day 0 |

TABLE 1-continued

| Group | Antigen(s) + dosage | Formulation + dosage | Comments (schedule/ route/ challenge) | In/ Po | Other treatments |
|---|---|---|---|---|---|
| 2 | Trivalent/ MPL-QS21 in liposomes | Full HD: 15 µg HA/strain | IM; Day 21 | In | Priming H1N1 (A/Stockolm/24/ 90) Day 0 |

6 ferrets/group.
In/Po = Individual/pool

III.2.2. Preparation of the Vaccine Formulations (Table 2)
Formulation 1: Trivalent Split Plain (Un-adjuvanted) Formulation:

PBS 10 fold concentrated (pH 7.4 when one fold concentrated) as well as a mixture containing Tween 80, Triton X-100 and VES (quantities taking into account the detergents present in the strains) are added to water for injection. After 5 min stirring, 15 µg of each strain H1N1, H3N2 and 17.5 µg of B strain are added with 10 min stirring between each addition. The formulation is stirred for minimum 15 minutes and stored at 4° C. if not administered directly.

Formulation 2: Trivalent Split Influenza Adjuvanted with MPL/QS21 in Liposomes:

PBS 10 fold concentrated (pH 7.4 when one fold concentrated) as well as a mixture containing Tween 80, Triton X-100 and VES (quantities taking into account the detergents present in the strains) are added to water for injection. After 5 min stirring, 15 µg of each strain H1N1, H3N2 and 17.5 µg of B strain are added with 10 min stirring between each addition. The formulation is stirred for 15 minutes. A premix of so called "DQS21-MPLin is added to the formulation which is then stirred for minimum 15 minutes. The DQS21-MPLin premix is a mixture of liposomes (made of DOPC 40 mg/ml, cholesterol 10 mg/ml, MPL 2 mg/ml) and the immunostimulant QS21. This premix is incubated for a minimum of 15 minutes prior to addition to the trivalent split mixture. The concentration of MPL and QS21 in the final formulation is 50 µg per 500 µl. The formulation is stored at 4° C. if not administered directly.

Remark: In each formulation, PBS 10 fold concentrated is added to reach isotonicity and is 1 fold concentrated in the final volume. H2O volume is calculated to reach the targeted volume.

TABLE 2

Final composition of formulations 1 and 2 (Formulations prepared with split strains (for 500 µl))

| Formulation | Antigen | Tween 80 | Triton X-100 | VES | DOPC | Cholesterol | MPL | QS21 |
|---|---|---|---|---|---|---|---|---|
| 1 | H1N1: 15 µg H3N2: 15 µg B: 17.5 µg | 375 µg | 55 µg | 50 µg | — | — | — | — |
| 2 | H1N1: 15 µg H3N2: 15 µg B: 17.5 µg | 375 µg | 55 µg | 50 µg | 1 mg | 250 µg | 50 µg | 50 µg |

III.2.3. Read-outs (Table 3)

TABLE 3

| Readout | Timepoint | Sample-type | Analysis method |
|---|---|---|---|
| Viral shedding | D + 1 to D + 7 Post challenge | Nasal washes | Titration |

TABLE 3-continued

| Readout | Timepoint | Sample-type | Analysis method |
|---|---|---|---|
| Anti-HI antibodies (HI titers) | Pre, Post priming, Post immunization, Post challenge | Sera | Hemagglutination inhibition test |

III.3. Results

Figure 1:
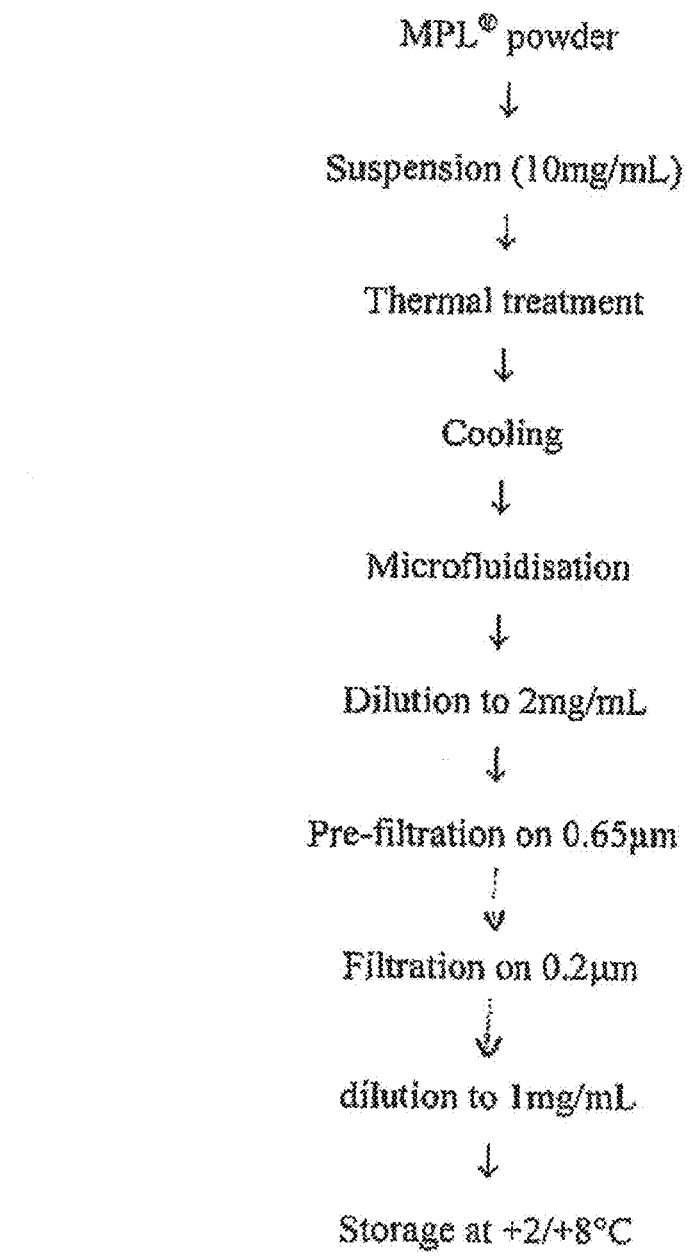
FIG. 1—diagrammatic representation of MPL preparation.

A schematic representation of the results is given in FIGS. 1 and 2.

III.3.1. Humoral Immunity (FIG. 1).

Hemagglutination inhibition activity against the H3N2 vaccine strains (vaccine strain A/Panama/2007/99 and challenge strain A/Wyoming/3/2003) was detected in sera from 6 animals per group at Day 17 after intranasal heterologous priming and at Day 21 Post-immunization and Day 13 Post-challenge.

Anti-Hemagglutinin antibody titers to the three influenza virus strains were determined using the hemagglutination inhibition test (HI) as detailed under Example 1.2.1. The conclusions are as follows:

For the two A/H3N2 strains and for all groups, a boost of HI titers was observed in all vaccinated groups after immunization.

Post-immunization with A/Panama/2007/99, statistically significant higher anti-A/Panama/2007/99 HI titers were observed when the Trivalent Split vaccine was adjuvanted with MPL/QS21 in liposomes compared to the Trivalent Split Plain vaccine.

After immunization with A/Panama/2007/99, only the Trivalent Split adjuvanted with MPL/QS21 in liposomes was able to significantly increase HI titers to the heterologous strain A/Wyoming/3/2003 (cross-reactivity before challenge with this drift strain).

After challenge with A/Wyoming3/2003, an significant increase of anti-A/Wyoming/3/2003 HI titers was observed for both Trivalent Split Plain and Trivalent Split adjuvanted with MPL/QS21 in liposomes.

For A/New Caledonia/20/99 and B/Shangdong/7/97 strains, statistically significant higher HI titers were observed when the Trivalent Split was adjuvanted with MPL/QS21 in liposomes compared to the Trivalent Split Plain vaccine.

III.3.2. Viral Shedding (FIG. 3).

Viral titration of nasal washes was performed on 6 animals per group as detailed under Example 1.2.3. The nasal washes were performed by administration of 5 ml of PBS in both nostrils in awake animals. The inoculation was collected in a Petri dish and placed into sample containers at −80° C.

Two days after challenge, statistically significant lower viral shedding was observed with Trivalent Split adjuvanted with MPL/QS21 in liposomes compared to Trivalent Split Plain.

On Day 49 (7 days Post-challenge), no virus was detected in nasal washes.

III.3.3. Conclusion of the Experiment

Higher humoral responses (HI titers) were observed with Trivalent Split adjuvanted with MPL/QS21 in liposomes compared to the Trivalent Split Plain for all 4 strains.

After immunization with A/Panama/2007/99, only the Trivalent Split adjuvanted with MPL/QS21 in liposomes was able to significantly increase HI titers to the heterologous strain A/Wyoming/3/2003 (cross-reactivity before challenge with this strain).

MPL/QS21 in liposomes formulations showed added benefit in terms of protective efficacy in ferrets (lower viral shedding after heterologous challenge). The cross-reaction observed after immunization with Trivalent Split MPL/QS21 in liposomes against the drift strain used for the challenge seemed to correlate with the protection effect observed in these ferrets.

EXAMPLE IV

Pre-clinical Evaluation of Adjuvanted and Unadjuvanted Influenza Vaccines in C57Bl/6 Primed Mice IV.1. Experimental Design and Objective C57Bl/6 mice primed with heterologous strains were used for this experiment.

The purpose was to compare the humoral (HI titers) and CMI (ICS, intracellular cytokine staining) immune responses induced by a GlaxoSmithKline commercially available Trivalent split vaccine (Fluarix™) versus a Trivalent subunit vaccine (Chiron's vaccine Agrippal™) as well as the CMI response obtained with these vaccines adjuvanted with Liposomes containing 3D-MPL alone, DQS21 (QS21 in liposomes, i.e. detoxified QS21) alone or MPL/QS21 in liposomes. In the example hereinbelow, formulations were prepared starting from the split monobulks to reach the same composition than in the Fluarix vaccine and not from commercially available Fluarix doses. The formulations obtained were called "Fluarix like".

IV.1.1. Treatment/Group

Female C57Bl/6 mice aged 6-8 weeks were obtained from Harlan Horst, Netherland. Mice were primed on day 0 with heterosubtypic strains (5 µg HA whole inactivated H1 N1 A/Beijing/262/95, H3N2 A/Panama/2007/99, B/Shangdong/7/97). On day 28, mice were injected intramuscularly with 1.5 µg HA Trivalent split (A/New Caledonia/20/99, A/Wyoming/3/2003, B/Jiangsu/10/2003) plain or adjuvanted (see groups in Tables 4 to 6 below).

TABLE 4

| Gr | Antigen/Formulation | Other treatment |
|---|---|---|
| 1 | Trivalent split*/Plain (un-adjuvanted) = Fluarix like | Heterologous priming D0 |
| 2 | Trivalent split*/Liposomes containing 3D-MPL | Heterologous priming D0 |
| 3 | Trivalent split*/DQS21 | Heterologous priming D0 |
| 4 | Trivalent split*/MPL/QS21 in liposomes | Heterologous priming D0 |
| 5 | Aggripal ™ (sub-unit) | Heterologous priming D0 |

TABLE 4-continued

| Gr | Antigen/Formulation | Other treatment |
|---|---|---|
| 6 | Aggripal ™ (sub-unit)/Liposomes containing 3D-MPL | Heterologous priming D0 |
| 7 | Aggripal ™ (sub-unit)/DQS21 | Heterologous priming D0 |
| 8 | Aggripal ™ (sub-unit)/MPL/QS21 in liposomes | Heterologous priming D0 |
| 9 | PBS | Heterologous priming D0 |

*Fluarix like.
16 mice/group

IV.1.2. Preparation of the Vaccine Formulations

Formulation for Group 1:

PBS 10 fold concentrated (pH 7.4 when one fold concentrated) as well as a mixture containing Tween 80, Triton X-100 and VES (quantities taking into account the detergents present in the strains) are added to water for injection. After 5 min stirring, 15 µg of each strain H1N1, H3N2 and 15 µg of B strain are added with 10 min stirring between each addition. The formulation is stirred for minimum 15 minutes and stored at 4° C. if not administered directly.

Formulation for Group 2:

PBS 10 fold concentrated (pH 7.4 when one fold concentrated) as well as a mixture containing Tween 80, Triton X-100 and VES (quantities taking into account the detergents present in the strains) are added to water for injection. After 5 min stirring, 15 µg of each strain H1N1, H3N2 and 15 µg of B strain are added with 10 min stirring between each addition. The formulation is stirred for 15 minutes. Concentrated liposomes containing 3D-MPL (made of DOPC 40 mg/ml, Cholesterol 10 mg/ml, 3D-MPL 2 mg/ml) are added to reach a final MPL concentration of 50 µg per dose. The formulation is then stirred minimum 15 minutes and stored at 4° C. if not administered directly.

Formulation for Group 3:

PBS 10 fold concentrated (pH 7.4 when one fold concentrated) as well as a mixture containing Tween 80, Triton X-100 and VES (quantities taking into account the detergents present in the strains) are added to water for injection. After 5 min stirring, 15 µg of each strain H1N1, H3N2 and 15 µg of B strain are added with 10 min stirring between each addition. The formulation is stirred for 15 minutes. A premix made of liposomes (made of DOPC 40 mg/ml, Cholesterol 10 mg/ml) and QS21 called "DQS21" is then added to reach a QS21 concentration of 50 µg per dose. This premix is incubated at least for 15 minutes prior to addition to the trivalent split mixture. The formulation is stirred for minimum 15 minutes and stored at 4° C. if not administered directly.

Formulation for Group 4:

PBS 10 fold concentrated (pH 7.4 when one fold concentrated) as well as a mixture containing Tween 80, Triton X-100 and VES (quantities taking into account the detergents present in the strains) are added to water for injection. After 5 min stirring, 15 µg of each strain H1N1, H3N2 and 15 µg of B strain are added with 10 min stirring between each addition. The formulation is stirred for 15 minutes. A mixture made of liposomes containing 3D-MPL (made of DOPC 40 mg/ml, Cholesterol 10 mg/ml, 3D-MPL 2 mg/ml) and QS21 is then added to reach QS21 and MPL concentrations of 50 µg per dose. This mixture is incubated at least for 15 minutes prior to addition to the trivalent split mixture. The so called "trivalent split MPL/QS21 in liposomes" formulation is stirred for minimum 15 minutes and stored at 4° C. if not administered directly.

Remark: In groups 1 to 4, PBS 10 fold concentrated is added to reach isotonicity and is 1 fold concentrated in the final volume. H2O volume is calculated to reach the targeted volume.

Formulation for Group 5:

One Aggripal™ dose is mixed with equal volume of PBS mod pH 7.4. The formulation is stirred for minimum 15 minutes and stored at 4° C. if not administered directly.

Formulation for Group 6:

PBS pH 7.4 and one Aggripal™ dose are mixed. Liposomes containing 3D-MPL (made of DOPC 40 mg/ml, Cholesterol 10 mg/ml, 3D-MPL 2 mg/ml) are then added under stirring to reach the equivalent of 50 µg of MPL per dose. The formulation is stirred for minimum 15 minutes and stored at 4° C. if not administered directly.

Remark: PBS is added to reach isotonicity in the final volume. Aggripal is half the formulation volume.

Formulation for Group 7:

PBS pH 7.4 and one Aggripal™ dose are mixed. A premix of liposomes (made of DOPC 40 mg/ml, Cholesterol 10 mg/ml) and QS21 so called "DQS21" is then added under stirring to reach the equivalent of 50 µg of QS21. This premix is incubated for at least 15 minutes prior to addition. The formulation is stirred minimum 15 minutes and stored at 4° C. if not administered directly.

Remark: PBS is added to reach isotonicity in the final volume. Aggripal™ is half the formulation volume.

Formulation for Group 8:

PBS pH 7.4 and one Aggripal™ dose are mixed. A premix of so called "DQS21-MPLin" is added under stirring to the formulation. The DQS21-MPLin premix is a mixture of liposomes (made of DOPC 40 mg/ml, cholesterol 10 mg/ml, MPL 2 mg/ml) and the immunostimulant QS21. This premix is incubated for at least 15 minutes prior to addition to the Aggripal/PBS mixture. The quantity of MPL and QS21 in the formulation is 50 µg each. The formulation is stirred minimum 15 minutes and stored at 4° C. if not administered directly.

Remark: PBS is added to reach isotonicity in the final volume. Aggripal is half the formulation volume.

IV.1.3. Read-outs (Table 7)

TABLE 7

| Read-out | Timepoint | Sample type | In/Po | Analysis method |
|---|---|---|---|---|
| Anti-HI antibodies (HI titers) | Day 21 Post-Immunization (Day 49) | Sera | In | Hemagglutination Inhibition test |
| CD4, CD8, IL-2, IFN-γ (FACS) | Day 7 Post-Immunization (Day 35) | PBLs | Po | Intracellular cytokine staining (ICS) |

In = Individual/Po = Pool

IV.2. Results

IV.2.1. Humoral Response (HI Titers 21 Days Post Immunization).

Humoral Responses by HI Titers—FIG. 4.

Haemagglutination inhibition activity against the three vaccine strains (A/New Caledonia/20/99, A/Wyoming/3/2003, B/Jiangsu/10/2003) was detected in sera from 8 animals per group at Day 21 Post-immunization.

Compared to mice immunized with PBS, an increase in HI titers was observed after immunization with all Flu vaccine candidates tested for all three strains (Trivalent split or Trivalent subunit vaccine).

For all three strains, statistically significant higher HI titers were observed in mice immunized with Trivalent split adjuvanted with DQS21 alone or MPL/QS21 in liposomes compared to mice immunized with Trivalent split Flu plain or adjuvanted with Liposomes containing 3D-MPL alone. The ranking for the humoral response was as follow: (MPL/QS21 in liposomes=DQS21 alone)>(Liposomes containing 3D-MPL alone=Plain)>PBS For all three strains, statistically significant higher HI titers were observed in mice immunized with Trivalent subunit adjuvanted with DQS21 alone, Liposomes containing 3D-MPL alone or MPL/QS21 in liposomes compared to mice immunized with Trivalent split plain. The ranking for the humoral response was as follow: (MPL/QS21 in liposomes=DQS21 alone=Liposomes containing 3D-MPL alone)>Plain>PBS.

TABLE 5

Final composition of the formulations 1 to 4 prepared with split strains (for 1 ml)

| Group | Antigen | Tween 80 | Triton X-100 | VES | DOPC | Cholesterol | MPL | QS21 |
|---|---|---|---|---|---|---|---|---|
| 1 | H1N1: 15 µg H3N2: 15 µg B: 17.5 µg | 750 µg | 110 µg | 100 µg | — | — | — | — |
| 2 | Identical to 1 | Identical to 1 | 110 µg | 100 µg | 1 mg | 250 µg | 50 µg | — |
| 3 | Identical to 1 | Identical to 1 | 110 µg | 100 µg | 1 mg | 250 µg | — | 50 µg |
| 4 | Identical to 1 | Identical to 1 | 110 µg | 100 µg | 1 mg | 250 µg | 50 µg | 50 µg |

TABLE 6

Final composition of the formulations 5 to 8 prepared with Aggripal ™ vaccine (1 ml)

| Group | Antigen | DOPC | Cholesterol | MPL | QS21 |
|---|---|---|---|---|---|
| 5 | 1 dose of Aggripal vaccine | — | — | — | — |
| 6 | Identical to 5 | 1 mg | 250 µg | 50 µg | — |
| 7 | Identical to 5 | 1 mg | 250 µg | — | 50 µg |
| 8 | Identical to 5 | 1 mg | 250 µg | 50 µg | 50 µg |

Trivalent split and Trivalent subunit induced similar HI titers when formulations were not adjuvanted or adjuvanted with DQS21 alone or MPL/QS21 in liposomes.

IV.2.2. Cell-mediated Immune Response (ICS at Day 7 Post Immunization).

CD4 T Cell Responses—FIG. 5

PBMCs from 8 mice per group were harvested at Day 7 Post-immunization and tested in 4 pools of 2 mice/group.

In terms of Flu whole virus-specific total CD4+ T cells (expressing IL-2, IFN-γ and both cytokines):

Whatever the formulation, identical CD4+ T cell responses were observed between the Trivalent split and Trivalent subunit vaccines.

Higher CD4+ T cell responses were observed for Trivalent formulations (split or subunit) adjuvanted with MPL/QS21 in liposomes when compared to Trivalent formulations (split or subunit) plain or adjuvanted with Liposomes containing 3D-MPL alone or DQS21 alone.

For the cellular response induced by a Trivalent formulation (split or subunit), there is a synergic effect of Liposomes containing 3D-MPL+DQS21 compared to DQS21 alone or Liposomes containing 3D-MPL alone.

The ranking for the cellular response was as follow: MPL/QS21 in liposomes>(Liposomes containing 3D-MPL alone=DQS21 alone=Plain=PBS).

IV.3. Summary of Results and Conclusions

For all three strains, statistically significant higher HI titers were observed in mice immunized with Trivalent formulations (split or subunit) adjuvanted with DQS21 alone or MPL/QS21 in liposomes compared to mice immunized with Trivalent formulations (split or subunit) plain. Liposomes containing 3D-MPL alone seemed to induced higher humoral response when formulated with Trivalent subunit than Trivalent split.

Whatever the formulation, similar CD4+ T cell responses were obtained for Trivalent split (Fluarix) and Trivalent subunit (Agrippal).

Trivalent formulations (split or subunit) adjuvanted with MPL/QS21 in liposomes induced higher CD4+ T cell responses compared to Trivalent formulations (split or subunit) plain or adjuvanted with Liposomes containing 3D-MPL alone or QS21 in liposomes (DQS21) alone.

EXAMPLE V

Preclinical Comparison of a Vaccine Containing a Split Influenza Antigen Preparation Adjuvanted with 3D-MPL/QS21 in a Liposomal Formulation (3D-MPL at Two Different Concentrations)

V.1—Mice.

V.1.1—Experimental Design and Objective.

C57B1/6 mice primed with heterologous strains were used for this experiment. The purpose was to analyse the humoral (HI titers) and CMI (ICS, intracellular cytokine staining) immune responses induced by a GlaxoSmithKline commercially available Trivalent split vaccine (Fluarix™) in un-adjuvanted form, and when adjuvanted with liposomes containing two different concentrations of 3D-MPL and QS21.

V.1.2 Treatment/Group

Female C57B1/6 mice aged 8 weeks were obtained from Harlan Horst, Netherlands. Mice were primed intranasally on day 0 with heterosubtypic strains (whole inactivated A/Beijing/262/95, H3N2 A/Panama/2007/99, B/Shandong/7/97). On day 28, mice were injected intramuscularly with Trivalent Split (A/New Caledonia,A/Wyoming, B/Jiangsu) plain or adjuvanted with two different concentrations of immunostimulants in liposomal formulations (see groups in table 8 below).

TABLE 8

| Group | Antigen(s) + dosage | Formulation + dosage | Other treatments |
|---|---|---|---|
| 1 | Trivalent Split Flu - strain/50 µl 1.5 µg/ | Plain | Heterologous priming D0 whole inactivated 5 µg/20 µl intranasally |
| 2 | Trivalent Split Flu - 1.5 µg/strain/50 µl | Liposomes containing 3D-MPL 50 µg per 0.5 ml dose | Heterologous priming D0 whole inactivated 5 µg/20 µl intranasally |
| 3 | Trivalent Split Flu - 1.5 µg/strain/50 µl | DQS21 50 µg per 0.5 ml dose | Heterologous priming D0 whole inactivated 5 µg/20 µl intranasally |
| 4 | Trivalent Split Flu - 1.5 µg/strain/50 µl | MPL and QS21 25 µg per 0.5 ml dose | Heterologous priming D0 whole inactivated 5 µg/20 µl intranasally |
| 5 | Trivalent Split Flu - 1.5 µg/strain/50 µl | MPL and QS21 50 µg per 0.5 ml dose | Heterologous priming D0 whole inactivated 5 µg/20 µl intranasally |
| 6 | PBS | None | Heterologous priming D0 whole inactivated 5 µg/20 µl intranasally |

Formulations were prepared as in example IV.

V.1.3—Results.

Humoral Responses by HI Titers—FIG. 24.

Hemagglutination inhibition activity against the 3 vaccine strains was detected in sera from 9 animals/group on day 21 post immunisation.

Compared to mice immunized with PBS, an increase in HI titres was observed after immunization with all Flu vaccine candidates tested for all three strains.

For all three strains, statistically significant higher HI titers were observed in mice immunized with Trivalent Split adjuvant with MPL and QS21 at either concentration compared to mice immunized with the Trivalent Flu Split Plain (p value max=0.03)

No statistically significant difference was observed between the two liposomal adjuvant groups adjuvant groups Cell-mediated Immune Response (ICS at Day 7 Post-immunisation)—FIG. 25.

PBMC's from 9 mice/group were harvested 7 days post-immunisation and tested in three pools of 3 mice/group. In terms of whole Flu virus-specific CD4+ T cells expressing IL-2, IFN-γ or both cytokines:

As can be seen from FIG. 25 the highest IFN-γ CD4+ T cell-specific responses were obtained after immunization with trivalent split adjuvanted with the highest concentration of immunostimulants. However, IL2 and IL2+IFN-γ T cell responses were similar between the two concentrations of immunostimulants.

EXAMPLE VI

Clinical Trial in an Elderly Population Aged Over 65 Years with a Vaccine Containing a Split Influenza Antigen Preparation Adjuvanted with MPL/QS21 in a Liposomal Formulation (3D-MPL at Two Different Concentrations)

VI.1. Study Design and Objectives

An open, randomized phase I/II study to demonstrate the non inferiority in term of cellular mediated immune response of GlaxoSmithKline Biologicals influenza candidate vaccines containing various adjuvants administered in elderly population (aged 65 years and older) as compared to Fluarix™ (known as α-Rix™ in Belgium) administered in adults (18-40 years)

Four parallel groups were assigned:
- 75 adults (aged 18-40 years) in one control group receiving one dose of Fluarix™ (Fluarix group)
- 200 elderly subjects (aged 65 years and older) randomized 3:3:2 into three groups:
  - one group with 75 subjects receiving influenza vaccine adjuvanted with AS01B
  - One group with 75 subjects receiving influenza vaccine adjuvanted with AS01E
  - Reference Flu group with 50 subjects receiving one dose of Fluarix™

Primary Objective

The primary objective is to demonstrate the non inferiority 21 days post-vaccination of the influenza adjuvanted vaccines administered in elderly subjects (aged 65 years and older) as compared to Fluarix™ administered in adults (aged 18-40 years) in terms of frequency of influenza-specific CD4 T-lymphocytes producing at least two different cytokines (CD40L, IL-2, TNF-α, IFN-γ).

Secondary Objectives

The secondary objectives are:
1) To evaluate the safety and reactogenicity of vaccination with candidate influenza vaccines adjuvanted during 21 days following the intramuscular administration of the vaccine in elderly subjects (aged 65 years and older). Fluarix™ is used as reference.
2) To evaluate the humoral immune response (anti-haemagglutinin titre) 21, 90 and 180 days after vaccination with influenza candidate vaccines adjuvanted. Fluarix™ is used as reference.

Tertiary Objective

The tertiary objective is to evaluate the cell mediated immune response (production of IFN-γ, IL-2, CD40L, and TNF-α and memory B-cell response) 21, 90 and 180 days after vaccination with adjuvanted influenza-vaccines. Fluarix™ is used as reference.

VI.2. Vaccine Composition and Administration

Two different adjuvants have been used:
1. AS01B a liposome-based adjuvant containing 50 μg MPL and QS21
2. AS01E a two-fold diluted formulation of AS01B Control: full dose of Fluarix™ by IM administration.

All vaccines are intended for intramuscular administration. The strains used in the five vaccines are the ones that have been recommended by the WHO for the 2005-2006 Northern Hemisphere season, i.e. A/New Caledonia/20/99 (H1N1), A/New York/7/2004 (H3N2) and B/Jiangsu/10/2003.

The three inactivated split virion antigens (monovalent bulks) used in formulation of the adjuvanted influenza candidate vaccine, are exactly the same as the active ingredients used in formulation of the commercial Fluarix™/α-Rix™-GSK Bio's split virion inactivated influenza vaccine. They are derived from egg-grown viruses. The influenza strains are the recommended ones for the 2005/2006 season, as used in the formulation of the commercial Fluarix™/α-Rix™ 2005/2006.

The strains used in the three vaccines are the ones that have been recommended by the WHO for the 2005-2006 Northern Hemisphere season i.e.
- A/New Caledonia/20/99 ($H_1N_1$) IVR-116
- A/New York/55/2004 (H3N2) NYMC X-157
- B/Jiangsu/10/2003

Like Fluarix™/α-Rix™ the adjuvanted vaccine contains 15 μg haemagglutinin (HA) of each influenza virus strain per dose.

VI.2.1. Description of the AS01B Adjuvanted Vaccine Lots

The AS01B-adjuvanted influenza candidate vaccine is a 2 components vaccine consisting of a concentrated trivalent inactivated split virion antigens presented in a glass vial and of a glass vial containing the AS01B adjuvant. At the time of injection, the content of the adjuvant vial is withdrawn and injected into the vial that contains the concentrated trivalent inactivated split virion antigens. After mixing the content is withdrawn into the syringe and the needle is replaced by an intramuscular needle. The used needle is replaced by an intramuscular needle and the volume is corrected to 1 ml. One dose of the reconstituted AS01B-adjuvanted influenza candidate vaccine corresponds to 1 mL.

The AS01B-adjuvanted influenza candidate vaccine is a preservative-free vaccine.

VI.2.2. Composition of the AS01B Adjuvanted Clinical Lot

One dose of the reconstituted AS01B-adjuvanted influenza vaccine corresponds to 1 mL. Its composition is given in Table 8. It contains 15 μg HA of each influenza virus strain as in the registered Fluarix™/α-Rix® vaccine.

TABLE 8

Composition (influenza and adjuvant components) of the reconstituted AS01B adjuvanted influenza candidate vaccine

| Component | Quantity per dose | Analytical Reference |
|---|---|---|
| ACTIVE INGREDIENTS | | |
| Inactivated split virions | | |
| A/New Caledonia/20/99 (H1N1) IVR-116 | 15 μg HA | Ph. Eur. 158 |
| A/New York/55/2004 (H3N2) NYMC X-157 | 15 μg HA | Ph. Eur. 158 |
| B/Jiangsu/10/2003 | 15 μg HA | Ph. Eur. 158 |
| AS01B ADJUVANT | | |
| Liposomes | | |
| dioleyl phosphatidylcholine (DOPC) | 1000 μg | GSK Bio 3217 |
| Cholesterol | 250 μg | Ph. Eur. 0993 |
| MPL | 50 μg | GSK Bio 2972 |
| QS21 | 50 μg | GSK Bio 3034 |

VI.2.3. Production Method of the AS01B Adjuvanted Vaccine Lot

The manufacturing of the AS01B-adjuvanted influenza vaccine consists of three main steps:
- Formulation of the trivalent final bulk (2× concentrated) without adjuvant and filling in the antigen container
- Preparation of the AS01B adjuvant
- Extemporaneous reconstitution of the AS01B adjuvanted split virus vaccine.

Formulation of the Trivalent Final Bulk without Adjuvant and Filling in the Antigen Container The volumes of the three monovalent bulks are based on the HA content measured in each monovalent bulk prior to the formulation and on a target volume of 1320 ml.

Concentrated phosphate buffered saline PO4 Na/$K_2$ (80 μl/dose) and a pre-mixture of Tween 80, Triton X-100 and α-tocopheryl hydrogen succinate are diluted in water for injection. The three concentrated monobulks (A/New Caledonia/20/99 IVR-116, A/New York/55/2004 NYMC X-157, B/Jiangsu/10/2003) are then successively diluted in the resulting phosphate buffered saline/Tween 80—Triton X-100—α-tocopheryl hydrogen succinate solution (pH 7.8, 81 mM NaCl, 1.56 mM KCl, 4.79 mM $Na_2HPO_4$, 0.87 mM KH$_2$PO$_4$, 7.2 mM NaH$_2$PO$_4$, 72.8 mM K$_2$HPO$_4$, 750 µg/ml Tween 80, 110 µg/ml Triton X-100 and 100 µg/ml α-tocopheryl hydrogen succinate) in order to have a final concentration of 30 µg HA of A (H1 N1 and H3N2) strains per ml of trivalent final bulk (15 µg HA/A strain/500 µl trivalent final bulk) and 35 µg HA of B strain (17.5 µg HA/B strain/500 µl trivalent final bulk). Between addition of each monovalent bulk, the mixture is stirred for 10-30 minutes at room temperature. After addition of the last monovalent bulk and 15-30 minutes of stirring, the pH is checked and adjusted to 7.65±0.25 with HCl or NaOH.

The trivalent final bulk of antigens is aseptically filled into 3-ml sterile Type I (Ph. Eur.) glass vials. Each vial contains a volume of 600 µl (500 µl+100µ overfill).

Preparation of AS01B Adjuvant Bulk and Filling in the Adjuvant Container

The adjuvant AS01B is prepared by mixing of two components: QS21 and liposomes containing MPL. The preparation of each of these components is summarized below. QS21 is a triterpene glycoside, obtained from the tree bark of *Quillaja saponaria*, and is produced by Aquila Worchester, Mass., USA (now Antigenics).

QS21 is provided to GSK Biologicals as a lyophillised powder. The preparation of QS21 at GSK Bio consists of suspension of QS21 powder in water for injection at a concentration of approximately 5 mg/mL, pH adjustment to pH 6.0±0.2 and sterile filtration. The liquid bulk QS21 is stored at −20° C. in polyethylene containers.

MPL is the 3-O-deacyl-4'-monophosphoryl lipid A obtained by sequential acid and base hydrolyses of the lipopolysaccharide from the Re595 strain of *Salmonella minnesota*. It is produced by GSK Biologicals, Hamilton, Mont. Bulk MPL is supplied as the lyophilized salt of triethylamine (TEA).

In the process of production of MPL-containing liposomes, DOPC (Dioleyl phosphatidylcholine), cholesterol and MPL are dissolved in ethanol. A lipid film is formed by solvent evaporation under vacuum. Phosphate Buffer Saline made of 9 mM Na$_2$HPO$_4$, 41 mM KH$_2$PO$_4$, 100 mM NaCl at pH 6.1 is added and the mixture is submitted to prehomogenization followed by high pressure homogenization at 15,000 psi (+1-20 cycles). This leads to the production of liposomes, which are sterile filtered through a 0.22 µm membrane in an aseptic (class 100) area. The sterile product is then distributed in sterile glass containers and stored in the cold room (+2 to +8° C.).

Sterile bulk preparation of liposomes is mixed with sterile QS21 bulk solution. After 30 min stirring, this mixture is added to a mixture of water for injection and phosphate 500 mM, NaCl 1M pH 6.1 when diluted 10 times. Quantity of the phosphate 500 mM, NaCl 1M pH 6.1 when diluted 10 times, is calculated to reach isotonicity in the final volume. The pH is checked. The adjuvant is then sterile filtered (0.22 µm) and aseptically distributed into vials. The vials are stored at +2 to +8° C.

The AS01B diluent is an opalescent colorless liquid, free from foreign particles, contained in a sterile, type 1 glass vial. The target fill for each vial is 0.7 ml in order to meet the specification (≥0.5 ml).

Extemporaneous Reconstitution of the AS01B Adjuvanted Split Virus Vaccine

At the time of injection, the content of the vial containing the adjuvant is withdrawn and is injected into the vial that contains the concentrated trivalent inactivated split virion antigens. After mixing, the content is withdrawn into the syringe and the needle is replaced by an intramuscular needle, and the volume is corrected to 1 ml. One dose of the reconstituted AS01B-adjuvanted influenza candidate vaccine corresponds to 1 mL.

VI.2.4. Description of the AS01E Adjuvanted Vaccine Lots

The AS01E adjuvanted influenza candidate vaccine is a 3 components vaccine consisting of a concentrated trivalent inactivated split virion antigens presented in a glass vial, a glass vial containing the AS01B adjuvant and a glass vial containing the diluent (sodium chloride solution for injection) for the two-fold dilution of AS01B.

To prepare the AS01E adjuvant the content of the diluent vial is withdrawn with a syringe and injected into the vial containing the AS01B adjuvant, followed by mixing. At the time of injection, 600 µl AS01E adjuvant is withdrawn with a syringe from the AS01E vial and injected into the vial that contains the concentrated trivalent inactivated split virion antigens. After mixing the content is withdrawn into the syringe and the needle is replaced by an intramuscular needle. One dose of the reconstituted AS01B-adjuvanted influenza candidate vaccine corresponds to 1 mL.

The AS01E-adjuvanted influenza candidate vaccine is a preservative-free vaccine.

VI.2.5. Composition of the AS01E Adjuvanted Clinical Lot

One dose of the reconstituted AS01E-adjuvanted influenza vaccine corresponds to 1 mL. Its composition is given in Table 9. It contains 15 µg HA of each influenza virus strain as in the registered Fluarix™/α-Rix® vaccine.

TABLE 9

Composition (influenza and adjuvant components) of the reconstituted AS01E adjuvanted influenza candidate vaccine

| Component | Quantity per dose | Analytical Reference |
|---|---|---|
| ACTIVE INGREDIENTS | | |
| Inactivated split virions | | |
| A/New Caledonia/20/99 (H1N1) IVR-116 | 15 µg HA | Ph. Eur. 158 |
| A/New York/55/2004 (H3N2) NYMC X-157 | 15 µg HA | Ph. Eur. 158 |
| B/Jiangsu/10/2003 | 15 µg HA | Ph. Eur. 158 |
| AS01B ADJUVANT | | |
| Liposomes | | |
| dioleyl phosphatidylcholine (DOPC) | 500 µg | GSK Bio 3217 |
| Cholesterol | 125 µg | Ph. Eur. 0993 |
| MPL | 25 µg | GSK Bio 2972 |
| QS21 | 25 µg | GSK Bio 3034 |

VI.2.6. Production Method of the AS01E Adjuvanted Vaccine Lot

The manufacturing of the AS01B-adjuvanted influenza vaccine consists of three main steps:

Formulation of the trivalent final bulk (2× concentrated) without adjuvant and filling in the antigen container Preparation of the AS01B adjuvant Preparation of the AS01E adjuvant followed by extemporaneous reconstitution of the AS01E adjuvanted split virus vaccine.

Formulation of the Trivalent Final Bulk without Adjuvant and Filling in the Antigen Container Reference is made to section V.2.3 for the AS01B adjuvanted influenza vaccine.

Preparation of AS01B Adjuvant Bulk and Filling in the Adjuvant Container

Reference is made to section V.2.3 for the AS01B adjuvanted influenza vaccine.

Extemporaneous Reconstitution of the AS01E Adjuvanted Split Virus Vaccine

To prepare the AS01E adjuvant the content of the diluent vial is withdrawn with a syringe and injected into the vial containing the AS01B adjuvant, followed by mixing. At the time of injection, 600 μl AS01E adjuvant is withdrawn with a syringe from the AS01E vial and injected into the vial that contains the concentrated trivalent inactivated split virion antigens. After mixing the content is withdrawn into the syringe and the needle is replaced by an intramuscular needle. One dose of the reconstituted AS01E-adjuvanted influenza candidate vaccine corresponds to 1 mL.

Four scheduled visits per subject: at days 0, 21, 90 and 180 with blood sample collected at each visit to evaluate immunogenicity.

Vaccination schedule: one injection of influenza vaccine at day 0

VI.2.7—Immunological Assays

Haemagglutination—Inhibition Assay

The immune response is determined by measuring Haemagglutination inhibition (HI) antibodies using the method described by the WHO collaborating Centre for influenza, Centres for Diseases Control, Atlanta, USA (1991). Antibody titre measurements were conducted on thawed frozen serum samples with a standardised and comprehensively validated micromethod using 4 haemagglutination-inhibiting units (4 HIU) of the appropriate antigens and a 0.5% fowl erythrocyte suspension. Non-specific serum inhibitors were removed by heat treatment and receptor-destroying enzyme. The sera obtained were evaluated for HI antibody levels. Starting with an initial dilution of 1:10, a dilution series (by a factor of 2) was prepared up to an end dilution of 1:20480. The titration end-point was taken as the highest dilution step that shows complete inhibition (100%) of haemagglutination. All assays were performed in duplicate.

Cytokine Flow Cytometry (CFC) Used to Evaluate the Frequency of Cytokine(s)—Positive CD4 or CD8 T Lymphocytes.

Peripheral blood antigen-specific CD4 and CD8 T cells can be restimulated in vitro to produce CD40L, IL-2, TNF-α and IFN-γ if incubated with their corresponding antigen. Consequently, antigen-specific CD4 and CD8 T cells can be enumerated by flow cytometry following conventional immunofluorescence labelling of cellular phenotype as well as intracellular cytokines production. In the present study, influenza vaccine antigens will be used as antigens to restimulate influenza-specific T cells. Results will be expressed as a frequency of cytokine(s)-positive CD4 or CD8 T cell within the CD4 or CD8 T cell sub-population.

ELISPOT Used to Evaluate Frequency of Memory B-cell

The B cell Elispot technology allows the quantification of memory B cells specific to a given antigen. Memory B cells can be induce to differentiate into plasma cells in-vitro following cultivation with CpG for 5 days. In-vitro generated antigen-specific plasma cells can therefore be enumerated using the B-cell elispot assay. Briefly, in-vitro generated plasma cells are incubated in culture plates coated with antigen. Antigen-specific plasma cells will form antibody/antigen spots, which can be detected by conventional immuno-enzymatic procedure. In the present study, influenza vaccine strains or anti-human immunoglobulin are used to coat culture plates in order to enumerate anti-influenza or IgG secreting plasma cells, respectively. Results are expressed as a frequency of antigen-specific plasma within a million of IgG-producing plasma cells.

Exploratory Characterisation of PBMCs

The expression of selected surfact/activation markers (i.e. CD4., CD8, CD45RO, CD45 RA, CD28, CD27 or some KIR) can be performed. The function of vaccine-induced T lymphocytes can be addressed by the analysis of homing markers (i.e. CCR7, CXCR5), of cytokines (T helper 1 or T helper 2 cytokines), or by analysing the expression of factors associated with regulatory functions such as Foxp3, CTLA-4, or TGFβ. In particular, the CD8+CD28− population or other regulatory T cell populations can be analysed in relation the humoral, B and T cell responses to the vaccine antigen.

VI.3. Immunogenicity Results

VI.3.1. CMI Endpoints and Results

In order to characterize the CMI response after vaccination with the adjuvanted influenza vaccines, CD4 and CD8 T-lymphocytes were restimulated in vitro using antigens from the three vaccine strains (used individually or pooled). Influenza-specific CD4/CD8 T-lymphocytes were enumerated by flow cytometry following conventional immunofluorescence labelling of intracellular cytokines production (IL-2, IFN-γ, TNF-α and CD40L).

Evaluation of the Primary Endpoint.

At day 21: CMI response in all subjects in terms of frequency of influenza-specific CD4 T-lymphocyte per $10^6$ in tests producing at least two different cytokines (IL-2, IFN-γ, TNF-α and CD40L).

For the evaluation of CMI response, frequency of influenza-specific CD4 are analysed as follows:

Using the non-inferiority approach, the non inferiority of at least one influenza adjuvanted candidate vaccine (administered to elderly aged≥65 years—the group termed Flu elderly or Flu ELD) compared to Fluarix™ (administered to adults aged 18-40 years—the group termed Flu Young or Flu YNG) was reached when the upper limit of two-sided 98.75% confidence interval on Geometric Mean (GM) ratio (between the Fluarix™ (18-40 years) group and the influenza adjuvanted candidate vaccine 65 years group) in terms of frequency of influenza-specific CD4 T-cells producing at least two cytokines at day 21) was below 2.0

$$UL_{98.75\% CI}\left(\frac{GM_{Fluarix\ adults}}{GM_{influenzaAdjuvanted}}\right) < 2$$

The 98.75% CI of GM ratios, 21 days after vaccination, was computed using an analysis of covariance (ANCPVA) model on the logarithm 10 transformation of the frequencies. The ANCOVA model included the vaccine group as fixed effect (Fluarix™ (18-40 years) versus the influenza adjuvanted candidate vaccine 65 years)) and the pre-vaccination frequency as a regressor. The GM ratio and their 98.75% CI are derived as exponential-transformation of the corresponding group contrast in the model. The 98.75% CI for the adjusted GM is obtained by exponential-transformation of the 98.75% CI for the group least square mean of the above ANCOVA model.

Results—Inferential Analysis (Table 10)

The adjusted GM and GM ratios (with their 98.75% CI) of influenza-specific CD4 T-lymphocyte producing at least two cytokines (IL-2, IFN-γ, TNF-α and CD40L) at day 21, after in vitro restimulation with "pooled antigens II", are presented in Table 10. For each adjuvanted influenza vaccine, the upper limit of two-sided 98.75% CI of GM ratio is far below the clinical limit of 2.0. This shows the non-inferiority of both adjuvanted influenza vaccines administered to elderly subjects compared to the Fluarix™ vaccine administered in adults aged between 18 and 40 years in term of post-vaccination frequency of influenza-specific CD4.

TABLE 10

Adjusted GM ratio of influenza-specific CD4 T cellsproducing at least two cytokines after restimulation with pooled vaccine antigens, Day 21 (ATP cohort for immunogenicity)

| Flu YNG | | AS01B | | GM ratio (Flu YNG/AS01B) | | |
|---|---|---|---|---|---|---|
| | | | | | 98.8% CI | |
| N | GM | N | GM | Value | LL | UL |
| 74 | 2844.8 | 71 | 2725.6 | 1.04 | 0.79 | 1.38 |

| Flu YNG | | AS01E | | GM ratio (Flu YNG/AS01E) | | |
|---|---|---|---|---|---|---|
| | | | | | 98.8% CI | |
| N | GM | N | GM | Value | LL | UL |
| 74 | 2879.6 | 74 | 2697.0 | 1.07 | 0.79 | 1.44 |

Adjusted GM = geometric mean antibody adjusted for baseline titre;
N = Number of subjects with both pre- and post-vaccination results available;
98.8% CI = 98.8% confidence interval for the adjusted GM ratio (Ancova model: adjustment for baseline);
LL = lower limit;
UL = upper limit;
Data source = Appendix table IIIA Results—Descriptive Analysis (FIG. 6)
The main findings were:
1) Before vaccination the CMI response is higher in young adults than in elderly
2) After vaccination:
   there was a booster effect of the influenza vaccine on the CMI response in young adults (18-40 years)
   the CMI response in the elderly having received the adjuvanted influenza vaccine is comparable to the CMI response of young adults.
The difference between pre and post-vaccination in CD4 T-lymphocytes responses for all cytokines investigated (IL-2, CD40L, TNF-α and IFN-γ) was significantly higher with the adjuvanted vaccines compared to Fluarix™ for all tests.

Analysis of the Tertiary Objective:

In order to evaluate the tertiary end point, the frequency of influenza-specific CD4/CD8 T-lymphocytes and memory B-cells were measured at days 0, 21, 90 and 180.
  The frequency of influenza-specific cytokine-positive CD4/CD8 T-lymphocytes was summarised (descriptive statistics) for each vaccination group at days 0 and 21, for each antigen.
  A Non-parametric test (Wilcoxon test) was used to compare the location of difference between the two groups (influenza adjuvanted vaccine versus Fluarix™) and the statistical p-value is calculated for each antigen at each different test.
  Descriptive statistics in individual difference between day 21/day 0 (Post-/Pre-vaccination) responses is calculated for each vaccination group and each antigen at each different test.
  A Non-parametric test (Wilcoxon test) is used to compare the individual difference Post-/Pre-vaccination) and the statistical p-value will be calculated for each antigen at each different test.
The p-values from Wilcoxon test used to compare the difference in the frequency of influenza-specific CD4 T-lymphocytes are presented in Table 11.

Results—Evaluation of the Tertiary End-point (Table 11)
The main conclusions are:
  Pre-vaccination GM frequencies of influenza-specific CD4 T cells were similar in all groups of elderly subjects but superior in the adults aged between 18 and 40 years.
  In elderly subjects, post-vaccination (day 21) frequency of influenza-specific CD4 T lymphocytes was significantly higher after vaccination with adjuvanted vaccines than with Fluarix™
  Post-vaccination frequency of influenza-specific CD4 T lymphocytes remained lower in elderly subjects vaccinated with AS01B or AS01E adjuvanted vaccines than in adults aged between 18 and 40 years vaccinated with Fluarix™
  Pre-vaccination and post vaccination GM frequency of influenza-specific CD8 T cell was essentially similar in all groups.

TABLE 11

Inferential statistics: p-values from Kruskal-Wallis Tests for CD4 T cells at each time point (ATP Cohort for immunogenicity)

| | P-value | | | |
|---|---|---|---|---|
| | AS01B vs. Flu YNG | | AS01E vs. Flu YNG | |
| Test description | day 0 | day 21 | day 0 | day 21 |
| ALL DOUBLES | <0.0001 | 0.0070 | <0.0001 | 0.0025 |
| CD4OL | <0.0001 | 0.0056 | <0.0001 | 0.0015 |
| IFNγ | <0.0001 | 0.0009 | <0.0001 | 0.0006 |
| IL2 | <0.0001 | 0.0029 | <0.0001 | 0.0021 |
| TFNα | <0.0001 | 0.0295 | <0.0001 | 0.0378 |

| | AS01B vs. Flu ELD | | AS01E vs. Flu ELD | |
|---|---|---|---|---|
| | day 0 | day 21 | day 0 | day 21 |
| ALL DOUBLES | 0.6165 | 0.0004 | 0.8744 | 0.0018 |
| CD4OL | 0.7560 | 0.0005 | 0.9504 | 0.0021 |
| IFNγ | 0.9936 | 0.0008 | 0.9835 | 0.0029 |
| IL2 | 0.6702 | 0.0011 | 0.7855 | 0.0023 |
| TFNα | 0.5450 | 0.0022 | 0.6688 | 0.0040 |

Results—Evaluation of the Humoral Immune Response Endpoints
Observed Variables:
  At days 0, 21, 90 and 180: serum haemagglutination-inhibition (HI) antibody titres, tested separately against each of the three influenza virus strains represented in the vaccine (anti-H1N1, anti-H3N2 & anti-B-antibodies).
  The cut-off value for HI antibody against all vaccine antigens was defined by the laboratory before the analysis (and equals 1:10). A seronegative subject is a subject whose antibody titre is below the cut-off value. A seropositive subject is a subject whose antibody titre is greater than or equal to the cut-off value. Antibody titre below the cut-off of the assay is given an arbitrary value of half the cut-off.
  Based on the HI antibody titres, the following parameters are calculated:
  Geometric mean titres (GMTs) of HI antibody at days 0 and 21, calculated by taking the anti-log of the mean of the log titre transformations.
  Seroconversion factors (SF) at day 21 defined as the fold increase in serum HI GMTs on day 21 compared to day 0.
  Seroconversion rates (SC) at day 21 defined as the percentage of vaccinees with either a pre-vaccination HI titre<1:10 and a post-vaccination titre 1:40, or a pre-vaccination titre 1:10 and a minimum 4-fold increase at post-vaccination titre.

Seroprotection rates (SPR) at day 21 defined as the percentage of vaccinees with a serum HI titre≥40.

The 95% CI for GM is obtained within each group separately. The 95% CI for the mean of log-transformed titre is first obtained assuming that log-transformed titres are normally distributed with unknown variance. The 95% CI for the GM is then obtained by exponential-transformation of the 95% CI for the mean of log-transformed titre.

Missing serological result for a particular antibody measurement is not replaced. Therefore a subject without serological result at a given time point do not contribute to the analysis of the assay for that time point.

Humoral Immune Response Results (FIG. 7 and Table 12)

Pre-vaccination GMTs of HI antibodies for all 3 vaccine strains were within the same range in the 4 treatment groups. After vaccination, there is clear impact of the 2 adjuvants which increase the humoral response in elderly, compared to standard Fluarix in the same population (FIG. 7, shown on a linear scale, but same impact obviously seen if shown on a logarithmic scale).

GMTs are
significantly higher for H1 N1 for AS01E
significantly higher for H3N2 for both adjuvants.
No significant difference was observed in terms of post-vaccination GMTs between the two groups of subjects having received the adjuvanted vaccines.

Twenty one days after vaccination, the subjects of Fluarix (18-40 years) had a higher HI response for New Caledonia and B/Jangsu strains.

As shown in Table 12 the adjuvanted influenza vaccines exceeded the requirements of the European authorities for annual registration of split virion influenza vaccines ["Note for Guidance on Harmonization of Requirements for Influenza Vaccines for the immunological assessment of the annual strain changes" (CPMP/BWP/214/96)] in subjects aged over 60 years.

After vaccination, there was a statistically difference in terms of seroprotection rates of HI antibodies between Fluarix (65 years) group and Flu/AS01B and Flu/AS01E for A/H1N1/New Caledonia strain For each vaccine strain, the seroprotection rates for the 2 influenza adjuvanted vaccine groups are in the same range compared to Fluarix (18-40 years) group.

For each vaccine strain, the seroconversion rates for the 2 influenza adjuvanted vaccine groups are in the same range compared to Fluarix (18-40 years) group excepted for New Caledonia strain.

TABLE 12

Seroprotection rates seroconversion rates and conversion factors at day 21 (ATP cohort for immunogenicity)

| Strains | Group | N | Seroprotection rate (HI titre ≥40) % | Seroconversion rate (≥4-fold increase) [95% CI] % | Conversion factor [95% CI] % |
|---|---|---|---|---|---|
| | EU standard (>60 years) | | >60% | >30% | >2.0 |
| | EU standard (<60 years) | | >70% | >40% | >2.5 |
| A/New Caledonia (H1N1) | Flu Yng | 75 | 100 [95.20-100] | 77.3 [66.2-86.2] | 35.1 [21.9-56.4] |
| | Flu Elderly | 49 | 71.4 [56.74-83.42] | 30.6 [18.3-45.4] | 3.7 [2.4-5.7] |
| | FluAS01B | 75 | 97.3 [90.70-99.68] | 48.0 [36.5-59.8] | 4.5 [3.3-6.1] |
| | FluAS01E | 75 | 93.3 [85.12-97.80] | 52.0 [40.2-63.7] | 5.0 [3.6-6.9] |
| A/New York (H3N2) | Flu Yng | 75 | 93.3 [85.12-97.80] | 76.0 [64.7-85.1] | 9.2 [7.1-11.8] |
| | Flu Elderly | 49 | 81.6 [67.98-91.24] | 69.4 [54.6-81.7] | 8.2 [5.7-11.8] |
| | FluAS01B | 75 | 96.0 [88.75-99.17] | 85.3 [75.3-92.4] | 13.1 [10.0-17.1] |
| | FluAS01E | 75 | 93.3 [85.12-97.80] | 80.0 [69.2-88.4] | 14.5 [10.4-20.2] |
| B/Jiangsu (B) | Flu Yng | 75 | 100 [95.20-100] | 81.3 [70.7-89.5] | 13.9 [10.1-19.1] |
| | Flu Elderly | 49 | 93.9 [83.13-98.72] | 44.9 [30.7-59.8] | 4.3 [3.0-6.1] |
| | FluAS01B | 75 | 100 [95.20-100] | 65.3 [53.5-76.0] | 5.2 [4.2-6.5] |
| | FluAS01E | 75 | 97.3 [90.70-99.68] | 70.7 [59.0-80.6] | 6.7 [5.1-8.9] |

N = total number of subject;
% = Percentage of subjects with titre at day 21 within the specified range;
CI = confidence interval VI.3.2. Immunogenicity Conclusions Pre-vaccination frequency of influenza-specific CD4 was significantly inferior in elderly adults compared to adults aged between 18 and 40 years. After vaccination with Fluarix™, post-vaccination frequency (day 21) remained inferior in elderly adults compared to younger ones. On the contrary, the non-inferiority in term of frequency of post-vaccination frequency of influenza-specific CD4 after vaccination with adjuvanted vaccines of elderly subjects was demonstrated compared to vaccination with Fluarix™ in adults aged between 18 and 40 years.

Regarding the humoral immune response in term of HI antibody response, all influenza vaccines fulfilled the requirements of the European authorities for annual registration of influenza inactivated vaccines ["Note for Guidance on Harmonisation of Requirements for Influenza Vaccines for the immunological assessment of the annual strain changes" (CPMP/BWP/214/96)]. In elderly adults, adjuvanted vaccines mediated at least a trend for a higher humoral immune response to influenza haemagglutinin than Fluarix™ Significant difference between the humoral immune response against each vaccine strain mediated in elderly subjects by adjuvanted vaccines compared to Fluarix™ are summarised in Table 13. Compared to adults aged between 18 and 40 years vaccinated with Fluarix™, elderly subjects vaccinated with the adjuvanted vaccines showed a trend for higher post-vaccination GMTs and seroconversion factor at day 21 against the A/New York strain.

TABLE 13

Influenza strains for which significantly higher humoral immun response (based on non-overlapping of 95% CI) was observed in elderly subjects vaccinated with the different adjuvanted vaccines compared to Fluarix in the same population.

| | Post-vacc GMT | Seroconversion Factor | Seroprotection rate | Seroconversion Rate |
|---|---|---|---|---|
| FluAS01B | A/New York | | A/New Caledonia | |
| FluAS01E | A/New Caledonia A/New York | | A/New Caledonia | |

Post-vacc GMT = Geometric Mean Titre at post-vaccination

VI.4 Reactogenicity Conclusions

VI.4.1. Recording of Adverse Events (AE)

Solicited symptoms (see Table 14) occurring during a 7-day follow-up period (day of vaccination and 6 subsequent days) were recorded. Unsolicited symptoms occurring during a 21-day follow-up period (day of vaccination and 20+3 subsequent days) were also recorded. Intensity of the following AEs was assessed as described in Table 15.

TABLE 14

Solicited local/general adverse events

| Solicited local AEs | Solicited general AEs |
|---|---|
| Pain at the injection site | Fatigue |
| Redness at the injection site | Fever |
| Swelling at the injection site | Headache |
| Haematoma | Muscle ache |
| | Shivering |
| | Joint pain in the arm of the injection |
| | Joint pain at other locations |

N.B. Temperature was recorded in the evening. Should additional temperature measurements performed at other times of day, the highest temperature was recorded.

TABLE 15

Intensity scales for solicited symptoms in adults

| Adverse Event | Intensity grade | Parameter |
|---|---|---|
| Pain at injection site | 0 | Absent |
| | 1 | on touch |
| | 2 | when limb is moved |
| | 3 | prevents normal activity |
| Redness at injection site | | Record greatest surface diameter in mm |
| Swelling at injection site | | Record greatest surface diameter in mm |
| Haematoma at injection site | | Record greatest surface diameter in mm |
| Fever* | | Record temperature in ° C./° F. |
| Headache | 0 | Absent |
| | 1 | is easily tolerated |
| | 2 | interferes with normal activity |
| | 3 | prevents normal activity |
| Fatigue | 0 | Absent |
| | 1 | is easily tolerated |
| | 2 | interferes with normal activity |
| | 3 | prevents normal activity |
| Joint pain at the injection site and other locations | 0 | Absent |
| | 1 | is easily tolerated |
| | 2 | interferes with normal activity |
| | 3 | prevents normal activity |
| Muscle ache | 0 | Absent |
| | 1 | is easily tolerated |
| | 2 | interferes with normal activity |
| | 3 | prevents normal activity |
| Shivering | 0 | Absent |
| | 1 | is easily tolerated |
| | 2 | interferes with normal activity |
| | 3 | prevents normal activity |

*Fever is defined as axillary temperature ≥37.5° C. (99.5° F.)

The maximum intensity of local injection site redness/swelling is scored as follows:
0 is 0 mm; 1 is >0-≤20 mm; 2 is >20-≤50 mm; 3 is >50 mm.

The maximum intensity of fever is scored as follows:
1 is >37.5-≤38.0° C.; 2 is >38.0-≤39.0° C.; 3 is >39.0

The investigator makes an assessment of intensity for all other AEs, i.e. unsolicited symptoms, including SAEs reported during the study. The assessment is based on the investigator's clinical judgement. The intensity of each AE recorded is assigned to one of the following categories:

1 (mild)=An AE which is easily tolerated by the subject, causing minimal discomfort and not interfering with everyday activities;

2 (moderate)=An AE which is sufficiently discomforting to interfere with normal everyday activities;

3 (severe)=An AE which prevents normal, everyday activities (In adults/adolescents, such an AE would, for example, prevent attendance at work/school and would necessitate the administration of corrective therapy).

VI.4.2. Recording of Adverse Events (AE)

In elderly subjects, the reactogenicity observed with adjuvanted vaccines, in terms of both local and general symptoms was higher than with Fluarix™. Not only the incidence but also the intensity of symptoms was increased after vaccination with adjuvanted vaccines (FIG. 8). Grade 3 symptoms showed a trend to be higher in the group who received the vaccine adjuvanted with the highest immunostimulants (MPL, QS21) concentration compared to the group who received the adjuvanted vaccine wherein the immunostimulants is at a lower concentration. In all cases, symptoms however resolved rapidly.

EXAMPLE VII

Pre-clinical Evaluation of Adjuvanted HPV Vaccines in Mice

This study used a bivalent antigenic composition from human papillomavirus (HPV), combining virus like particles (VLPs) formed from L1 of HPV 16 and L1 from HPV 18 as the antigen. The objective of the study was to compare the efficacy of this antigenic preparation when formulated with AS01B and a 1/5 dilution of AS01B, benchmarked against the current adjuvant found in GSK's cervical cancer vaccine, AS04 (MPL on alum).

VII.1—Vaccination

Mice (n=12 per group) were injected at 0 and 28 days with vaccine formulations composed of HPV16/18 L1 (2 µg or 0.5 µg each) derived from Hi-5 80/80L process and formulated with AS04 (50 µg MPL formulated with alum or AS01B (50 µg QS21—50 µg MPL in 0.5 ml) 1/10 and 1/50 Human dose. As the studies were carried out in mice, 1/10 human dose can be taken to be equivalent to the AS01B human formulation, i.e. 50 µg QS21 and 50 µg MPL in 0.5 ml and 1/50 can be taken to be a 1/5 dilution of the AS01B human formulation i.e. 10 µg QS21 and 10 µg MPL in 0.5 ml. Blood samples were taken at 14 and 45 days post dose 11 to assay for total anti-L1 type specific antibodies in individual sera. Intracellular cytokines staining were measured at days 7 and 14 post II on PBMC and at day 45 post 11 using spleen cells. Frequency of VLPs specific memory B cells were measured at day 45 post 11 using spleen cells.

VII.2—Anti-HPV 16/18 L1 ELISA

Quantification of anti-HPV-16 and HPV-18 L1 antibodies was performed by ELISA using HPV-16 and HPV-18 L1 as coating. Antigens were diluted at a final concentration of 0.5 μg/ml in PBS and were adsorbed overnight at 4° C. to the wells of 96-wells microtiter plates (Maxisorp Immuno-plate, Nunc, Denmark). The plates were then incubated for 1 hr at 37° C. with PBS containing 1% Bovine Serum Albumine (saturation buffer). Sera diluted in buffer containing PBS+ 0.1% Tween20+1% BSA were added to the HPV L1-coated plates and incubated for 1 hr 30 min at 37° C. The plates were washed four times with PBS 0.1% Tween20 and biotin-conjugated anti-mouse Ig (Dako, UK) diluted at 1/1000 in saturation buffer was added to each well and incubated for 1 hr 30 at 37° C. After a washing step, streptavidin-horseradish peroxydase (Dako, UK), diluted 1/3000 in saturation buffer was added for an additional 30 min at 37° C. Plates were washed as indicated above and incubated for 20 min at room temperature with a solution of 0.04% o-phenylenediamine (Sigma) 0.03% $H_2O_2$ in 0.1% Tween20, 0.05M citrate buffer pH 4.5. The reaction was stopped with 2N H2SO4 and read at 492/620 nm. ELISA titers were calculated from a reference by SoftMaxPro (using a four parameters equation) and expressed in EU/ml.

VII.3—Intracellular Cytokines Staining (ICS)

Intracellular staining of cytokines of T cells was performed on PBL at days 7 and 14 post II and on spleen cells at day 45 after the second immunisation. PBMCs (1 pool/group) or spleen cells (4 pools of 3 organs per group) were collected from mice. In vitro antigen stimulation of spleen cells were carried out at a final concentration of 5 $10^6$ cells/ml (microplate 96 wells) with VLP 16 or 18, (5 μg/ml)+CD49d CD28 antibodies (1 μg/ml) and then incubated 3H at 37° C. Following the antigen restimulation step, cells were incubated overnight in presence of Brefeldin (1 μg/ml) at 37° C. to inhibit cytokine secretion. Cell staining was performed as follows: cell suspensions were washed, resuspended in 50 μl of PBS 1% FCS containing 2% Fc blocking reagent (1/50; 2.4G2). After 10 min incubation at 4° C., 50 μl of a mixture of anti-CD4-APC (1/50) and anti-CD8 perCp (1/50) was added and incubated 30 min at 4° C. After a washing in PBS 1% FCS, cells were permeabilized by resuspending in 200 μl of Cytofix-Cytoperm (Kit BD) and incubated 20 min at 4° C. Cells were then washed with Perm Wash (Kit BD) and resuspended with 50 μl of anti-IFγ APC (1/50)+anti-IL-2 FITC (1/50) diluted in PermWash. After 2H incubation at 4° C., cells were washed with Perm Wash and resuspended in PBS 1% FCS+1% paraformaldehyde. Sample analysis was performed by FACS. Live cells were gated (FSC/SSC) and acquisition was performed on ~20,000 events (lymphocytes). The percentages of IFγ+ or IL2+ were calculated on CD4+ and CD8+ gated populations.

VII.4—B Cell Memory

Forty-five days after the second immunisation, mice were sacrificed, spleens cells were separated by a lymphoprep gradient (Cedarlane). B cells were then resuspended in RPMI 1640 medium (Gibco) containing additives (sodium pyruvate 1 mM, MEM non-essential amino acids, Pen/Strep, Glutamine and β-2 mercaptoethanol), 5% foetal calf serum, 50 U/ml rhIL-2 (eBioscience) and 3 μg/ml CpG. Cells were cultured five days at a final concentration of $10^6$ cells/ml, in 5 ml per flat-bottomed 6 wells. After an activation step with ethanol, nitrocellulose plates (Multiscreen-IP; Millipore) were coated with 10 μg/ml of VLPs or with Goat anti-mouse Ig (GAM; Sigma) diluted 1/200 in PBS. After a saturation step with complete medium, 100 μl of $2 \cdot 10^6$ cells/ml were added to VLPs coated plates and 100 μl of $10^6$ and $5 \cdot 10^5$ cells/ml were added to GAM plates. After an incubation time of 2 hrs at 37° C., plates were stored overnight at 4° C. Plates were washed four times with PBS 0.1% Tween20 and anti-mouse Ig Biot diluted 1/200 in PBS 1% BSA 5% FCS (dilution buffer) was distributed to plates and incubated for 2 hrs at 37° c. After a washing step, Extravidin HRP (Sigma) diluted 1/550 in dilution buffer was added for an additional 1 hr at 37° C. Plates were washed as above and incubated for 10 min at room temperature with a solution of AEC (Sigma). Reaction is stopped by rinsing plates gently under tap water. When plates are dried, read with KS400.

VII.5—Statistical Analysis

The formulation means were compared using a one-way analysis of variance (ANOVA 1). The analysis was conducted on log 10 transformed data for normalization purpose. When a significant difference between process means was detected (p-value≤0.05), pair wise comparisons among means were performed at a 0.05 significant level (Student-Newman-Keuls multiple comparison test).

VII.6—Results

Mice were immunized as in VII.1 above. The following groups were used:

| Group | Antigen | Adjuvant | Adjuvant dilution |
|---|---|---|---|
| 1 | HPV 16-18 L1 2 μg | AS04 | 1/10 human dose (equivalent to 50 μg MPL per 0.5 ml HD) |
| 2 | HPV 16-18 L1 0.5 μg | AS04 | 1/50 human dose (equivalent to 10 μg MPL per 0.5 ml HD) |
| 3 | HPV 16-18 L1 2 μg | AS04 | 1/10 human dose (equivalent to 50 μg MPL per 0.5 ml HD) |
| 4 | HPV 16-18 L1 0.5 μg | AS04 | 1/50 human dose (equivalent to 10 μg MPL per 0.5 ml HD) |
| 5 | HPV 16-18 L1 2 μg | AS01B | 1/10 human dose (equivalent to 50 μg MPL per 0.5 ml HD) |
| 6 | HPV 16-18 L1 0.5 μg | AS01B | 1/50 human dose (equivalent to 10 μg MPL per 0.5 ml HD) |
| 7 | HPV 16-18 L1 2 μg | AS01B | 1/10 human dose (equivalent to 50 μg MPL per 0.5 ml HD) |
| 8 | HPV 16-18 L1 0.5 μg | AS01B | 1/50 human dose (equivalent to 10 μg MPL per 0.5 ml HD) |

VII.6.1—Humoral Responses

No significant dose range was observed for the two tested doses of antigens with either dilution of adjuvant for either anti HPV 16-L1 antibody titers or anti HPV 18-L1 antibody titers (FIG. 9)

No significant dose range was observed for the two tested doses of each adjuvant whatever the dose of antigen for anti HPV 16-L1 antibody titers.

When looking at anti HPV 18-L1 antibody titers, a slight increase in titer was seen for AS01B (1/10 HD) compared to AS01B (1/50 HD) as measured at day 14 post II (2.5 fold dose range, p value=0.0035), however this range was observed only for 2 μg antigen and not for 0.5 μg antigen (p value=0.0867), By day 45 post II, no significant dose range was seen for the two tested doses of each adjuvant whatever the dose of antigen.

VII.6.2—Cellular Responses

Intracellular Cytokine Staining

No dose range effect of antigen was observed for the two tested doses of antigens whatever the dose of adjuvant for HPV 18-L1. Similar frequencies of VLP16 specific CD4+ T cells were obtained with the two tested doses of antigens with different doses of adjuvants. (FIG. 10).

A slight dosage effect (2.6 fold, p value=0.0009 for HPV 18-L1, 2 fold, p value=0.0187 for HPV 16-L1) was seen for AS01B (1/10 HD) compared to AS01B (1/50 HD), however this range was observed only for 2 μg antigen and not for 0.5 μg antigen.

Specific B Memory Cells

No dose range effect of antigen was observed for the two tested doses of antigens whatever the dose of adjuvant for HPV 16 or 18 L1 (FIG. 11)

No dose range effect of adjuvant was observed for the two tested doses of adjuvants whatever the dose of antigen for HPV 17 or 18 L1.

As can be seen from the above results, a 1/5 dilution of AS01B produces a formulation which has equivalent efficacy in immunogenic compositions to AS01B itself.

EXAMPLE VIII

Preclinical Evaluation of Adjuvanted S. pneumoniae Vaccines in Mice

The pneumococcal vaccine used in this study was an 11-valent adjuvanted pneumococcal conjugate vaccines (11PCV/AS) consisting of a mixture of 11 pneumococcal polysaccharide conjugates adjuvanted either with AS01B or AS01E. The conjugates consist of the S. pneumoniae serotypes 1, 3, 4, 5, 6B, 7F, 9V, 14, 18C, 19F and 23F purified polysaccharides, each individually conjugated to a carrier protein, either diphtheria toxoid (DT), tetanus toxoid (TT) or protein D from H. influenzae (PD). The vaccines are presented as a freeze-dried powder to be reconstituted with one of the liquid adjuvants.

11 PCV/AS is Produced as Follows:

The activation and coupling conditions are specific for each polysaccharide. These are given in the table below. Sized polysaccharide (except for PS5, 6B and 23F) was dissolved in NaCl 2M or in water for injection (WFI). The optimal polysaccharide concentration was evaluated for all the serotypes. All serotypes except serotype 18C were conjugated directly to the carrier protein as detailed below.

From a 100 mg/ml stock solution in acetonitrile or acetonitrile/water 50%/50% solution, CDAP (CDAP/PS ratio 0.75 mg/mg PS) was added to the polysaccharide solution. 1.5 minute later, 0.2M-0.3M NaOH was added to obtain the specific activation pH. The activation of the polysaccharide was performed at this pH during 3 minutes at 25° C. Purified protein (protein D or DT) (the quantity depends on the initial PS/carrier protein ratio) was added to the activated polysaccharide and the coupling reaction was performed at the specific pH for up to 2 hour (depending upon serotype) under pH regulation. In order to quench un-reacted cyanate ester groups, a 2M glycine solution was then added to the mixture. The pH was adjusted to the quenching pH (pH 9.0). The solution was stirred for 30 minutes at 25° C. and then overnight at 2-8° C. with continuous slow stirring.

Preparation of 18C:

18C was linked to the carrier protein via a linker—Adipic acid dihydrazide (ADH) Polysaccharide serotype 18C was microfluidized before conjugation.

Derivatization of Tetanus Toxoid with EDAC

For derivatization of the tetanus toxoid, purified TT was diluted at 25 mg/ml in 0.2M NaCl and the ADH spacer was added in order to reach a final concentration of 0.2M. When the dissolution of the spacer was complete, the pH was adjusted to 6.2. EDAC (1-ethyl-3-(3-dimethyl-aminopropyl) carbodiimide) was then added to reach a final concentration of 0.02M and the mixture was stirred for 1 hour under pH regulation. The reaction of condensation was stopped by increasing pH up to 9.0 for at least 30 minutes at 25° C.

Derivatized TT was then diafiltrated (10 kDa CO membrane) in order to remove residual ADH and EDAC reagent.

$TT_{AH}$ bulk was finally sterile filtered until coupling step and stored at −70° C.

Chemical Coupling of $TT_{AH}$ to PS 18C

Details of the conjugation parameters can be found in Table 1.

2 grams of microfluidized PS were diluted at the defined concentration in water and adjusted to 2M NaCl by NaCl powder addition.

CDAP solution (100 mg/ml freshly prepared in 50/50 v/v acetonitrile/WFI) was added to reach the appropriate CDAP/PS ratio.

The pH was raised up to the activation pH 9.0 by the addition of 0.3M NaOH and was stabilised at this pH until addition of $TT_{AH}$.

After 3 minutes, derivatized $TT_{AH}$ (20 mg/ml in 0.2 M NaCl) was added to reach a ratio $TT_{AH}$/PS of 2; the pH was regulated to the coupling pH 9.0. The solution was left one hour under pH regulation.

For quenching, a 2M glycine solution, was added to the mixture PS/$TT_{AH}$/CDAP.

The pH was adjusted to the quenching pH (pH 9.0).

The solution was stirred for 30 min at 25° C., and then left overnight at 2-8° C. with continuous slow stirring.

Purification of the Conjugates:

The conjugates were purified by gel filtration using a Sephacryl 500HR gel filtration column equilibrated with 0.15M NaCl (S500HR for 18C) to remove small molecules (including DMAP) and unconjugated PS and protein. Based on the different molecular sizes of the reaction components, PS-PD, PS-TT or PS-DT conjugates are eluted first, followed by free PS, then by free PD or free DT and finally DMAP and other salts (NaCl, glycine). Fractions containing conjugates are detected by $UV_{280\,nm}$. Fractions are pooled according to their Kd, sterile filtered (0.22 μm) and stored at +2-8° C. The PS/Protein ratios in the conjugate preparations were determined.

Specific Activation/Coupling/Quenching Conditions of P S. pneumonia Protein D/TT/DT Conjugates

| Serotype | 1 μfluid | 3 (μfluid.) | 4 μfluid | 5 | 6B | 7F μfluid |
|---|---|---|---|---|---|---|
| PS conc.(mg/ml) | 2.5 | 3.0 | 2.5 | 7.1 | 5.0 | 5.0 |
| PS dissolution | WFI | NaCl 2M | WFI | WFI | NaCl 2M | NaCl 2M |
| PD conc.(mg/ml) | 10.0 | 5.0 | 10.0 | 5.0 | 5.0 | 10.0 |
| Initial PS/PD Ratio (w/w) | 1.5/1 | 1/1 | 1.5/1 | 1/1 | 1.1/1 | 1.2/1 |

-continued

| | | | | | |
|---|---|---|---|---|---|
| CDAP conc. (mg/mg PS) | 0.50 | 0.75 | 0.50 | 0.79 | 0.83 | 0.75 |
| $pH_a = pH_c = pH_q$ | 9.0/9.0/9.0 | 9.0/9.0/9.0 | 9.5/9.5/9.0 | 9.0/9.0/9.0 | 9.5/9.5/9.0 | 9.5/9.5/9.5 |

| Serotype | 9V µfluid | 14 µfluid | 18C µfluid | 19F µfluid | 23F |
|---|---|---|---|---|---|
| PS conc.(mg/ml) | 5.0 | 5.0 | 4.5 | 9.0 | 2.38 |
| PS dissolution | NaCl 2M | NaCl 2M | NaCl 2M | NaCl 2M | NaCl 2M |
| Carrier protein conc.(mg/ml) | 10.0 | 10.0 | 20.0 (TT) | 20.0 (DT) | 5.0 |
| Initial carrier protein/PS Ratio (w/w) | 1.2/1 | 1.2/1 | 2/1 | 1.5/1 | 1/1 |
| CDAP conc. (mg/mg PS) | 0.50 | 0.75 | 0.75 | 1.5 | 0.79 |
| $pH_a = pH_c = pH_q$ | 9.5/9.5/9.0 | 9.5/9.5/9.0 | 9.0/9.0/9.0 | 9.0/9.0/9.0 | 9.5/9.5/9.0 |

The 11 conjugates were then mixed together, and the final antigenic preparation mixed with the appropriate adjuvant before immunisation.

Groups of 40 female 4-weeks old Balb/c mice were immunized IM at days 0.14 and 28 with 0.1 µg of 11-valent PS conjugates formulated with either AS01B or AS01E. Anti-PS IgG antibodies were dosed by ELISA in sera collected at day 42.

Figure 12:
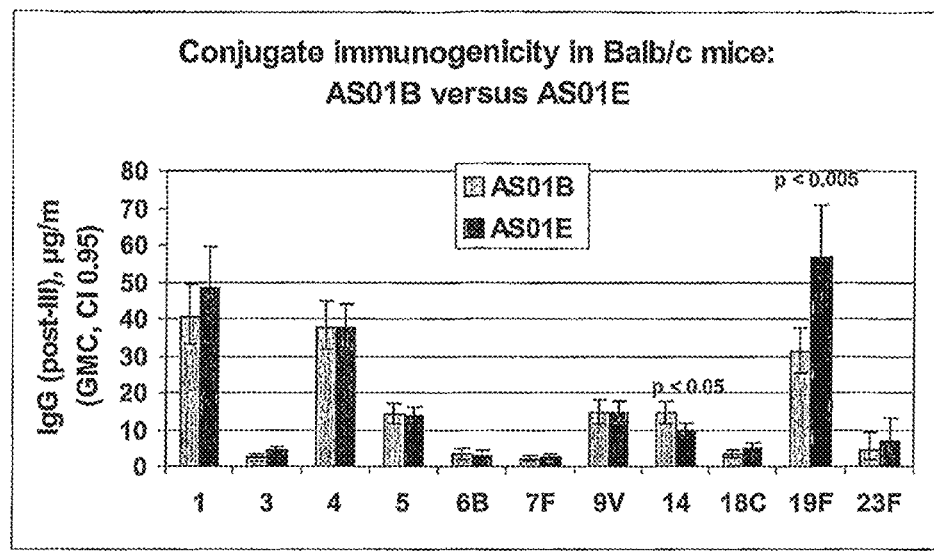

As can be seen from FIG. 12, comparable responses were seen between the diluted AS01E formulation compared to the AS01B formulation except for PS 14 where a higher response was seen with AS01B, and PS 19F where a higher response was seen with AS01E.

EXAMPLE IX

Preclinical Evaluation of Adjuvanted and Non-adjuvanted Cytomegalovirus Immunogenic Compositions IX.1: Guinea Pigs.
IX.1.1 Elisa anti-gB Quantification of anti-gB antibodies was performed by ELISA using gB as a coating antigen. Antigen was diluted at a final concentration of 4 µg/ml in PBS and 100 µl was incubated overnight at 4° C. in 96 well mictrotiter plates. Plastes were then saturated for 1 hour at 37° C. with 200 µl of PBS containing 1% bovine serum albumin. Two-fold serial dilutions of sera were added (100 µl/well) and incubated for 1 hour 30 minutes at 37° C. The plates were washed 4 times with PBS 0.1% Tween 20 and 100 µl of horseradish peroxidase anti-guinea pig IgG (Dako, UK) was added to each well and incubated for 1 hour 30 minutes at 37° C. Plates were washed 4 times with PBS 0.1% Tween 20 and 1 time with water. Then they were incubated for 20 min at 22° C. with 100 µl of a solution of o-phenylenediamine (Sigma) in 0.1M citrate buffer pH 4.2. This reaction was stopped with 100 µl of $H_2SO_4$ 2N and read at 490/620 nm. Elisa titers were determined by interpolation of OD values from a sample reference by SoftMaxPro. Titers were expressed in EU/ml.

Statistical analyses were performed on days 14 post 2 Elisa data using UNISTAT. The protocol applied for analysis of variance can be briefly described as follows:

1) Log transformation of the data
2) Shapiro-Wilk test on each population (group) in order to verify the normality
3) Cochran test in order to verify the homogeneity of variance between different populations (groups)
4) Analysis of variance on selected data (one way)
5) Tuckey-HSD test for multiple comparison.

IX.1.2—Neutralization Assay

Prior to the assay, MRC5 cells (10000 cells/200 µl MEM medium) were distributed in 96 well microplates and incubated for 3 days at 37° C. with $CO_2$. Two-fold dilutions of inactivated sera (30 min at 56° C.) were realized and incubated with 100 µl of viral solution (800/ml) for 1 hour at 37° C. After incubation, 100 µl of serum/virus mixture was inoculated in 96 wells microplates containing MRC5 monolayer. The plates were centrifuged at 2000RPM for 1 hour at 35° C. After an overnight incubation at 37° C., the plates were fixed with an acetone 80% solution (20 minutes at −20° C.). The acetone solution was discarded and CMV positive cells were detected using a specific monoclonal anti-immediate early antigen for 1 hour at 37° C. The plates were washed 3 times with PBS and biotin-conjugated anti-mouse Ig was added to each well and incubated for 1 hour at 37° C. After a washing step, streptavidin-horseradish peroxidase was added for an addition 30 minutes at 37° C. Plates were washed 4 times and incubated for 10 minutes with a solution of True-blue. Specific coloured signals were recorded by examination under microscope. Neutralizing titers were expressed as the reverse of the highest dilution of serum giving 50% reduction of CMV positive cells as compared to a virus control (CMV plus cells without serum).

IX.1.3—Immunization Protocols 4 groups were immunised. Each group contained 8 female Hartley Crl:(ha) Guinea pigs 5-8 weeks old, except for a control group (group 4) containing only 4 subjects. Subjects were immunised IM at 0 and 28 days. Serum samples were collected 28 days after the first immunization and 14 days after the second immunization. Elisas were performed as described above on serum taken at 28 post I and 14 post II. Neutralisation assays were performed as described above at 14 post II. Groups were as below:

| Group | Antigen | Adjuvant |
|---|---|---|
| 1 | gB | NaCl |
| 2 | gB | AS01B |

-continued

| Group | Antigen | Adjuvant |
|-------|---------|----------|
| 3 | gB | AS01E |
| 4 | NaCl | NaCl |

The antigen was prepared as follows: The vaccine antigen is expressed in Chinese Hamster Ovary (CHO) cells as gB, a truncated chimera containing peptide sequences from glycoprotein gD of Herpes Simplex virus 2 (HSV2) at its N and C-terminus. The gB is truncated at its C-terminal domain that contains the membrane anchoring sequence and is therefore secreted into the culture supernatant.

For the first three groups, 15 µg gB** made up in 500 µl of either PBS, AS01B or AS01E (prepared as in example 11.2 above) was injected intramuscularly. In group 4, PBS alone was administered intramuscularly.

IX.1.4—Results

As can be seen in FIG. 13, Significantly higher anti-gB ELISA titres were observed for the two adjuvanted groups as compared to the gB plain (8 and 5.5-fold higher for gB and AS01B and gb/AS01E respectively). Post dose II antibody titers were very slightly higher (1.5 fold) in the gB/AS01B group compared to the gB/AS01E group.

Multiple comparison: Tuckey-HSD

| Group | Cases | Mean | Plain | AS01E | AS01B |
|-------|-------|------|-------|-------|-------|
| Plain | 8 | 4.7917 | | ** | ** |
| AS01E | 8 | 5.5293 | ** | | |
| AS01B | 8 | 5.6942 | ** | | |

Plain<AS01E = AS01B

In respect of neutralising titres (FIG. 14):
No specific neutralising antibodies were observed in the gB plain group
Specific neutralising antibodies were detected in both adjuvanted groups
Similar levels of neutralising antibodies were observed in both adjuvanted groups.

IX.2—Mice
IX.2.1—ELISA anti gB

Quantification of anti-gB antibodies was performed by ELISA using gB as a coating antigen. Antigen was diluted at a final concentration of 1 µg/ml in PBS and 100 µl was incubated overnight at 4° C. in 96 well mictrotiter plates. Plastes were then saturated for 1 hour at 37° C. with 200 µl of PBS containing 1% bovine serum albumin. Two-fold serial dilutions of sera were added (100 µl/well) and incubated for 1 hour 30 minutes at 37° C. The plates were washed 4 times with PBS 0.1% Tween 20 and 100 µl of streptavidin-horseradish peroxidase was added to each well for an additional 30 minutes at 37° C. Plates were washed 4 times with PBS 0.1% Tween 20 and 1 time with water. Then they were incubated for 10 min at 22° C. with 100 µl of tetra-methyl-benzidine 75% in 0.1M citrate buffer pH 5.8. This reaction was stopped with 100 µl of $H_2SO_4$ 0.4N and read at 450/620 nm. Elisa titers were determined by interpolation of OD values from a sample reference by SoftMax-Pro. Titers were expressed in EU/ml.

Statistical analyses were performed on days 14 post 2 Elisa data using UNISTAT. The protocol applied for analysis of variance can be briefly described as follows:
1) Log transformation of the data
2) Shapiro-Wilk test on each population (group) in order to verify the normality
3) Cochran test in order to verify the homogeneity of variance between different populations (groups)
4) Analysis of variance on selected data (one way)
5) Tuckey-HSD test for multiple comparison.

IX.2.2—Neutralization Assay

Prior to the assay, MRC5 cells (10000 cells/200 µl MEM medium) were distributed in 96 well microplates and incubated for 3 days at 37° C. with 5% $CO_2$. Two-fold dilutions (60 µl) of inactivated sera (30 min at 56° C.) were incubated with 60 µl of viral solution (800 IPU/ml) for 1 hour at 37° C. After incubation, 100 µl of sera-virus mixture was inoculated in 96 well microplates containing MRC5 cells. The plates were centrifuged at 2000RPM for 1 hour at 35° C. After an overnight incubation at 37° C., the plates were fixed with an acetone 80% solution (20 minutes at −20° C.). The acetone solution was discarded and CMV positive cells were detected using a specific monoclonal anti-immediate early I (IE-I) antigen for 1 hour at 37° C. The plates were washed 3 times with PBS and biotin-conjugated anti-mouse Ig was added to each well and incubated for 1 hour at 37° C. After a washing step, streptavidin-horseradish peroxidase was added for an addition 30 minutes at 37° C. Plates were washed 4 times and incubated for 10 minutes with a solution of True-blue. Specific coloured signals were recorded by examination under microscope. Neutralizing titers were expressed as the reverse of the highest dilution of serum giving 50% reduction of CMV positive cells as compared to a virus control (CMV plus cells without serum).

IX.2.3—Intracellular Cytokine Staining

Intracellular detection of T cells cytokines were performed on PBLs on days 7 and 21 after the second immunization. PBLs were collected from mice and pooled (1 pool per group). In vitro antigen stimulation of lymphocytes (final concentration of 10*7 cells/ml) were done either with a pool of peptide covering the CMV sequence or with the gB protein. PBLs/antigen mix was incubated 2H at 37° C. Cells were then incubated overnight in the presence of Brefelding (1 µg/ml) at 37° C. to inhibit cytokine secretion.

Cell staining was performed as follows: Cell suspensions were washed, resuspended in 50 µl of PBS 1& FCS containing 2% Fc blocking reagent. After 10 min incubation at 4° C., 50 µl of a mixture of anti-CD4 PE and anti-CD8 perCp was added and incubated 30 minu at 4° C. After a washing step in PBS 1% FCS, cell membranes were permeabilised by resuspension in 200 µl of Cytofix=Cytoperm (kit Beckton Dickinson) and incubated 20 min at 4° C. Cells were then washed with Perm Wash (kit BD) and resuspended with 50 µl of an anti-IFN-gamma APC+anti-IL-2 FITC diluted in PermWash. After 2 hours incubation at 4° C., cells were resuspended in PBS 1% FCS+1% paraformaldehyde.

Sample analysis was performed by FACS. Live cells were gated and acquisition was performed on +/−20000 events. The percentages of IFNg+ or IL2+ were calculated on CD4+ and CD8+ gated populations.

IX.2.4—Immunisation Protocols 4 groups were immunised. Each group contained 12 female C57Bl/6 mice of 4-10 weeks old.

| Group | Antigen | Adjuvant |
|-------|---------|----------|
| 1 | gB | PBS |
| 2 | gB | AS01B |
| 3 | gB | AS01E |
| 4 | NaCl | NaCl |

The antigen was prepared as follows: The vaccine antigen is expressed in Chinese Hamster Ovary (CHO) cells as gB, a truncated chimera containing peptide sequences from glycoprotein gD of Herpes Simplex virus 2 (HSV2) at its N and C-terminus. The gB is truncated at its C-terminal domain that contains the membrane anchoring sequence and is therefore secreted into the culture supernatant.

For each group gB** at a concentration of 1.5 μg/dose was made up in 625 μl of PBS or adjuvant AS01B or AS01E (prepared as in example 11.2 above having a concentration of 100 μl of immunostimulants per ml or 50 μl of immunostimulants per ml respectively). 50 μl (i.e. 1/10 of a human dose of 0.5 ml) was injected intramuscularly. One control group of mice was injected with saline. Injections were performed at days 0 and 28. Serum samples were collected 14 days after the second injections for ELISA and Neutralisation assays. PBLs were collected 7 days and 21 days post second injections for ICS.

IX.2.5—Results

Anti-gB ELISA titers (FIG. 15).

A very weak to undetectable level of anti-gB antibodies was observed in the unadjuvanted gB group. However, a high antibody response (65 and 66 fold higher) was observed in both adjuvant groups, AS01B and AS01E respectively. There was no statistical significance between the AS01B and AS01E group.

Multiple Comparision: Tuckey—HSD

| Group | Cases | Mean | Plain | AS01E | AS01B |
|---|---|---|---|---|---|
| Plain | 12 | 2.1132 | | ** | ** |
| AS01E | 12 | 3.9317 | ** | | |
| AS01B | 12 | 3.9375 | ** | | |

Plain<AS01E = AS01B

Anti-CMV neutralizing titers (FIG. 16)

Significantly higher anti-gB neutralising titers were observed for the two adjuvanted groups as compared to the gB plain group. No significant difference in neutralising antibody titres was observed between the AS01B and AS01E formulations.

Cell Mediated Immunity.

Due to the very low level of response observed after restimulation of 7 post II samples, no discrimination can be done between groups and no conclusive response for CD4 and CD8 stimulation can be seen (FIG. 17). These low to undetectable responses were probably due to a technical issue during sample preparations. However, responses could be seen 21 days post second injection. The CD4 data (FIG. 18) shows no difference after restimulation by gB (5 μg/ml) or peptides (2 μg/ml or 4 μg/ml). A similar cytokine profile is seen for AS01E and AS01B. No conclusive response can be seen for CD8 stimulation (FIG. 19)

These experiments show that for another antigenic composition and in two different organisms, an adjuvant having lower levels of immunostimulants is as immunologically effective as that having higher levels.

X: Preclinical Evaluation of Adjuvanted RTS,S Vaccine

X.1—Formulation

The antigenic composition, RTS, S is produced in *Saccharomyces cervisiae* and consists of two proteins, RTS and S, that intracellularly and spontaneously assemble into mixed polymeric particulate structures that are each estimated to contain, on average, 100 polypeptides. RTS is a 51 kDa hybrid polypeptide chain of 424 amino acids consisting of 189aa derived from a sporozoite surface antigen of the malaria parasite *P. falciparum* strain NF53 (the CSP antigen, a.a. 207 to 395), fused to the amino terminal end of the hepatitis B virus S protein. S is a 24 kDa polypeptide (226 amino acids long) corresponding to the surface antigen of hepatitis B virus. The lyophilised antigen pellet contains approximately 50 μg (when designed to be formulated in 0.5 ml with AS01B) or 25 μg (when designed to be formulated in 0.5 ml with AS01E) of antigen.

AS01B and AS01E were prepared by mixing the various components (PBS, liposomes, MPL and QS21) in a tank, and stirring under aseptic conditions. The product was then sterile filtered before filling into vials or syringes. The liquid adjuvant was stored at +2° C. to +8° C. before being used to reconstitute the lyophilised antigen pellet.

X.2—Mice Experiments

Two experiments in mice were performed aiming at comparing the immune responses specific to RTS,S induced by RTS,S/AS01B as compared to RTS,S formulated with AS01E. In each experiment, C57Bl/6 mice (10 mice/group) were immunised intramuscularly three times two weeks apart with 10, 5 or 2.5 μg of RTS,S formulated with AS01B or AS01E adjuvants. AS controls, two groups were immunised with either AS01B or AS01E alone. The antibody responses specific to HBs and CS were assessed for each mouse by ELISA 15 days after the third immunisation. The geometric mean antibody titres and their 95% confidence intervals were calculated for all the mice receiving the same treatment in both experiments. Statistical analyses to evaluate adjuvant effect and antigen dose effects were performed on pooled data from both experiments. The CD4 and CD8 specific T cell responses were measured by flow cytometry 7 days after the second and third immunizations on pools of blood cells from 5 mice per group. Thus two values were generated for each group in each experiment.

Humoral Immune Response

As shown in FIGS. 20 and 21, both AS01B and AS01E adjuvants induce strong comparable antibody responses against CSP and HBs.

A three-way ANOVA on anti-CSP GMTs showed that there was no significant differences between AS01B and AS01E for the 5 or 2.5 μg doses of RTS,S.

For the 10 μg dose, AS01B adjuvant was found to induce higher anti-CS titers than AS01E and the GMT ration "AS01B group/AS01E group" was 1.93 (95% CI: 1.33-2.79; p=0.001)

Cell Mediated Specific Immune Response

FIGS. 22 and 23 show the levels of CD4 and CD8 T cells specific for CSP and HBs that express IL-2 and/or IFN gamma.

The CD4 response specific for CSP tends to be higher with AS01B as compared to AS01E after three immunizations whereas the CD8 T cell response with AS01E are equivalent to or better than with AS01B.

The CD4 response specific for HBs tends to be higher with AS01B as compared to AS01E after three immunizations except for the lower dose of RTS,S where the levels of CD4 T cells are comparable between the two adjuvants. The HBs specific CD8 T cell responses induced by RTS,S formulated with AS01E are equivalent to or better than the responses induced by RTS,S formulated with AS01B.

These differences are thought to be within the expected variability of cellular immunology assays.

Pre-clinical evaluation of the RTS,S/AS01E vaccine in mice revealed an acceptable safety profile, similar to that of RTS,S/AS01B.

XI: Clinical Evaluation of RTS,S/AS01E.

Formulations are prepared as in example X above. Sucrose is used as an excipient in the lyophillised antigen pellet. As in example X, the liquid adjuvant is used to reconstitute the lyophillised antigen. AS01E was prepared as described in example 11.2, and stored at +2 to +8° C. until needed for reconstitution.

A phase II randomized double-blind study of the safety and immunogenicity of RTS,S adjuvanted with AS01E is currently underway in children aged 18 months to 4 years living in Gabon. The vaccination schedule is a 0, 1, 2-month vaccination schedule. Objectives are as follows for RTS,S/AS01E when administered as 3 doses intramuscularly on a 0,1,2-month schedule to children aged 18 months to 4 years living in a malaria-endemic area:

Coprimary
- to assess safety until one month post Dose 3.
- To demonstrate non-inferiority to an oil in water emulsion adjuvanted RTS,S vaccine in terms of anti-CS antibody response one month post Dose 3.

Secondary
- to assess reactogenicity until one month post Dose 3
- to demonstrate non-inferiority to an oil in water emulsion adjuvanted RTS,S vaccine in terms of anti HBs antibody response one month post Dose 3
- to describe seroprotection against hepatitis B up to one month post Dose 3
- to describe the anti-CS response up to one month post Dose 3

Tertiary
- Safety between 1 month post Dose 3 until 12 months post Dose 3
- Humoral immune response to CS antigen at 12 months post Dose 3
- Humoral immune response to HBs antigen at 12 months post Dose 3

Exploratory
- to evaluate T-cell mediated immune response to CS antigen up to 12 months post dose 3
- to evaluate B-cell memory immune response to CS antigen up to 12 months post dose 3
- to describe the anti-CS response up to one month post Dose 3 according to documented HBV immunization status at screening.

180 subjects were enrolled, 90 were given a vaccine adjuvanted with a previously validated proprietary oil in water emulsion adjuvant (termed "control" in the tables below) and 90 were given a vaccine adjuvanted with AS01E. Healthy male and female children aged 18 months to 4 years of age were screened. Vaccines were administered by the IM route to the left deltoid.

Incidence and Nature of Symptoms (Solicited and Unsolicited) Reported During the 7-Day (Days 0-6) Post-Vaccination Period Following Each Dose and Overall (Total Vaccinated Cohort)

|  |  | Any symptom | | | | | General symptoms | | | | | Local symptoms | | | | |
|---|---|---|---|---|---|---|---|---|---|---|---|---|---|---|---|---|
|  |  |  |  |  | 95% CI | |  |  |  | 95% CI | |  |  |  | 95% CI | |
|  | Group | N | n | % | LL | UL | N | n | % | LL | UL | N | n | % | LL | UL |
| Dose 1 | Gr 1 | 90 | 40 | 44.4 | 34.0 | 55.3 | 90 | 23 | 25.6 | 16.9 | 35.8 | 90 | 20 | 22.2 | 14.1 | 32.2 |
|  | Gr 2 | 90 | 47 | 52.2 | 41.4 | 62.9 | 90 | 26 | 28.9 | 19.8 | 39.4 | 90 | 32 | 35.6 | 25.7 | 46.3 |
| Dose 2 | Gr 1 | 88 | 50 | 56.8 | 45.8 | 67.3 | 88 | 36 | 40.9 | 30.5 | 51.9 | 88 | 35 | 39.8 | 29.5 | 50.8 |
|  | Gr 2 | 87 | 53 | 60.9 | 49.9 | 71.2 | 87 | 39 | 44.8 | 34.1 | 55.9 | 87 | 34 | 39.1 | 28.8 | 50.1 |
| Dose 3 | Gr 1 | 83 | 78 | 94.0 | 86.5 | 98.0 | 83 | 34 | 41.0 | 30.3 | 52.3 | 83 | 76 | 91.6 | 83.4 | 96.5 |
|  | Gr 2 | 85 | 82 | 96.5 | 90.0 | 99.3 | 85 | 50 | 58.8 | 47.6 | 69.4 | 85 | 79 | 92.9 | 85.3 | 97.4 |
| Overall/dose | Gr 1 | 261 | 168 | 64.4 | 58.2 | 70.2 | 261 | 93 | 35.6 | 29.8 | 41.8 | 261 | 131 | 50.2 | 44.0 | 56.4 |
|  | Gr 2 | 262 | 182 | 69.5 | 63.5 | 75.0 | 262 | 115 | 43.9 | 37.8 | 50.1 | 262 | 145 | 55.3 | 49.1 | 61.5 |
| Overall/subject | Gr 1 | 90 | 87 | 96.7 | 90.6 | 99.3 | 90 | 60 | 66.7 | 55.9 | 76.3 | 90 | 83 | 92.2 | 84.6 | 96.8 |
|  | Gr 2 | 90 | 85 | 94.4 | 87.5 | 98.2 | 90 | 70 | 77.8 | 67.8 | 85.9 | 90 | 84 | 93.3 | 86.1 | 97.5 |

Gr. 1 = RTS, S.AS01E
Gr. 2 = control
LL = lower limit
UL = upper limit
For each dose and overall/subject:
N = number of subjects with at least one administered dose
n/% = number/percentage of subjects presenting at least one type of symptom whatever the study vaccine administered
For overall/dose:
N = number of administered doses
n/% = number/percentage of doses followed by at least one type of symptom whatever the study vaccine administered
95% CI = exact 95% confidence interval,
LL = Lower Limit,
UL = Upper Limit These data demonstrate that an AS01E adjuvanted RTS,S vaccine gave acceptable reactogenicity results in a paediatric population when compared with a control formulation.

Serological responses were measured by evaluating antibody responses to HBs and to CSP repeats (anti R32LR). Serum for antibody determination was collected at screening, at day 60 and at day 90 (at second vaccination and at third vaccination). Antibody levels against CS were measured by standard ELISA methodology using plate adsorbed R32LR antigen with a standard reference antibody as a control according to SOPs from the laboratory. Results are reported in EU/mL.

Antibody to hepatitis B surface antigen was measured using a commercially available ELISA immunoassay (AUSAB EIA test kit from Abbott) or equivalent according to the assay instructions. Results are reported in mIU/mL.

Seropositivity Rates and GMCs for Anti-CS Antibodies (Total Vaccinated Cohort)

| Antibody | Group | Timing | N | n | % | >=0.5 ELU/ML 95% CI LL | >=0.5 ELU/ML 95% CI UL | GMC value | GMC 95% CI LL | GMC 95% CI UL | Min | Max |
|---|---|---|---|---|---|---|---|---|---|---|---|---|
| Anti-CS | Gr 1 | SCREENING | 89 | 0 | 0.0 | 0.0 | 4.1 | 0.3 | 0.3 | 0.3 | <0.5 | <0.5 |
| | | PII(D60) | 78 | 78 | 100 | 95.4 | 100 | 81.9 | 64.9 | 103.2 | 4.6 | 568.6 |
| | | PIII(D90) | 75 | 75 | 100 | 95.2 | 100 | 215.6 | 178.8 | 259.9 | 14.3 | 1922.3 |
| | Gr 2 | SCREENING | 90 | 1 | 1.1 | 0.0 | 6.0 | 0.3 | 0.2 | 0.3 | <0.5 | 0.5 |
| | | PII(D60) | 78 | 78 | 100 | 95.4 | 100 | 56.9 | 45.7 | 70.9 | 3.6 | 2380.9 |
| | | PIII(D90) | 80 | 80 | 100 | 95.5 | 100 | 164.8 | 134.1 | 202.6 | 6.3 | 2093.6 |

Gr. 1 = RTS, S.AS01E
Gr. 2 = Control
GMC = geometric mean antibody concentration calculated on all subjects
N = number of subjects with available results
n/% = number/percentage of subjects with concentration within the specified range
95% CI = 95% confidence interval;
LL = Lower Limit,
UL = Upper Limit
MIN/MAX = Minimum/Maximum Seropositivity Rates and GMCs for Anti-HBs Antibodies (Total Vaccinated Cohort)

| Antibody | Group | Timing | N | n | % | >=10 MIU/ML 95% CI LL | >=10 MIU/ML 95% CI UL | GMC value | GMC 95% CI LL | GMC 95% CI UL | Min | Max |
|---|---|---|---|---|---|---|---|---|---|---|---|---|
| Anti-HBs | Gr 1 | SCREENING | 89 | 43 | 48.3 | 37.6 | 59.2 | 40.8 | 23.3 | 71.4 | <10.0 | 46421.6 |
| | | PII(D60) | 78 | 77 | 98.7 | 93.1 | 100 | 8936.4 | 4684.2 | 17048.7 | <10.0 | 1615367 |
| | | PIII(D90) | 75 | 75 | 100 | 95.2 | 100 | 24527.7 | 15316.5 | 39278.5 | 21.1 | 1694306 |
| | Gr 2 | SCREENING | 90 | 37 | 41.1 | 30.8 | 52.0 | 20.0 | 12.8 | 31.0 | <10.0 | 30796.4 |
| | | PII(D60) | 78 | 77 | 98.7 | 93.1 | 100 | 3640.0 | 1963.1 | 6749.3 | <10.0 | 1508114 |
| | | PIII(D90) | 80 | 80 | 100 | 95.5 | 100 | 19485.0 | 13511.3 | 28099.9 | 178.6 | 1103974 |

Gr. 1 = RTS, S.AS01E
Gr. 2 = Control
GMC = geometric mean antibody concentration calculated on all subjects
N = number of subjects with available results
n/% = number/percentage of subjects with concentration within the specified range
95% CI = 95% confidence interval;
LL = Lower Limit,
UL = Upper Limit
MIN/MAX = Minimum/Maximum These data demonstrate that an AS01E adjuvanted RTS,S vaccine formulation gave acceptable humoral immune responses in a paediatric population when compared to a validated control.

EXAMPLE XII

Preclinical Evaluation of Varicella Zoster Virus with AS01B Compared to AS01E The candidate vaccine is composed of a truncated VZV envelope protein, gE, produced in CHO cells.

For this study C57Bl/6 mice (n=48) were primed with one human dose (HD) of Varilrix (~4 log pfu/dose) administered sub-cutaneously. Five weeks after priming with Varilrix, mice were divided into to 5 groups of 12 mice and injected intra-muscularly (tibias) on days 0 and 28 with 5 µg of gE alone, 5 µg gE+AS01E* (1/10 HD) or 5 µg gE+AS01B (1/10 HD). The control group of mice (primed only) was injected with saline (0.9% NaCl). Immune responses were evaluated at 14 and/or 30 days following the second vaccination.

Levels of gE specific total antibodies and the frequency of cytokine producing (IL2/1FNγ) CD4 and CD8 T cells were evaluated.

gE Specific Antibody Responses:

An ELISA was developed to detect and quantify gE-specific antibodies in mice sera, using gE protein as the coating antigen. The ELISA titers were defined as the reciprocal of the serum dilution, which produced an absorbance (optical density) measure equal to 50% of the maximal absorbance value. ELISA titers were calculated by regression analysis.

The data demonstrate that gE AS01E and gE AS01B induced similar levels of gE specific antibodies (pvalues>0.05). Both formulations induced significantly higher responses compared to the gE antigen alone (10-13 fold, pvalues<0.05) at both 14 and 30 days post II (FIG. 26).

|           | 14 days post II |       |        | 30 days post II |       |       |
|           |                 | 95% CI |       |                 | 95% CI |       |
| Group     | GMT (EU/ml)     | LL    | UL     | GMT (EU/ml)     | LL    | UL    |
|-----------|-----------------|-------|--------|-----------------|-------|-------|
| gE        | 12067           | 5960  | 24433  | 3832            | 911   | 16115 |
| gE/AS01E  | 125934          | 95504 | 166059 | 50439           | 38071 | 66825 |
| gE/AS01B  | 131728          | 88112 | 196934 | 47589           | 36158 | 62635 |
| Varilrix  | 34              | 11    | 105    | 33              | 10    | 102   | gE Specific CD4 and CD8 Responses

Cytokine production was evaluated in CD4 and CD8 T cells using an intra-cellular cytokine staining technique. Spleen cells were isolated from each group of 12 mice at 30 days post II and pooled into 4 groups of 3 spleens. Spleen cells ($1\times10^6$) were incubated for 2 hours in the presence of gE peptides (63 peptides) spanning the complete gE protein (20 aa peptides/10 aa overlap) and then incubated overnight in the presence of brefeldin. Subsequently cells were stained with fluorescent mAb specific for cell surface CD4/CD8 and following permeabilization intracellular cytokines IL-2 and IFN-gamma.

As shown in FIG. 26 although similar cytokine profiles (IL2/IFNγ) were induced with both gE AS01B and gE AS01E formulations, the AS01B formulation induced a higher magnitude of both CD4 and CD8 cytokine producing cells (2 fold, $p>0.05$ for CD4, 3.6 fold, $p>0.05$ for CD8). Due to unexpectedly high variability of the T cell responses the power to detect a significant difference between adjuvant doses was very limited (<50%). Importantly both gE formulated with AS01B or AS01E induced cytokine producing CD4 T cells of a significantly higher magnitude (13.3 fold, $p<0.05$) compared to gE alone. Higher levels of CD8 cells were also induced by gE formulated with AS01B or AS01E (3.8 fold, $p>0.05$) compared to gE antigen alone.

EXAMPLE XIII

Preclinical Evaluation of AS01B v AS01E in an Influenza Ferret Model

Materials and Methods

Female ferrets (*Mustela putorius* furo) aged 4-6 months were obtained from MISAY Consultancy (Hampshire, UK). Ferrets were primed on day 0 with heterosubtypic strain H1N1 A/Stockholm/24/90, (4 Log TCID50/ml), 250 µl administered intranasally. On day 21, ferrets were injected intramuscularly with a full human dose (1000 µl vaccine dose, 15 µg HA per A strain, 17.5 µg B strain) of a combination of H1N1 A/New Caledonia C/20/99 (15 µg/ml), H3N2 A/Wyoming/3/2003 (15 µg/ml) and B/Jiangsu/10/2003 (17.5 µg/ml). Ferrets were then challenged on day 42 by intranasal route with 250 µl of a heterosubtypic strain Wh.A/NY/55/04 (4.51 Log TCID50/ml).

Vaccinations on day 21 were either with the plain trivalent formulation ("plain" in the tables below) or with the trivalent formulation adjuvanted with AS01B ("AS01B" in the tables below) or AS01E ("AS01E" in the tables below). Formulations were prepared as set out in example 3 above.

Body Temperature Monitoring:

Individual temperatures were monitored during the challenge period and were assessed using telemetry implants which recorded each individual animal temperature every 15 minutes before and after the challenge. All implants were checked and refurbished and a new calibration was performed by DSI before placement in the intraperitoneal cavity. All animals were individually housed in single cage during these measurements.

Temperatures were recorded every 15 minutes 6 days before priming until 4 days post-priming, as well as 3 days before challenge until 7 days post-challenge.

Hemagglutination Inhibition Test (HI).

Test Procedure

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pretreatment, two-fold dilutions of sera were incubated with 4 hemagglutination units of each influenza strain. Chicken red blood cells were then added and the inhibition of agglutination was scored using tears for reading. The titers were expressed as the reciprocal of the highest dilution of serum that completely inhibited hemagglutination. As the first dilution of sera was 1:10, an undetectable level was scored as a titer equal to 5.

Statistical Analysis

Statistical analysis was performed on HI titers using UNISTAT. The protocol applied for analysis of variance can be briefly described as followed:

- Log transformation of data.
- Shapiro-wilk test on each population (group) in order to verify the normality of groups distribution.
- Cochran test in order to verify the homogenicity of variance between the different populations (groups).
- One-way analysis of variance performed on groups.
- Tuckey-HSD Test for multiple comparisons.

Viral Titration in Nasal Washes

All nasal samples were first sterile filtered through Spin X filters (Costar) to remove any bacterial contamination. 50 µl of serial ten-fold dilutions of nasal washes were transferred to microtiter plates containing 50 µl of medium (10 wells/dilution). 100 µl of MDCK cells ($2.4\times10^5$ cells/ml) were then added to each well and incubated at 35° C. for 6-7 days. After 6-7 days of incubation, the culture medium is gently removed and 100 µl of a 1/20 WST-1 containing medium is added and incubated for another 18 hours. The intensity of the yellow formazan dye produced upon reduction of WST-1 by viable cells is proportional to the number of viable cells present in the well at the end of the viral titration assay and is quantified by measuring the absorbance of each well at the appropriate wavelength (450 nanometers). The cut-off is defined as the OD average of uninfected control cells—0.3 OD (0.3 OD correspond to +/−3 StDev of OD of uninfected control cells). A positive score is defined when OD is <cut-off and in contrast a negative score is defined when OD is >cut-off. Viral shedding titers were determined by Reed and Muench, Am J Epidemiol 1938: 493 and expressed as Log $TCID_{50}$/ml.

Lymphoproliferation Assay.

PBMC were collected by density gradient centrifugation (20 min at 2500 rpm and 4° C.) on Ficoll Cedarlane lympholyte mammal solution. PBMC were resuspended in 5 ml culture medium (RPMI/Add at 4° C.) and 10% of normal ferret serum. Additives were composed by 100 mM sodium pyruvate, non essential amino acids MEM, Penicillin/streptamycine, glutamine and 1000× concentrated β2-mercaptoethanol. Freshly isolated PBMC were immediately used for in vitro proliferation assays. The cells were placed in 96-well flat bottom tissue culture plates at $2 \times 10^5$ cells/well and cultured with different concentrations of antigen (0.1 to 1 μg HA of whole inactivated virus) for 44 to 96 h and then were pulse labeled with 0.5 μCi of [$^3$H]thymidine. Incorporation of radiolabel was estimated 4 to 16 h later by β-emission spectroscopy.

Results

Viral load in nasal washes after challenge.

Nasal washes were collected 2 days before priming (priming=day 0) 1, 2 and 7 days post priming, as well as 4 days before challenge (challenge=day 42) and for a period of 7 days post challenge.

| Group | −2 | 0 | +1 | +2 | +7 | 39 | 42 | 43 | 44 | 45 | 47 | 49 |
|---|---|---|---|---|---|---|---|---|---|---|---|---|
| Plain | 0.82 | | 1.84 | 5.35 | 1.85 | 0.8 | | 1.82 | 5.77 | 4.44 | 1.97 | 0.9 |
| AS01E | 0.82 | | 2.11 | 5.83 | 1.65 | 0.8 | | 1.62 | 4.93 | 4.15 | 2.4 | 0.85 |
| AS01B | 0.81 | | 2.26 | 5.38 | 1.91 | 0.82 | | 1.74 | 2.25 | 1.89 | 1.350 | 0.9 |

See results in FIG. 27.

Viral Shedding after Priming

A peak of viral shedding was observed in all ferrets 2 days after the priming.

7 days post priming, only residual viral load was observed in all groups.

Viral Shedding after Challenge

The peak of viral shedding was observed 24 hours after challenge.

Viral titration 3 days post-challenge showed high viral titers (no protection) in ferrets immunized with trivalent split plain. Lower reduction of viral shedding was observed in ferrets immunised with trivalent split AS01E than was seen with trivalent split adjuvanted with AS01B.

Temperature Monitoring:

Body temperature was monitored from 6 days pre-priming (priming=day 0) until 4 days post-priming as well as from 3 days pre-challenge until 7 days post challenge (challenge=day 42). Measurements were taken every 15 minutes and an average calculated by mid-day for each group. Results can be seen in FIG. 28.

Post Priming

Body temperature monitored before, during and after priming did show an increase in temperature in all groups.

Post-Challenge

Interpretation of body temperature monitoring is difficult. A slight increase of body temperature was observed post-challenge in ferrets immunized with trivalent split plain and trivalent split AS01E, but not with trivalent split AS01B. The score below was obtained by the number of ferrets with an increase of body temperature>0.4° C.

Increase in Temperature Post Challenge

Trivalent plain: 5/8 (+0.4, +0.4, +0.5, +0.7, +0.8)
Trivalent AS01B 0/8
Trivalent AS01E 6/8 (+0.4, +0.4, +0.5, +0.5, +0.9, +1.6)

This read out is less robust than other read outs used in ferrets.

Haemagglutination Inhibition Test (HI)

Serum samples were collected 4 days before priming, 17 days post-priming, 21 days post-immunization and 13 days post challenge. Results can be seen in FIGS. 29 and 30. For all three vaccine strains, statistically significantly higher HI titers were observed in ferrets immunised with trivalent split adjuvanted with AS01B or AS01E compared to trivalent split plain. No difference was observed between the two adjuvanted groups. Compared to other groups statistically significant higher cross-reactive HI titers to A/New York H3N2 (challenge strain) were observed after immunisation of ferrets with trivalent split vaccines adjuvanted with AS01B.

What is claimed is:

1. A method of vaccination of a human individual comprising intramuscular delivery of a human dose of an immunogenic composition comprising an antigen in combination with an adjuvant, which adjuvant comprises the QS21 saponin fraction of Quil A from the bark of *Quillaja saponaria Molina* presented in the form of a liposome and a lipopolysaccharide, wherein said saponin fraction and said lipopolysaccharide are each present in said human dose at a level of about 25 μg, wherein the antigen is selected from the group consisting of a *Moraxella catarrhalis* protein antigen and a non-typeable *Haemophilus influenzae* protein antigen, wherein said adjuvant further comprises a sterol, wherein the ratio of saponin:sterol is from 1:1 to 1:100 w/w.

2. The method according to claim 1, wherein the ratio of saponin:sterol is from 1:1 to 1:5 w/w.

3. The method according to claim 1, wherein said sterol is cholesterol.

4. The method according to claim 1, wherein the lipopolysaccharide is 3D-MPL and the ratio of QS21:3D-MPL is 1:1 w/w.

5. The method of claim 1, wherein the antigen is *Moraxella catarrhalis* protein antigen UspA2.

6. The method of claim 1, wherein the antigen is non-typeable *Haemophilus influenzae* antigen Protein D.

7. A method of vaccination of a human individual comprising intramuscular delivery of a human dose of an immunogenic composition comprising an antigen selected from the group consisting of a *Moraxella catarrhalis* protein antigen and a non-typeable *Haemophilus influenzae* protein antigen, in combination with an adjuvant, which adjuvant comprises the QS21 saponin fraction of Quil A from the bark of *Quillaja saponaria Molina* presented in the form of a liposome and a lipopolysaccharide, wherein said saponin fraction and said lipopolysaccharide are each present in said human dose at a level of below 30 µg.

8. The method according to claim 7, wherein said adjuvant further comprises a sterol, wherein the ratio of saponin:sterol is from 1:1 to 1:100 w/w.

9. The method according to claim 8, wherein the ratio of saponin:sterol is from 1:1 to 1:5 w/w.

10. The method according to claim 8, wherein said sterol is cholesterol.

11. The method according to claim 7, wherein the lipopolysaccharide is 3D-MPL and the ratio of QS21:3D-MPL is 1:1 w/w.

12. The method of claim 7, wherein the antigen is *Moraxella catarrhalis* protein antigen UspA2.

13. The method of claim 7, wherein the antigen is non-typeable *Haemophilus influenzae* antigen Protein D.

* * * * *